(12) United States Patent
Anderson et al.

(10) Patent No.: US 6,903,132 B2
(45) Date of Patent: Jun. 7, 2005

(54) NON-PEPTIDE GNRH AGENTS, PHARMACEUTICAL COMPOSITIONS AND METHODS FOR THEIR USE

(75) Inventors: Mark B. Anderson, Orinda, CA (US); Lance Christopher Christie, Ballwin, CA (US); Quyen-Quyen Thuy Do, San Diego, CA (US); Jun Feng, Carlsbad, CA (US); Yufeng Hong, San Diego, CA (US); Haitao Li, San Diego, CA (US); Ved P. Pathak, San Diego, CA (US); Ranjan Jagath Rajapakse, San Diego, CA (US); Eric T. Sun, San Diego, CA (US); Eileen Valenzuela Tompkins, Escondido, CA (US)

(73) Assignees: Agouron Pharmaceuticals, Inc., San Diego, CA (US); Pfizer Inc., New York, NY (US)

( * ) Notice: Subject to any disclaimer, the term of this patent is extended or adjusted under 35 U.S.C. 154(b) by 51 days.

(21) Appl. No.: 10/459,364

(22) Filed: Jun. 11, 2003

(65) Prior Publication Data

US 2004/0014787 A1 Jan. 22, 2004

Related U.S. Application Data

(60) Provisional application No. 60/388,788, filed on Jun. 13, 2002.

(51) Int. Cl.[7] ..................... A61K 31/341; C07D 307/34
(52) U.S. Cl. ..................... 514/461; 549/429; 549/483; 549/487; 544/212; 544/242; 544/297; 546/268.1; 546/276.4; 546/283.4
(58) Field of Search ..................... 549/429, 483, 549/487; 514/461; 544/297; 546/283.4

(56) References Cited

U.S. PATENT DOCUMENTS

| 5,981,521 A | 11/1999 | Haviv et al. |
| 6,355,653 B1 * | 3/2002 | Trottmann et al. ........... 514/303 |
| 6,503,949 B1 * | 1/2003 | Lau et al. .................... 514/617 |

FOREIGN PATENT DOCUMENTS

| EP | 1 334 972 A1 | 8/2003 |
| WO | WO 93/03058 | 2/1993 |
| WO | WO 96/34012 | 10/1996 |
| WO | WO 96/38438 | 12/1996 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 99/44987 | 9/1999 |
| WO | WO 99/50276 | 10/1999 |
| WO | WO 00/04013 | 1/2000 |
| WO | WO 00/12521 | 3/2000 |
| WO | WO 00/12522 | 3/2000 |
| WO | WO 00/20358 | 4/2000 |
| WO | WO 00/68959 | 11/2000 |
| WO | WO 01/29044 | 4/2001 |
| WO | WO 02/098363 | 12/2002 |

OTHER PUBLICATIONS

Millet, et al., "Antitrypanosomal Activities and Cytotoxicity of 5–Nitro–2–furancarbohydrazides," *Bioorganic and Medicinal Chemistry Letters*, 2002, 3601–3604, vol. 12.

Perrier, et al., "Mimicking dominant Negative Inhibition of Prion Replication through Structure–based Drug Design," *Proc. National Acad. Of Science*, 2002, 6073–6078, vol. 97, No. 11.

Abdel–Magid, et al., "Reductive Amination of Aldehydes and Ketones with Sodium Triacetoxyborohydride," *J. Org. Chem.*, 1996, pp. 3849, vol. 61.

Anastasis, et al., "Analogues of Antijuvenile Hormones", *J. Chem. Soc. Perkin Trans. I*, 1982, p. 2013.

Bagshawe, et al., "Antibody–Directed Enzyme Prodrug Therapy: A Review", *Drug Dev. Res.*, 1995, pp. 220–230, vol. 34.

Bertolini, et al., "A New Rational Hypothesis for the Pharmacophore of the Active Metabolite of Leflunomide, a Potent Immunosuppressive Drug", *J. Med. Chem.*, 1997, pp. 2011–2016, vol. 40.

Bodor, "Novel Approaches to the Design of Safer Drugs: Soft Drugs and Site–Specific Chemical Delivery Systems", *Advances in Drug Res.*, 1984, pp. 224–231, vol. 13.

Bowers, et al., "On the Inhibitory Effects of Luteinizing Hormone–Releasing Hormone Analogs", *Endocrinology*, 1980, pp. 675–683 (in vitro).

Bundgaard, *Design of Prodrugs*, (1985, Elsevier Press; Amsterdam—New York—Oxford).

Cheng, et al., "Relationship Between the Inhibition Constant ($K_1$) and the Concentration of Inhibitor Which Causes 50 Per Cent Inhibition ($I_{50}$) of an Enzymatic Reaction*", *Biochemical Pharmacol.*, 1973, pp. 3099–3108, vol. 22.

Cho, et al., "Discovery of a Novel, Potent, and Orally Active Nonpeptide Antagonist of the Human Luteinizing Hormone–Releasing Hormone (LHRH) Receptor", *J. Med. Chem.*, 1998, pp. 4190–4195, vol. 41(22).

Corbin, et al., "Inhibition of the Pre–Ovulatory Proestrous Gonadotropin Surge, Ovulation and Pregnancy with a Peptide Analogue of Luteinizing Hormone Releasing Hormone", *Endocr. Res. Commun.*, 1975, pp. 1–23, vol. 2.

(Continued)

*Primary Examiner*—Golam M. M. Shameem
(74) *Attorney, Agent, or Firm*—Keith D. Hutchinson; Bryan C. Zielinski

(57) ABSTRACT

Non-peptide GnRH agents capable of inhibiting the effect of gonadotropin-releasing hormone are described. Such compounds and their pharmaceutically acceptable salts, prodrugs, and active metabolites are suitable for treating mammalian reproductive disorders and steroid hormone-dependent tumors as well as for regulating fertility, where suppression of gonadotropin release is indicated. Methods for synthesizing the compounds and intermediates useful in their preparation are also described.

7 Claims, No Drawings

OTHER PUBLICATIONS

Dear, et al., "Mass Directed Peak Selection, An Efficient Method of Drug Metabolite Identification Using Directly Coupled Liquid Chromatography–Mass Spectrometry–Nuclear Magnetic Resonance Spectroscopy", *J. Chromatogr. B.*, 2000, pp. 281–293, vol. 748.

Goetz, "Research Letters: Decreased Recovery of CD4 Lymphocytes in Older HIV–infected Patients Beginning Highly Active Antiretroviral Therapy", *AIDS*, 2001, pp. 1576–1578, vol. 15.

Harms, et al. "A Rapid and Simple Procedure for Chronic Cannulation of the Rat Jugular Vein", *Applied Physiol*, 1974, pp. 391–392, vol. 36(3).

Jungwirth, et al., "Luteinizing Hormone–Releasing Hormone Antagonist Cetrorelix (SB–75) and Bombesin Antagonist RC–3940–II Inhibit the Growth of Androgen–Independent PC–3 Prostate Cancer in Nude Mice", *Prostate*, 1997, pp. 164–172, vol. 32(3).

Koppan, et al., "Targeted Cytotoxic Analog of Luteinizing Hormone–Releasing Hormone AN–207 Inhibits the Growth of PC–82 Human Prostate Cancer in Nude Mice", *Prostate*, 1999, pp. 151–158, vol. 38(2).

Kottler, et al., "The Genes for Gonadotropin–Releasing Hormone and Its Receptor and Expressed in Human Breast with Fibrocystic Disease and Cancer", *Int. J. Cancer*, 1997, pp. 595–599, vol. 71(4).

Larsen, "Design and Application of Prodrugs", *Drug Design and Development*, (1991, Krogsgaard–Larsen et al eds., Harwood Academic Publishers).

Montagnani, et al. "Effects of LHRH Agonists on the Growth of Human Prostatic Tumor Cells: 'In Vitro' and 'In Vivo' Studies", *Arch. Ital. Urol. Androl.*, 1997, pp. 257–263, vol. 69(4).

Nagy, et al., "Stability of Cytotoxic Luteinizing Hormone–Releasing Hormone Conjugate (AN–152) Containing Doxorubicin 14–O–Hemiglutarate in Mouse and Human Serum in Vitro: Implications for the Design of Preclinical Studies", *Proc Natl Acad Sci USA*, 2000, pp. 829–834, vol. 97(2).

Norwood Abbey Press Release dated Mar. 5, 2001; "Norwood Abbey Announces Breakthrough in Immunology".

Prox, et al., "Rapid Structure Elucidation of Drug Metabolites by Use of Stable Isotopes", *Xenobiol.*, 1992, pp. 103–112, vol. 3(2).

Shan, et al., "Prodrug Strategies Based on Intramolecular Cyclization Reactions", *J. Pharm. Sci.*, 1997, pp. 765–767, vol. 86(7).

Spraul, et al., "Liquid Chromatography Coupled with High–Field Proton NMR for Profiling Human Urine for Endogenous Compounds and Drug Metabolites", *J. Pharmaceutical & Biomedical Analysis*, 1992, pp. 601–605, vol. 10(8).

Srkalovic, et al., "Presence and Characteristics of Receptors for [D–Trp $^6$] Luteinizing Hormone Releasing Hormone and Epidermal Growth Factor in Human Ovarian Cancer", *Int. J. Oncol.*, 1998, pp. 489–498, vol. 12(3).

Still, et al., "Rapid Chromatographic Technique for Preparative Separations with Moderate Resolution", *A.J. Org. Chem.*, 1978, p. 2923, vol. 43.

Walsh, et al., "Potent Antagonists of Gonadotropin Releasing Hormone Receptors Derived from Quinolone–6–Carboxamides", *Bioorg & Med Chem Ltrs.*, 2000, pp. 443–447, vol. 10.

Wilt, et al., "Ring Size Effects in the Neophyl Rearrangement. II. The Decarbonylation of (1–Methylindanyl)acetaldehyde $^{1,2}$", *J. Org. Chem.*, 1961, p. 4196, vol. 26.

\* cited by examiner

NON-PEPTIDE GNRH AGENTS, PHARMACEUTICAL COMPOSITIONS AND METHODS FOR THEIR USE

RELATED APPLICATIONS

This application claims the benefit of U.S. Provisional Application No. 60/388,788, filed Jun. 13, 2002.

TECHNICAL FIELD AND INDUSTRIAL APPLICABILITY OF THE INVENTION

This invention relates generally to compounds that affect the action of human gonadotropin-releasing hormone (GnRH). More particularly, it relates to certain non-peptide GnRH antagonists or agonists and to their preparation. These non-peptide GnRH agents are useful medicaments for diseases or conditions mediated by modulation of the pituitary-gonadal axis. The invention also relates to methods for treating individuals needing therapeutic regulation of GnRH—i.e., methods for treating diseases and conditions mediated by GnRH regulation.

BACKGROUND OF THE INVENTION

Gonadotropin-Releasing Hormone (GnRH), also known as luteinizing hormone-releasing hormone (LH-RH), plays a central role in the biology of reproduction. Various analogs have been used for an increasing number of clinical indications. The GnRH decapeptide (pyro-Glu-His-Trp-Ser-Tyr-Gly-Leu-Arg-Pro-Gly-$NH_2$ or p-EHWSYGLRPG-$NH_2$) is produced in neurons of the medial basal hypothalamus from a larger precursor by enzymatic processing. The decapeptide is released in a pulsatile manner into the pituitary portal circulation system where GnRH interacts with high-affinity receptors (7-Transmembrane G-Protein Coupled Receptors) in the anterior pituitary gland located at the base of the brain. In the pituitary, GnRH triggers the release of two gonadotropic hormones (gonadotropins): luteinizing hormone (LH) and follicle-stimulating hormone (FSH). In testes and ovaries, LH stimulates the production of testosterone and estradiol, respectively. FSH stimulates follicle growth in women and sperm formation in men. When correctly functioning, the pulse-timed release and concentration levels of GnRH are critical for the maintenance of gonadal steroidogenesis and for normal functions of reproduction related to growth and sexual development.

The pituitary response to GnRH varies greatly throughout life. GnRH and the gonadotropins first appear in the fetus at about ten weeks of gestation. The sensitivity to GnRH declines, after a brief rise during the first three months after birth, until the onset of puberty. Before puberty, the FSH response to GnRH is greater than that of LH. Once puberty begins, sensitivity to GnRH increases, and pulsatile LH secretion ensues. Later in puberty and throughout the reproductive years, pulsatile release of GnRH occurs throughout the day, with LH responsiveness being greater than that of FSH. Pulsatile GnRH release results in pulsatile LH and FSH release from the pituitary and, hence, estosterone and estradiol release from the gonads. After menopause, FSH and LH concentrations rise, and post-menopausal FSH levels are higher than those of LH.

Chronic administration of GnRH agonists and antagonists to animals or to man results in decreased circulating levels of both LH and FSH. GnRH agonists are compounds that mimic endogenous GnRH to stimulate receptors on the pituitary gland, resulting in release of LH and FSH. After a transient rise in gonadal hormone production or "flare" response, chronic administration of GnRH agonists results in a down-regulation of GnRH receptors. GnRH receptor down-regulation and desensitization of the pituitary results in a decrease of circulating levels of LH and FSH. In spite of the symptom-exacerbating hormonal flare experienced, GnRH agonists have been the treatment of choice for sex-steroid-dependent pathophysiologies. For example, GnRH agonists have been used to reduce testosterone production, thereby reducing prostate volume in benign prostatic hyperplasia (BPH) and slowing tumor growth in prostate cancer. These compounds have also been used to treat breast and-ovarian cancers.

Recently, GnRH antagonists have become available for clinical evaluation. GnRH antagonists have an immediate effect on the pituitary without the observed flare associated with agonists. Use of GnRH antagonists (e.g., decapeptides) has been reported in the literature for treatment of breast, ovarian, and prostatic cancers. Other uses of antagonists, like agonists, include endometriosis (including endometriosis with pain), uterine myoma, ovarian and mammary cystic diseases (including polycystic ovarian disease), prostatic hypertrophy, amenorrhea (e.g., secondary amenorrhea), unterine fibroids, and precocious puberty. These compounds may also be useful in the symptomatic relief of premenstrual syndrome (PMS), pregnancy regulation, infertility remedy or menstration regulation. Furthermore, antagonists may be useful to regulate the secretion of gonadotropins in male mammals to arrest spermatogenesis (e.g., as male contraceptives), and for treatment of male sex offenders. Importantly, GnRH antagonists (and agonists) have found utility in treatments where a reversible suppression of the pituitary-gonadal axis is desired and in the treatment of sleep disorders (e.g., apnea).

For over fifty years, androgen deprivation has been the most effective systematic therapy for the treatment of metastatic carcinoma of the prostate. The rationale is simple—the prostate gland requires androgens for proper growth, maintenance, and function. Yet, prostate cancer and benign prostate hyperplasia are common in men and develop in an environment of continuous androgen exposure. Thus, utilizing a GnRH antagonist to interrupt the pituitary-gonadal axis reduces androgen production and results in tumor growth modulation. Furthermore, GnRH antagonists may have a direct effect on tumor growth by blocking receptors on the tumor cells. For those cancer types that respond both to sex hormones and to GnRH directly, antagonists should be effective in slowing tumor growth by these two mechanisms. Since GnRH receptors are present on many prostate and breast cancer cells, it has recently been speculated that GnRH antagonists may also be effective in treating non-hormone-dependent tumors. Recent literature examples indicate that GnRH receptors are present on a number of cancer cell lines, including:

prostate cancer: GnRH agonists exert both in vitro, and in vivo, a direct inhibitory action on the growth of both androgen-dependent (LNCaP) and androgen-independent (DU 145) human prostatic cancer cell lines [Montagnani et al., *Arch. Ital. Urol. Androl.*, 69(4), 257–263 (1997); Jungwirth et al., "GnRH Antagonist Inhibit the Growth of Androgen-independent PC-3 Prostate Cancer in Nude Mice," *Prostate*, 32(3), 164–172 (1997)];

ovarian cancer: The demonstration of GnRH receptors in human ovarian cancers provides a rationale for the use of therapeutic approaches based on GnRH analogues in this malignancy [Srkalovic et al., *Int. J. Oncol.*, 12(3), 489–498 (1998)].

breast cancer: Breast cancer is the most common type of cancer in women over the age of forty and is the leading cause of cancer-related death in women. Systematic endocrine intervention represents a major treatment option for the management of advanced breast cancer, especially with estrogen-dependent cancers. The genes for gonadotropin-releasing hormone and its receptor are expressed in human breast with fibrocystic disease and cancer [Kottler et al., *Int. J. Cancer*, 71(4), 595–599 (1997)].

GnRH agents may also be useful in treating cancer through generation of thymus re-growth and therefore induction of the development of new T-cells. See Norwood Abbey press release dated Mar. 5, 2001; Norwood Abbey Announces Breakthrough In Immunology. These white blood cells, which develop in the thymus gland, are a fundamental component of the immune system's involvement in a range of diseases, including viral infections, transplant organ rejection, cancer, and autoimmune diseases. Thus, for example, since the human immunodeficiency virus (HIV) preferentially infects and destroys T-cells, GnRH agents may be useful for treating HIV infection or acquired immune deficiency syndrome (AIDS). Additionally, GnRH agents may be useful in combating infection in tissue-transplant patients where immunosuppressive drugs, which remove T-cells, are being administered to counteract rejection of the transplanted tissue. Similarly, since adequate and effective T-cells help defend against cancer, and chemotherapy and radiation regimens detrimentally impact T-cells, GnRH agents may be useful in conjunction with a chemotherapeutic agent or radiation regimin in treating cancer. Furthermore, GnRH agents may be useful for treating autoimmune diseases such as multiple sclerosis (MS), where T-cells are produced that react against a molecule surrounding nerve cells.

GnRH agents may also benefit patients who have been shown to have a decreased likelihood of immune recovery with HAART. See *AIDS*. 2001; 15:1576–1578.

Heretofore, available GnRH antagonists have included peptide analogs of GnRH. See, e.g., International Publication Nos. WO 93/03058, WO 99/50276, WO 00/12521, and WO 00/12522; Koppan et al., *Prostate*, 38(2), 151–8 (1999); and Nagy et al., *Proc Natl Acad Sci USA*, 97(2),829–34 (2000). Though peptide antagonists of peptide hormones are often quite potent, the use of peptide antagonists is typically associated with problems because peptides are degraded by physiological enzymes and often poorly distributed within the organism being treated.

The first non-peptide antagonist of the human leuteinizing hormone-releasing hormone (LHRH) receptor was reported by Cho et al. (*J Med Chem*, 41(22), 4190 (1998)). Since then, other non-peptide GnRH antagonists have been reported in the literature. For example, certain quinolone-6-carboxamides were reported by Walsh et al. in *Bioorg & Med Chem Ltrs.*, 10, 443–447 (2000). Certain tricyclic diazepines and cyclic pentapeptides were reported in International Publication Nos. WO 96/38438 and WO 96/34012, respectively. Certain tetrahydroisoquinoline derivatives were reported in U.S. Pat. No. 5,981,521. For additional examples of non-peptide GnRH antagonists, see International Publication Nos. WO 97/21435, WO 97/21703, WO 97/21704, WO 97/21707, WO 99/44987, WO 00/04013, WO 00/12522, WO 00/12521, WO 00/04013, WO 00/68959, WO 01/29044 and WO 00/20358.

Despite recent advances, there continues to be a need for non-peptide antagonists of the peptide hormone GnRH with desirable properties. For example, there is a need for non-peptide GnRH agents having advantageous physical, chemical and biological properties, which are useful medicaments for treating diseases mediated via the pituitary-gonadal axis and by directly targeting the receptor on tumor cells. Furthermore, there is a need for non-peptide GnRH agents having desirable activity, solubility, and/or metabolic properties. There is also a need for GnRH agents that act upon these receptors to treat both hormone-dependent and hormone-independent cancers.

SUMMARY OF THE INVENTION

In one general aspect, the invention is directed to compounds represented by the following Formula I:

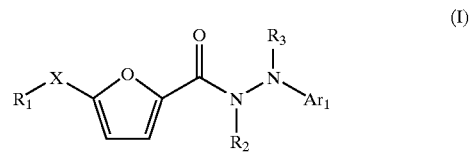

wherein:

$R_1$ is selected from the group consisting of $C_3$–$C_{10}$ alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group unsubstituted or substituted with one or more substituents independently selected from the group consisting of: halogens; =O; =S; —CN; and —$NO_2$; and alkyl, alkenyl, heteroalkyl, haloalkyl, alkynyl, aryl, cycloalkyl, heterocycloalkyl, heteroaryl, —$(CH_2)_z$CN where z is an integer from 0 to 4, =NH, —NHOH, —OH, —C(O)H, —OC(O)H, —C(O)OH, —OC(O)OH, —OC(O)OC(O)H, —OOH, —C(NH)$NH_2$, —NHC(NH)$NH_2$, —C(S)$NH_2$, —NHC(S)$NH_2$, —NHC(O)$NH_2$, —S($O_2$)H, —S(O)H, —$NH_2$, —C(O)$NH_2$, —OC(O)$NH_2$, —NHC(O)H, —NHC(O)OH, —C(O)NHC(O)H, —OS($O_2$)H, —OS(O)H, —OSH, —SC(O)H, —S(O)C(O)OH, —$SO_2$C(O)OH, —NHSH, —NHS(O)H, —$NHSO_2$H, —C(O)SH, —C(O)S(O)H, —C(O)S($O_2$)H, —C(S)H, —C(S)OH, —C(SO)OH, —C($SO_2$)OH, —NHC(S)H, —OC(S)H, —OC(S)OH, —OC($SO_2$)H, —S($O_2$)$NH_2$, —S(O)$NH_2$, —$SNH_2$, —NHCS($O_2$)H, —NHC(SO)H, —NHC(S)H, and —SH groups unsubstituted or substituted with one or more substituents selected from the group consisting of halogens, =O, —$NO_2$, —CN, —$(CH_2)_z$—CN where z is an integer from 0 to 4, —$OR_c$, —$NR_cOR_c$, —$NR_cR_c$, —C(O)$NR_c$, —C(O)$OR_c$, —C(O)$R_c$, —$NR_cC(O)NR_cR_c$, —$NR_cC(O)R_c$, —OC(O)$OR_c$, —OC(O)$NR_cR_c$, —$SR_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group;

X is selected from the group consisting of: C($A_1$)($A_2$) wherein $A_1$ and $A_2$ are each independently hydrogen, or an unsubstituted alkyl, heteroalkyl, aryl, heteroaryl, cycloalkyl, heterocycloalkyl, or haloalkyl group; N($A_3$) wherein $A_3$ is hydrogen or an unsbstituted alkyl, heteroalkyl, aryl, heteroaryl, cycloalkyl, heterocycloalkyl, or haloalkyl group; O; S; SO; and $SO_2$;

$R_2$ is hydrogen or an unsubstituted alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group;

$R_3$ is hydrogen or an unsubstituted alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group; and $Ar_1$ is selected from the group consisting of aryl, cycloalkyl, heterocycloalkyl, and heteroaryl groups unsubstituted or substituted with one or more substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)H, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

Preferably, $R_1$ is selected from the group consisting of aryl, cycloalkyl, heterocycloalkyl, and —O-aryl groups unsubstituted or substituted with one or more substitutents independently selected from the group consisting of: halogens, =O, alkyl, heteroalkyl, aryl, cycloalkyl, —OH, —C(O)H, and —C(O)NH$_2$ groups unsubstituted or substituted with one or more substitutents selected from the group consisting of —C(O)NR$_c$, unsubstituted alkyl, unsubstitued aryl, and unsubstituted cycloalkyl, where R$_c$ is hydrogen or unsubstituted alkyl; X is CH$_2$ or O; $R_2$ is hydrogen; $R_3$ is hydrogen or alkyl; $Ar_1$ is an aryl or heteroaryl group unsubstituted or substituted with one or more substituents independently selected from the group consisting of: halogens; and alkyl, heteroalkyl, haloalkyl, cycloalkyl, —OH, —NH$_2$, and —S(O)NH$_2$ groups unsubstituted or substituted with one or more substitutents selected from the group consisting of unsubstituted alkyl, unsubstituted cycloalkyl, and unsubstituted heterocycloalkyl.

In another general aspect, the invention is directed to compounds represented by the following Formula II:

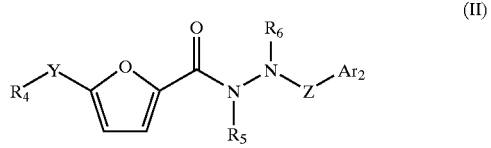

wherein:

$R_4$ is selected from the group consisting of $C_3$–$C_{10}$ alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group unsubstituted or substituted with one or more substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group;

Y is selected from the group consisting of $C(A_4)(A_5)$ wherein $A_4$ and $A_5$ are each independently selected from the group consisting of hydrogen, alkyl, heteroalkyl, aryl, heteroaryl, cycloalkyl, heterocycloalkyl, and haloalkyl; $N(A_6)$ wherein $A_6$ is hydrogen, alkyl, heteroalkyl, aryl, heteroaryl, cycloalkyl, heterocycloalkyl, or haloalkyl; S; SO; and SO$_2$;

$R_5$ is hydrogen or an unsubstituted alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group;

$R_6$ is hydrogen or an unsubstituted alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group;

Z is selected from the group consisting of: $C(A_7)(A_8)$ wherein $A_7$ and $A_8$ are each independently selected from the group consisting of hydrogen, alkyl, heteroalkyl, aryl, heteroaryl, cycloalkyl, heterocycloalkyl, and haloalkyl; N(A$_9$) wherein A$_9$ is hydrogen, alkyl, heteroalkyl, aryl, heteroaryl, cycloalkyl, heterocycloalkyl, or haloalkyl; and S; and Ar$_2$ is selected from the group consisting of aryl, cycloalkyl, heterocycloalkyl, and heteroaryl groups unsubstituted or substituted with one or more substituents independently from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents selected from the group consisting of halogens, =O, —NO$_2$, —CN, —(CH$_2$)$_z$—CN where z is an integer from 0 to 4, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SR$_c$, unsubstituted alkyl, unsubstituted alkenyl, unsubstituted alkynyl, unsubstituted aryl, unsubstituted cycloalkyl unsubstituted heterocycloalkyl, and unsubstituted heteroaryl, where R$_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$_c$ groups together cyclize to form part of a heteroaryl or heterocycloalkyl group unsubstituted or substituted with an unsubstituted alkyl group.

Preferably, R$_4$ is selected from the group consisting of aryl, cycloalkyl, heterocycloalkyl, and —O-aryl groups unsubstituted or substituted with one or more substitutents independently selected from the group consisting of: halogens, =O, alkyl, heteroalkyl, aryl, cycloalkyl, —OH, —C(O)H, and —C(O)NH$_2$ groups unsubstituted or substituted with one or more substituents selected from the group consisting of —C(O)NR$_c$, unsubstituted alkyl, unsubstitued aryl, and unsubstituted cycloalkyl, where R$_c$ is hydrogen or unsubstituted alkyl; Y is CH$_2$ or O; R$_5$ is hydrogen and R$_6$ is hydrogen or alkyl; Ar$_2$ is an aryl or heteroaryl group unsubstituted or substituted with one or more substituents independently selected from the group consisting of: halogens; and alkyl, heteroalkyl, haloalkyl, cycloalkyl, —OH, —NH$_2$, and —S(O)NH$_2$ groups unsubstituted or substituted with one or more substitutents selected from the group consisting of unsubstituted alkyl, unsubstituted cycloalkyl, and unsubstituted heterocycloalkyl.

In addition to compounds of Formula I and II, the invention is also directed to pharmaceutically acceptable salts, pharmaceutically acceptable prodrugs, and pharmaceutically active metabolites of such compounds, and pharmaceutically acceptable salts of such metabolites. Such compounds, salts, prodrugs and metabolites are at times collectively referred to herein as "GnRH agents."

The invention also relates to pharmaceutical compositions each comprising a therapeutically effective amount of a GnRH agent of the invention in combination with a pharmaceutically acceptable carrier or diluent. Moreover, the invention relates to methods for regulating the secretion of gonadotropins in mammals, comprising administering therapeutically effective amounts of GnRH agents of the invention.

Other aspects, features, and advantages of the invention will become apparent from the detailed description of the invention and its preferred embodiments.

DETAILED DESCRIPTION OF INVENTION AND PREFERRED EMBODIMENTS

As used herein, the terms "comprising" and "including" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by "/"), ethyl (Et), n-propyl, isopropyl, butyl, isobutyl, sec-butyl, tert-butyl (tBu), pentyl, isopentyl, tert-pentyl, hexyl, isohexyl, and the like.

The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary alkyl amines, alkyl sulfides, and the like.

The term "alkenyl" refers to a straight- or branched-chain alkenyl group having from 2 to 12 carbon atoms in the chain. Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. Illustrative alkynyl groups include prop-2-ynyl, but-2-ynyl, but-3-ynyl, 2-methylbut-2-ynyl, hex-2-ynyl, and the like.

The term "haloalkyl" refers to a straight- or branched-chain alkenyl group having from 2–12 carbon atoms in the chain and where one or more hydrogens is substituted with a halogen. Illustrative haloalkyl groups include trifluoromethyl, 2-bromopropyl, 3-chlorohexyl, 1-iodo-isobutyl, and the like.

The term "aryl" (Ar) refers to a monocyclic, or fused or spiro polycyclic, aromatic carbocycle (ring structure having ring atoms that are all carbon) having from 3 to 12 ring atoms per ring. Illustrative examples of aryl groups include the following moieties:

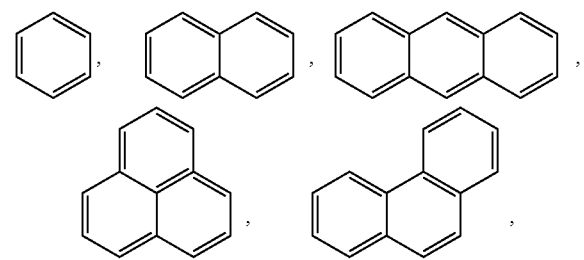

and the like.

The term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

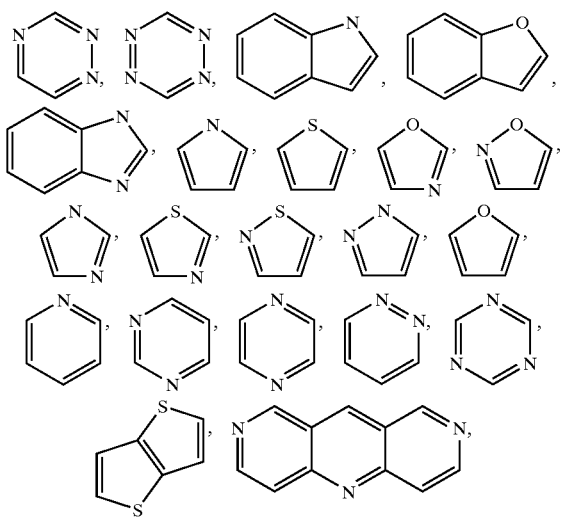

and the like.

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

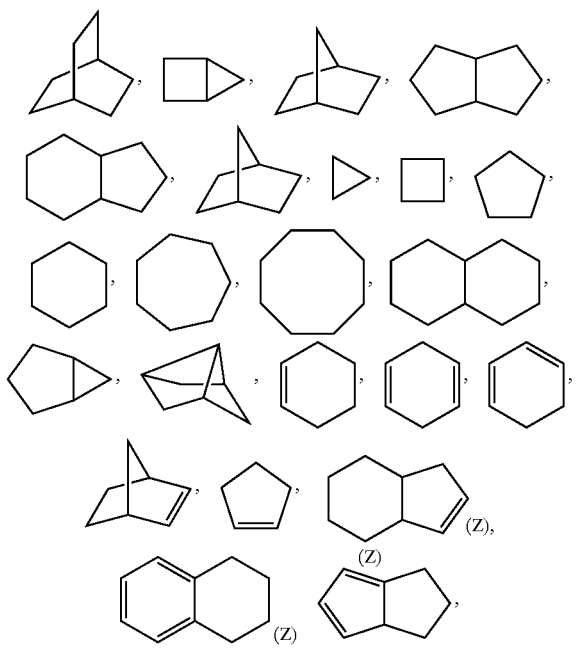

and the like.

A "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

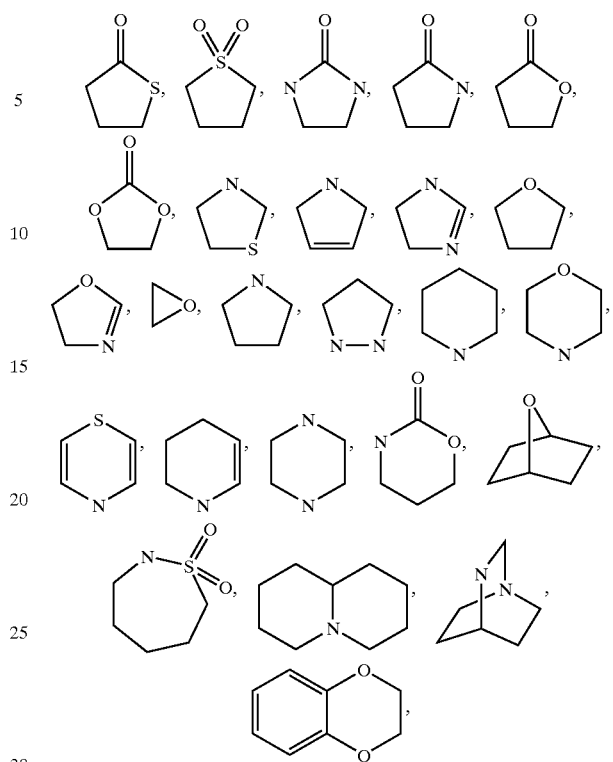

and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents.

Preferred GnRH agents of the invention include those having a $K_i$ value of about 10 $\mu$M or less. Especially preferred GnRH agents are those having a $K_i$ value of about 10 nM or less.

Preferred compounds of the invention include the examples described further below.

It is understood that while a compound may exhibit the phenomenon of tautomerism, the formula drawings within this specification expressly depict only one of the possible tautomeric forms. It is therefore to be understood that a formula is intended to represent any tautomeric form of the depicted compound and is not to be limited merely to a specific compound form depicted by the structural formula.

It is also understood that a compound of Formula I may exist as an "E" or "Z" configurational isomer, or a mixture of E and Z isomers. It is therefore to be understood that a formula is intended to represent any configurational form of the depicted compound and is not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. In one preferred embodiment, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

As indicated above, GnRH agents in accordance with the invention also include active tautomeric and stereoisomeric forms of the compounds of Formula I, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, Formula I is intended to cover, where applicable, solvated as well as unsolvated forms of the compounds. Thus, each formula includes compounds having the indicated structure, including the hydrated as well as the non-hydrated forms.

In addition to compounds of the Formula I, the GnRH agents of the invention include pharmaceutically acceptable salts, prodrugs, and active metabolites of such compounds, and pharmaceutically acceptable salts of such metabolites. A "pharmaceutically active metabolite" is a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86(7), 765–767 (1997); Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); Larsen, *Design and Application of Prodrugs*, Drug Design and Development (Krogsgaard-Larsen et al. eds., Harwood Academic Publishers, 1991); Dear et al., *J. Chromatogr. B*, 748, 281–293 (2000); Spraul et al., *J. Pharmaceutical & Biomedical Analysis*, 10(8), 601–605 (1992); and Prox et al., *Xenobiol.*, 3(2), 103–112 (1992).

The term "pharmaceutically acceptable salts" refers to salt forms that are pharmacologically acceptable and substantially non-toxic to the subject being administered the GnRH agent. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

A variety of known assays and techniques may be employed to determine the level of activity of various forms of the compounds in the GnRH system. Ligand-binding assays are used to determine interaction with the receptor of interest. Where binding is of interest, a labeled receptor may be used, where the label is a fluorescer, enzyme, radioisotope, or the like, which registers a quantifiable change upon the binding of the receptor. Alternatively, the artisan may provide for an antibody to the receptor, where the antibody is labeled, which may allow for amplification of the signal. Binding may also be determined by competitive displacement of a ligand bound to the receptor, where the ligand is labeled with a detectable label. Where agonist and/or antagonist activity is of interest, an intact organism or cell may be studied, and the change in an organismic or cellular function in response to the binding of the compound of interest may be measured. Various devices are available for detecting cellular response, such as a microphysiometer available from Molecular-Devices, Redwood City, Calif. In vitro and in vivo assays useful in measuring GnRH antagonist activity are known in the art. See, e.g., Bowers et al., "LH suppression in cultured rat pituitary cells treated with 1 ng of LHRH," *Endocrinology*, 1980, 106:675–683 (in vitro,) and Corbin et al., "Antiovulatory activity (AOA) in rats," *Endocr. Res. Commun.*, 2:1–23 1975. Particular test protocols that may be used are described below.

For example, GnRH-receptor antagonists may be functionally assessed by measurement of change in extracellular acidification rates as follows. The ability of compounds to block the extracellular rate of acidification mediated by GnRH in HEK 293 cells expressing human GnRH receptors is determined as a measure of the compound's antagonist activity in vitro. Approximately 100,000 cells/chamber are immobilized in agarose suspension medium (Molecular Devices) and perfused with unbuffered MEM media utilizing the Cytosensoro® Microphysiometer (Molecular Devices). Cells are allowed to equilibrate until the basal acidification rate remains stable (approximately one hour). Control dose-response curves are performed to GnRH ($10^{-11}$ M to $10^{-7}$ M). Compounds are allowed to incubate 15 minutes prior to stimulation with GnRH, and are assessed for antagonist activity. After incubation with test compounds, repeat dose-response curves to GnRH in the presence or absence of various concentrations of the test compounds are obtained. Schild regression analysis is performed on compounds to determine whether compounds antagonize GnRH-mediated increases in extracellular acidification rates through a competitive interaction with the GnRH receptor.

In another test, accumulation of total inositol phosphates may be measured by formic acid extraction from cells, followed by separation of the phosphates on Dowex columns. Cells are split using trypsin into two 12-well plates and pre-labeled with $^3$H-myoinositol (0.5 Ci to 2 mCi per mL) for 16–18 hours in inositol-free medium. The medium is then aspirated and the cells rinsed with either 1×HBSS, 20 mM HEPES (pH 7.5), or serum-free DMEM, 1×HBSS, 20 mM HEPES (pH 7.5) containing test compound, and 20 mM LiCl is then added and the cells are incubated for the desired time. The medium is aspirated and the reaction stopped by addition of ice-cold 10 mM formic acid, which also serves to extract cellular lipids. Inositol phosphates are separated by ion-exchange chromatography on Dowex columns, which are then washed with 5 mL of 10 mM myoinositol and 10 mM formic acid. The columns are then washed with 10 mL of 60 mM sodium formate and 5 mM borax, and total inositol phosphates are eluted with 4.5 mL 1M ammonium formate, 0.1M formic acid.

It will be appreciated that the actual dosages of the agents of this invention will vary according to the particular agent being used, the particular composition formulated, the mode of administration, and the particular site, host, and disease being treated. Optimal dosages for a given set of conditions may be ascertained by those skilled in the art using conventional dosage-determination tests in view of the experimental data for a given compound. For oral administration, an exemplary daily dose generally employed will be from about 0.001 to about 1000 mg/kg of body weight, with courses of treatment repeated at appropriate intervals. Administration of prodrugs may be dosed at weight levels that are chemically equivalent to the weight levels of the fully active compounds.

To treat diseases or conditions mediated by GnRH agonism or antagonism, a pharmaceutical composition of the invention is administered in a suitable formulation prepared by combining a therapeutically effective amount (i.e., a GnRH modulating, regulating, or inhibiting amount effective to achieve therapeutic efficacy) of at least one GnRH agent of the invention (as an active ingredient) with one or more pharmaceutically suitable carriers, which may be selected from diluents, excipients and auxiliaries that facilitate processing of the active compounds into the final pharmaceutical preparations. Optionally, one or more additional active ingredients, such as a second GnRH agent, may be employed in a pharmaceutical composition according to the invention.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methyl cellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation was tableted, placed in a hard gelatin capsule in powder or pellet form or in the form of a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of an inventive agent may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration chosen. For injection, the agents of the invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds was formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use was obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which was used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include. fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioabailability of poorly-soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®), Plurol®, Peceol® Transcutol® and the like may be used. Further, the pharmaceutical composition may be incorporated into a skin patch for delivery of the drug directly onto the skin.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

Synthesis of GnRH Reagents and Compounds

The inventive agents may be prepared using the reaction routes and synthesis schemes as described below, employing the techniques available in the art using starting materials that are readily available. The preparation of preferred compounds of the present invention is described in detail in the following examples, but the artisan will recognize that the chemical reactions described may be readily adapted to prepare a number of other GnRH agents of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

Reagents useful for synthesizing compounds may be obtained or prepared according to techniques known in the art. For example, the preparation of free amines from common salt forms and stock reagent solutions was useful for small-scale reactions. See also Abdel-Magid et al., "Reductive Amination of Aldehydes and Ketones with Sodium Triacetoxyborohydride," *J. Org. Chem.* 61: 3849 (1996).

Methanolic solutions of the free bases was prepared from hydrochloride, dihydrochloride, hydrobromide, or other salts when the free base is soluble in methanol. In this procedure, once the sodium methoxide is added, care should be taken to prevent exposure to air, since amine free bases, particularly primary amines, absorb carbon dioxide from the air to form salts. A 10-mL quantity of a 0.1M solution of a free base in methanol may be prepared as follows. Weigh 1.0 mmol of a monohydrochloride salt into a tared Erlenmeyer flask containing a stirring bar, and add 7 mL of methanol. To the stirred slurry, add 229 mL (1.0 mmol, 1 equiv.) of sodium methoxide in methanol (25 wt %, 4.37 M), stopper the flask, and stir the mixture vigorously for 2 hours. The slurry will sometimes change in appearance as a finer, milky precipitate of sodium chloride is formed. Filter the slurry through a 15-mL medium fritted glass funnel, wash the filter case with 1–2 mL methanol, transfer the filtrate to a 20-mL vial, and dilute to 10 mL with methanol. The theoretical yield of sodium chloride is nearly 59 mg, but the recovery is usually not quantitative, owing to a slight solubility in methanol. For a dihydrochloride salt, a second equivalent of sodium methoxide is required (458 mL).

A 0.5 M solution of sodium borohydride in ethanol may be prepared as follows. Sodium borohydride (520 mg, 13.8 mmol) is stirred in pure (non-denatured) anhydrous ethanol (25 mL) for ~2–3 minutes. The suspension is filtered through a medium frifted glass funnel to remove a small amount of undissolved solid (typically about 5% of the total mass of borohydride, or 25 mg). The filtrate should appear as a colorless solution that evolves only a little hydrogen. This solution should be used immediately, as it decomposes significantly over a period of a few hours, resulting in the formation of a gelatinous precipitate. Sodium borohydride is hygroscopic, so avoid exposure to air by making the solution at once after weighing the solid. Sodium borohydride has a solubility of about 4% in ethanol at room temperature. This corresponds to a little over 0.8 M. However, sometimes a small percentage of the solid remains undissolved regardless of the concentration being prepared, even after stirring for $\geq 5$ minutes.

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal® bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60° F. 254 plates (Analtech (0.25 mm)) and eluted with the appropriate solvent ratios (v/v). The reactions were assayed by TLC and terminated as judged by the consumption of starting material.

The TLC plates were visualized by UV absorption or with a ρ-anisaldehyde spray reagent or a phosphomolybdic acid reagent (Aldrich Chemical, 20 wt % in ethanol) which was activated with heat. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous $Na_2SO_4$ prior to filtration, and evaporation of the solvents was under reduced pressure on a rotary evaporator and noted as solvents removed in vacuo. Flash column chromatography [Still et al., *A.J. Org. Chem.* 43:2923 (1978)] was conducted using Baker-grade flash silica gel (47–61 mm) and a silica gel: crude material ratio of about 20:1 to 50:1, unless otherwise stated. Hydrogenolysis was done at the pressure indicated or at ambient pressure.

$^1$H-NMR spectra was recorded on a Bruker instrument operating at 300 MHz or 500 MHz, and $^{13}$C-NMR spectra was recorded operating at 75 MHz. NMR spectra are obtained as CDCl$_3$ solutions (reported in ppm), using chloroform as the reference standard (7.25 ppm and 77.00 ppm) or CD$_3$OD (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS or APCI. All melting points are uncorrected.

All final products had greater than 95% purity (by HPLC at wavelengths of 220 nm and 254 nm).

Additional compounds, other than those described below, may be prepared using the following described reaction schemes or appropriate variations or modifications thereof.

Scheme A

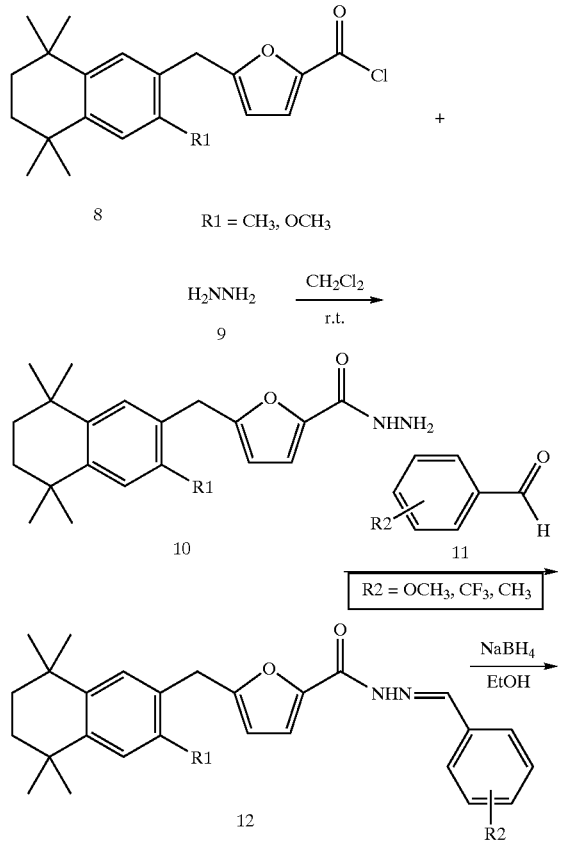

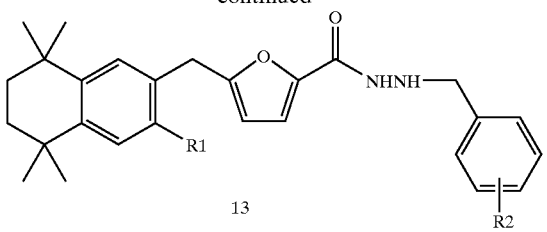

A solution of the acid chloride, 8, (1 mmol) in methylene chloride (5 mL) is added dropwise to anhydrous hydrazine, 9, (1 mL). The solution is stirred at room temperature overnight and then the reaction mixture is concentrated to an oily residue. The product, 10, is purified by silica gel chromatography, using as eluting solvent a mixture of ethyl acetate/methylene chloride (1/1). The hydrazide, 10, (1 mmol) is dissolved in ethanol (5 mL). To this solution is added the aldehyde component, 11, (1 mmol). The mixture is stirred at room temperature under argon atmosphere for 16 hours. The product imine, 12, is collected by filtration. An ethanolic solution (2 mL) containing sodium borohydride (10 mg) and the imine product, 12, from above (0.1 mmol) is stirred at room temperature overnight under argon. Water is added and the reaction mixture is then concentrated. The residue is dissolved in methylene chloride and the organic layer is ished with brine, then dried over magnesium sulfate and evaporated to a solid residue. The product is purified by silica gel chromatography eluting with a mixture of ethyl acetate/methylene chloride (1/1) to give compound 13. The overall unoptimized yields for the examples below were 28–30%.

Example A1

5-[(3,5,5,8,8-Pentamethyl-5,6,7,8-tetrahydro-2-naphthalenyl)methyl]-N'-(2,4,6-trimethoxybenzyl)-2-furohydrazide

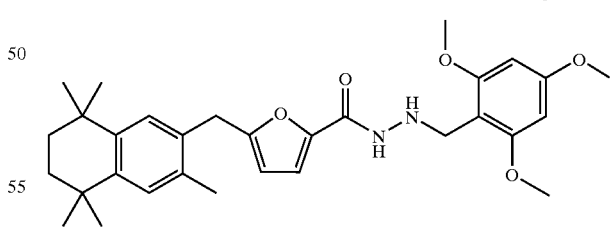

Compound A1 was synthesized according to Scheme A shown as described above wherein R1 was methyl and R2 was 2,4,6-methoxy. $^1$H NMR (300 MHz, CDCl$_3$): δ 1.20 (s, 6H), 1.28 (s, 6H), 1.70 (s, 4H), 2.24 (s, 3H), 3.75 (s, 6H), 3.80 (s, 3H), 3.89 (s, 2H), 4.08 (s, 2H), 5.0 (d, 1H), 6.11 (s, 2H), 7.04 (d, 1H), 7.06 (s, 1H), 7.12 (s, 1H), ESI-MS m/z 520.1 (M−H)$^-$.

The synthesis of compound 8 is outlined below:

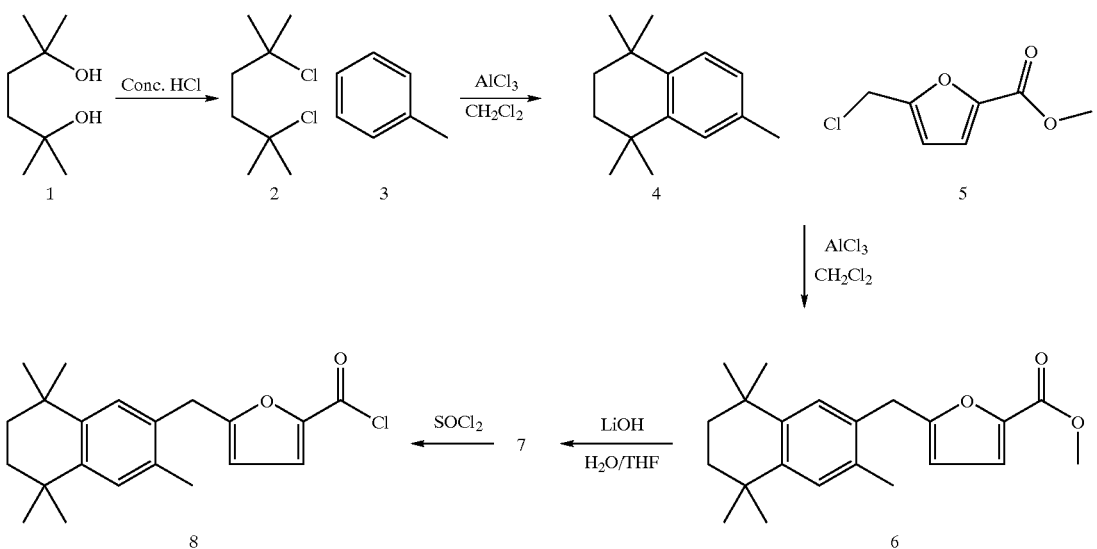

To a solution of 2,5 dichloro-2,5 dimethylhexane, 2, (10 g, 54.7 mmol) in toluene (270 mL 0.2 M) was slowly added aluminum trichloride (5.47 g, 41 mmol) as a solid over 15 minutes time. The reaction was complete after 10 minutes as assayed by TLC in hexanes. The unreacted aluminum trichloride was quenched slowly with water over 10 minutes. Additional toluene (250 mL) was added to extract the product from the aqueous layer. The organic layer was passed through a pad of silica gel (40 g) and eluted with toluene. The organic layer was evaporated in vacuo to dryness to yield 1,1,4,4,6-pentamethyl-1,2,3,4-tetrahydronaphtalene, 4 (11 g, 97% yield).

To a solution containing 1,1,4,4,6-pentamethyl-1,2,3,4-tetrahydronaphtalene, 4, (20 g, 99 mmol) and methyl 5-(chloromethyl)-2-furoate, 5, (17.28 g, 99 mmol) in methylene chloride (500 mL 0.2 M aluminum trichloride (16.46 g, 124 mmol) was added slowly as a solid at the reflux temperature. The solution was refluxed for an additional two hours. The reaction was monitored by TLC in 10% ethyl acetate/hexanes solution. The reaction was cooled to room temperature and the unreacted aluminum trichloride was quenched with water over 15 minutes. The crude product was extracted with methylene chloride and passed through silica gel (80 g) and eluted with methylene chloride. The solvent was evaporated in vacuo to syrup. The crude product was purified with silica gel (300 g) via a plug filteration column. Methyl 5-[(3,5,5,8,8-pentamethyl-5,6,7,8-tetrahydro-2-naphthalenyl) methyl]-2-furoate, 6, was eluted with 2% ethyl acetate/hexanes to afford 15.4 g (46% yield).

To a solution containing Methyl 5-[(3,5,5,8,8-pentamethyl-5,6,7,8-tetrahydro-2-naphthalenyl) methyl]-2-furoate, 6, (15.1 g, 44 mmol) in MeOH (175 mL) and water (175 mL), a solution of NaOH (3.53 g, 88.3 mmol) in water (29 mL) was added. The reaction was stirred overnight at room temperature. After completion as judged by TLC, the solution was acidified with 1 M HCl to pH 2. The crude product was extracted in to organic layer using ethyl acetate and concentrated to afford 5-[(3,5,5,8,8-pentamethyl-5,6,7,8-tetrahydro-2-naphthalenyl)methyl]-2-furoic acid, 7 (15.0 g, 99% yield).

To a solution containing 5-[(3,5,5,8,8-pentamethyl-5,6,7,8-tetrahydro-2-naphthalenyl)methyl]-2-furoic acid, 7, (20.15 g, 61.77 mmol) in methylene chloride (310 mL), thionyl chloride (45 mL, 617 mmol) was added. The reaction was heated under reflux for 5 hours and another batch of thionyl chloride (45 mL, 617 mmol) was added. The reaction was stirred overnight at room temperature. The solution was concentrated to a syrup and filtered through a pad of silica gel (50 g), eluted with 3% ethyl acetate in hexanes, and concentrated in vacuo to afford 5-[(3,5,5,8,8-pentamethyl-5,6,7,8-tetrahydro-2-naphthalenyl)methyl]-2-furoyl chloride, 8 (17 g, 80% yield).

Example A2

N'-(2,6-dimethoxybenzyl)-5-[(3,5,5,8,8-pentamethyl-5,6,7,8-tetrahydro-2-naphthalenyl) methyl-2-furohydrazide Compound A2

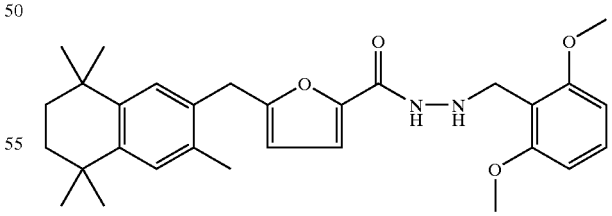

Compound A2 was synthesized by Scheme A shown above wherein R1 was methyl and R2 was 2,6-dimethoxy. $^1$H NMR (300 MHz, CDCl$_3$): δ 1.20 (s, 6H), 1.28 (s, 6H), 1.65 (s, 4H), 2.20 (s, 3H), 3.72 (s, 6H), 3.88 (s, 2H), 4.15 (s, 2H), 6.00 (d, 1H), 6.50 (d, 2H), 7.00 (s, 1H), 7.02 (d, 1H), 7.05 (s, 1H), 7.20 (t, 1H), APCI-MS m/z 491.2 (M+H)$^+$.

Scheme B

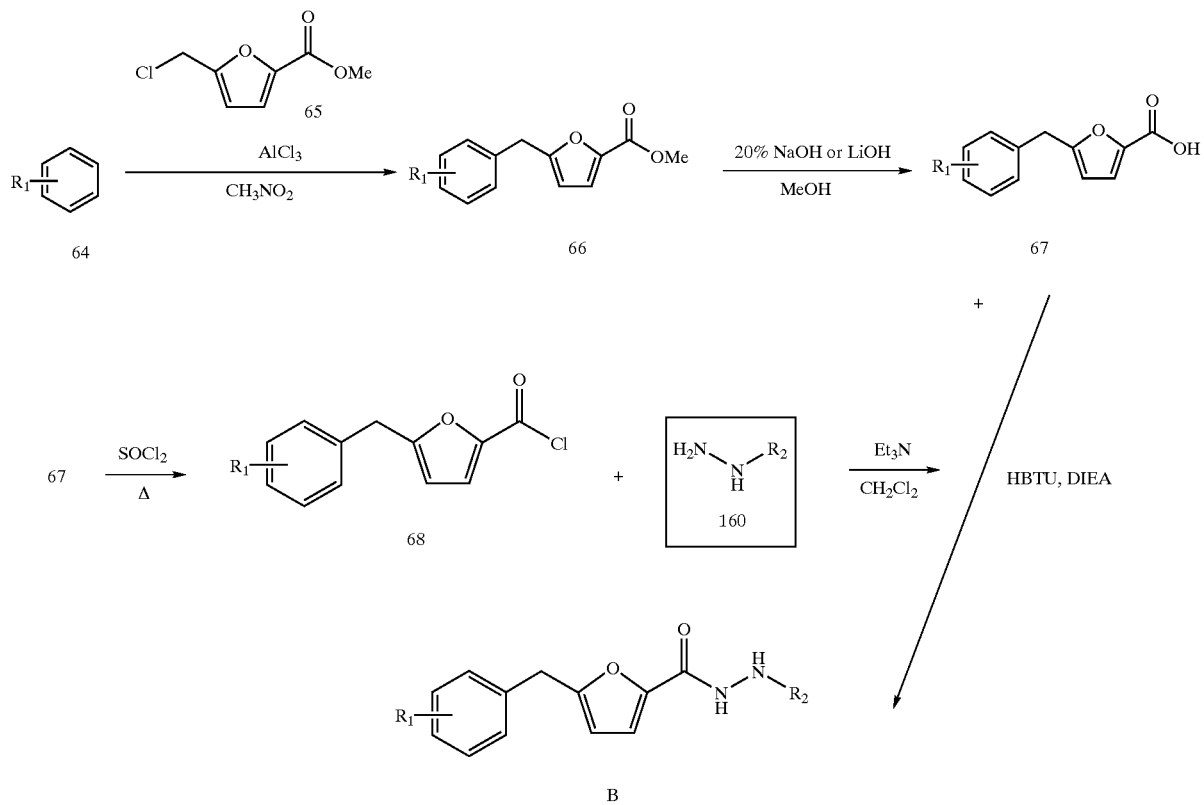

To a solution containing 64 (16.88 g, 97.75 mmol) and methyl 5-(chloromethyl)-2-furoate, 65, (14.22 g, 81.46 mmol) in nitromethane (300 mL, 0.3 M) is added slowly aluminum trichloride (9.56 g, 97.75 mmol). The solution is stirred at room temperature for 4 hours. The reaction is monitored by TLC in 10% ethyl acetate/hexanes solution. The unreacted aluminum trichloride is quenched with water (0° C.). The crude product is extracted with ethyl acetate. The separated organic layer is washed with brine, dried over magnesium sulfate and concentrated. The crude product is purified by silica gel chromatography elutes with hexane/ethyl acetate (19:1 v/v) to yield 66 (21.56 g, 85.8% yield).

To a solution of 66 in methanol (75 mL), a solution of 20% NaOH in water is added. The reaction mixture is stirred overnight. After completion as judged by TLC, the solution is washed with diethyl ether. The aqueous layer is acidified with 4N HCl to pH 2. The crude mixture is extracted with ethyl acetate, and concentrated to afford 67 (8.27 g, 86.66% yield). A solution of 67, is made in 10 mL thionyl chloride (SOCl$_2$). The reaction is heated to 100° C. for 30 minutes. The crude mixture is concentrated and co-evaporated with toluene to yield 1.05 g of 68.

Compound 68, (0.200 g, 0.639 mmol) in CH$_2$Cl$_2$ (0.3 M) is added to 160 (0.122 g, 0.639 mmol) in a flask. To this solution is added triethylamine (0.129 g, 1.277 mmol). Reaction is stirred at room temperature overnight. The crude product is purified by silica gel chromatography eluted with hexane/ethyl acetate (2:1) to yield B (42.6 mg, 14% yield).

Alternately, compounds may be synthesized by a coupling reaction between compound 67 and compound 160 using HBTU to give B. The procedure is as follows: To a solution of 67 (0.33 g, 1 mmol), HBTU (0.45 g, 1.2 mmol) in 10 mL DMF is added 0.5 ml Et$_3$N. The mixture is stirred at room temperature (rt.), for 30 minutes, compound 160, 1 mmol, is added to above solution, and the mixture is stirred overnight. fifty mL EtOAc is added and washed with water. Organic layer is dried with MgSO$_4$. Concentration gives crude product, which purified by HPLC. Additional compounds, other than those listed below, was prepared under these reaction conditions, using above Scheme B or variations or modifications thereof.

Additional compounds, other than those listed below, may be prepared under these reaction conditions, using above Scheme B or variations or modifications thereof.

Example B1

N'-[3,5-bis(trifluoromethyl)phenyl]-5-[(3,5,5,8,8-pentamethyl-5,6,7,8-tetrahydro-2-naphthalenyl)methyl]-2-furohydrazide Compound B1

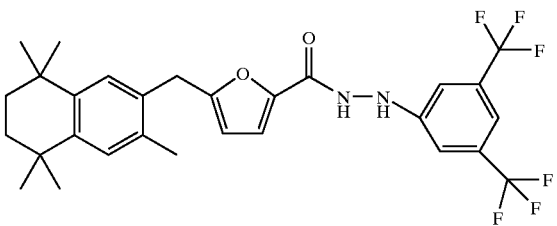

Compound B1 was synthesized by Scheme B shown above, wherein compound 64 was

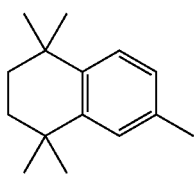

and compound 160 was

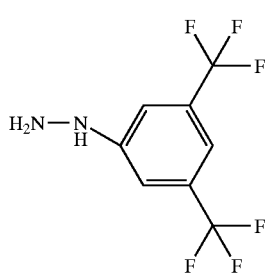

¹H NMR (300 MHz, CDCl₃): δ 1.32, 1.36 (2s, 6H each), 1.75 (s, 4H), 1.9 (br s, H₂O), 2.36 (s, 3H), 4.08 (s, 2H), 6.21 (d, 1H, J=3.4 Hz), 6.58 (br s, 1H), 7.13 (s, 1H), 7.20 (s, 1H), 7.26 (d, 1H, J=3.4 Hz), 7.36 (s, 1H), 7.47 (br s, 1H), 8.05 (br s, 1H), APCI-MS m/z 553.1 (M+H)⁺.

Example B2

N'-(3,5-dimethylphenyl)-5-[(3,5,5,8,8-pentamethyl-5,6,7,8-tetrahydro-2-naphthalenyl)methyl]-2furohydrazide Compound B2

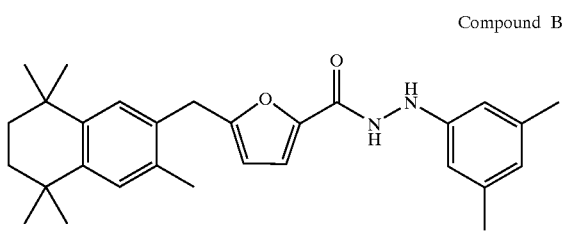

Compound B2 was synthesized according to Scheme B shown above wherein 64 was

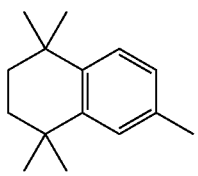

and compound 160 was

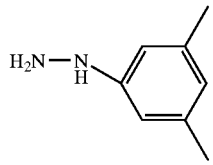

¹H NMR (300 MHz, CDCl₃) δ 1.24, 1.28 (2s, 6H each), 1.67 (s, 4H), 2.23 (s, 6H), 2.27 (s, 3H), 3.96 (s, 2H), 6.07 (d, 1H, J=3.4 Hz), 6.12 (br s, 1H), 6.51 (s, 2H), 6.55 (s, 1H), 7.04 (s, 1H), 7.11 (br s, 1H), 7.95 (s, 1H), APCI-MS m/z 445.2 (M+H)⁺.

Example B3

5-[5-(tert-butyl)-2-methylbenzyl]-N'-(2-quinolinyl)-2-furohydrazide

Compound B3

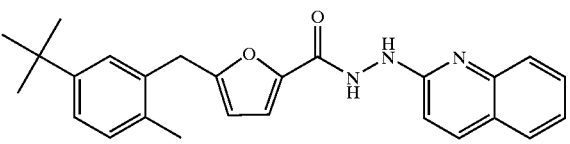

Compound B3 was synthesized according to scheme B wherein 64 was

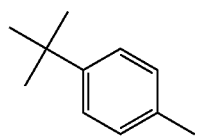

and compound 160 was

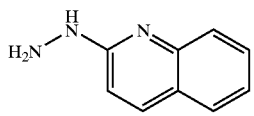

¹HNMR (300 MHz, CH₃OD): δ 1.28 (s, 9H), 2.27 (s, 3H), 4.10 (s, 2H), 6.13 (d, 1H), 7.10 (d, 1H), 7.20–7.5 (m, 4H), 7.58 (t,1H), 7.80–7.96 (m, 3H), 8.46 9d, 1H). ¹³CNMR (300 MHz, CH₃OD): δ 17.97, 30.78, 32.5, 34.1, 109.27, 111.04, 117.97, 118.32, 0.89, 124.21, 126.27, 126.48, 129.18, 130.24, 33.41, 134.59, 136.28, 144.60, 149.32, 155.11, 159.41, 160.10, APCI-MS m/z 414 (M+H)⁺.

Example C1

5-[(3,5,5,8,8-Pentamethyl-5,6,7,8-tetrahydro-2-naphthalenyl)methyl]-N'-(1,3,4-trimethyl-1H-pyrazolo[3,4-b]pyridin-6yl)-2-furohydrazide

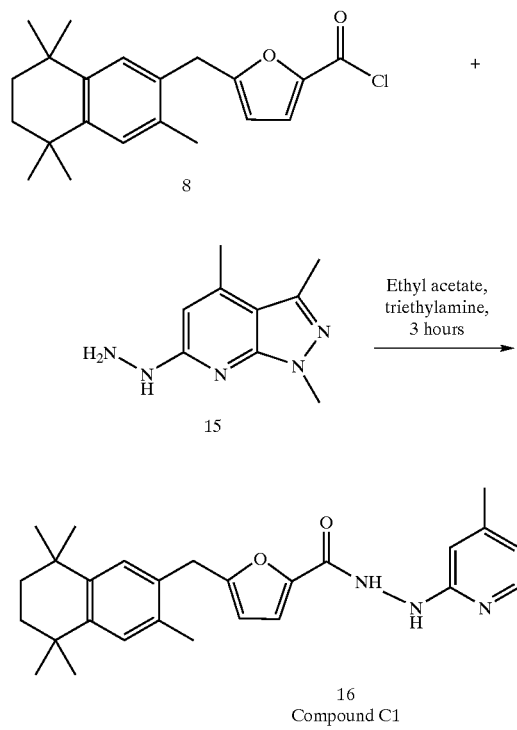

16
Compound C1

To a solution of 5-[(3,5,5,8,8-pentamethyl-5,6,7,8-tetrahydro-2-naphtholenyl) methyl]-2-furoyl chloride, 8, (1.0 eq, 2.9 mmol, 0.2 M) in ethyl acetate, 6-hydrazino-1,3,4-trimethyl-1H-pyrazolo [3,4-b]pyridine, 15, (3.0 eq, 8.7 mmol) was added. The solution was made basic with excess triethyl amine (6.0 eq, 17.4 mmol ) and allowed to stir over 3 hours. The solution was evaporated to dryness and dissolved in 50/50 DMSO/acetonitrile mixture. The cloudy solution was filtered and injected through the HPLC (method: 20–85% gradient acetonitrile/0.01 M aqueous ammonium acetate over 120 minutes) on a reverse phase column to afford 16, 5-[(3,5,5,8,8-pentamethyl-5-6,7,8-tetrahydro-2-naphthalenyl) methyl]-N'-(1,3,4-trimethyl-1H-pyrazolo [3,4-b]pyridin-6-yl)-2-furohydrazide (333 mgs, 23% yield). $^1$H NMR (300 MHz, CDCl$_3$): δ 7.15 (1H, d, J=3.4 Hz), 7.13 (1H, s), 7.07 (1H, s), 6.32 (1H, s), 6.12 (1H, d, J=3.4 Hz), 4.00 (2H, s), 3.92 (3H, s), 2.59 (3H, s), 2.57 (3H, s), 2.30 (3H, s), 1.68 (4H, s), 1.29 (6H,s), 1.27 (6H, s), APCI-MS m/z 499.3 (M+H)$^+$. Elemental analysis: calculated: C (72.12), H (7.46), N (14.02); actual: C (72.03), H (7.40), N (13.93).

Example C2

5-[(3-Methoxy-5,5,8,8-tetramethyl-5,6,7,8-tetrahydro-2-naphthalenyl)methyl]-N'-(1,3,4-trimethyl-1H-pyrazolo[3,4-b]pyridin-6-yl)-2-furohydrazide

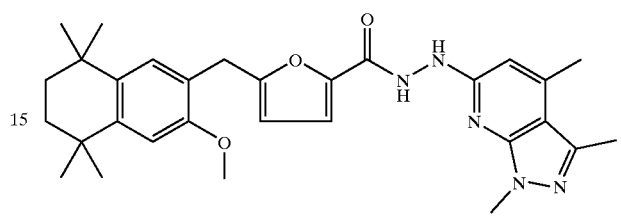

Compound C2

Compound C2 was made by the scheme described in Example C1 above, except using 5-[(5,5,8,8-tetramethyl-3-methoxy-5,6,7,8-tetrahydro-2-naphtholenyl) methyl]-2-furoyl chloride in place of starting reagent 8. Alternatively, Compound C2 can be synthesized from Compound C1, by exchanging the methyl at the 3-position on the naphthyl moiety for a methoxy (recovery 35%). $^1$H NMR (300 MHz, CDCl$_3$): δ 7.16 (1H, d, J=3.4 Hz) 6.16 (1H, d, J=3.4 Hz); 4.01 (2H, s); 3.92 (3H, s); 7.06 (1H, s); 6.80 (1H, s); 1.24 (6H, s); 1.31 (6H, s); 1.68 (4H, s); 6.33 (1H, s); 2.56 (3H, s); 2.58 (3H, s); 3.83 (3H, s), APCI-MS m/z 516.3 (M+H)$^+$.

Example C3

5-[(3-lsopropyl-5,5,8,8-tetramethyl-5,6,7,8-tetrahydro-2-naphthalenyl)methyl]-N'-(1,3,4-trimethyl-1H-pyrazolo[3,4-b]pyridin-6-yl)-2-furohydrazide

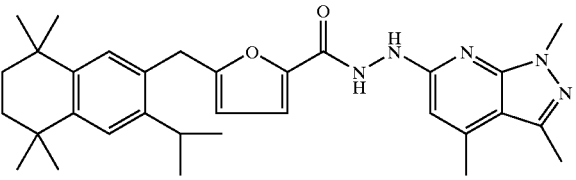

Compound C3

Compound C3 was made by the scheme described in Example C1 above, except using 5-[(5,5,8,8-tetramethyl-3-isopropyl-5,6,7,8-tetrahydro-2-naphtholenyl) methyl]-2-furoyl chloride in place of starting reagent 8. Alternatively, compound 3C can be synthesized from compound C1, by exchanging the methyl at the 3-position on the naphthyl moiety for an isopropyl (recovery 33%). $^1$H NMR (300 MHz, CD$_3$CN): δ 7.29 (1H, s); 7.19 (1H, s); 7.08 (1H, d J=3.4 Hz); 6.31(1H, s); 6.19 (1H, d, J=3.4 Hz); 4.07 (2H, s); 3.77 (3H, s); 3.23 (1H, m); 2.54 (3H, s); 2.52 (3H, s); 1.69 (4H, s); 1.28 (6H, s); 1.25 (6H, s); 1.20 (3H, s); 1.18 (3H, s), APCI-MS m/z 528.3 (M+H)$^+$.

Example C4

5-[(3-chloro-5,5,8,8-tetramethyl-5,6,7,8-tetrahydro-2-naphthalenyl)methyl]-N'-(1,3,4-trimethyl-1H-pyrazolo[3,4-b]pyridin-6-yl)-2-furohydrazide Compound C4

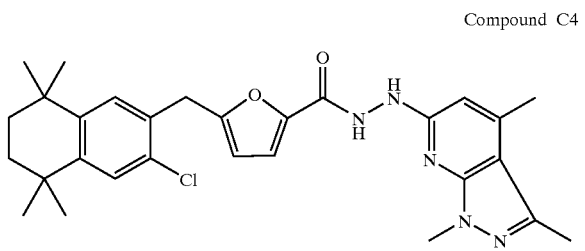

Compound C4 was made by the scheme described in Example C1 above, except using 5-[(5,5,8,8-tetramethyl-3-chloro-5,6,7,8-tetrahydro-2-naphtholenyl) methyl]-2-furoyl chloride as a starting reagent 8. The synthesis of compound 8 is outlined below:

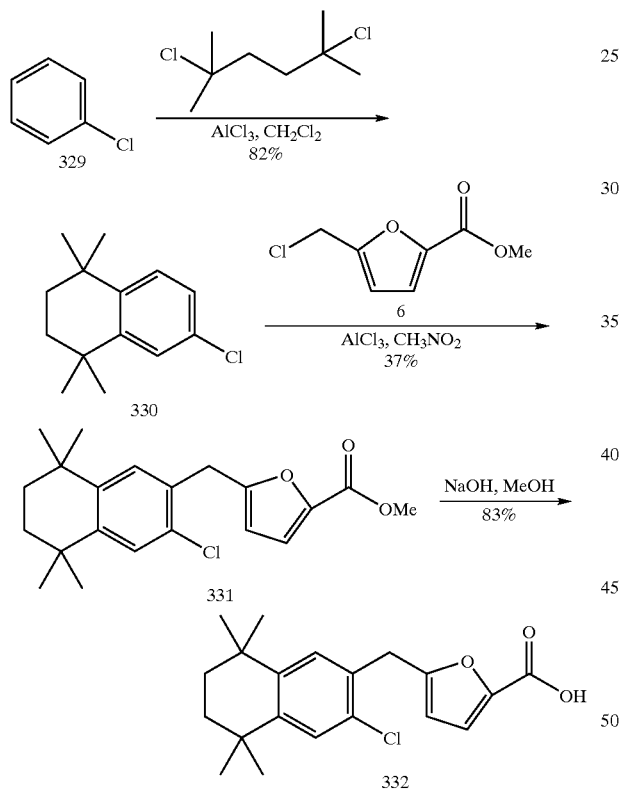

To a solution of mixture of chlorobenzene, compound 329 (5 g, 44.6 mmol.) and 2,5-dichloro-2,5-dimethylhexane (8.2 g, 44.6 mmol.) in $CH_2Cl_2$ (150 mL) was added $AlCl_3$ (2 g, 13.4 mmol.). The solution was stirred at room temperature for one hour. The reaction mixture was slowly poured into ice water, extracted with EtOAc, washed with $H_2O$, dried ($MgSO_4$) and concentrated to give 6-chloro-1,1,4,4-tetramethyl-1,2,3,4-tetrahydronaphathlene, compound 330 (8.2 g), as an oil.

Compounds 330 and 336 were added to dichloroethane, 0.5M. $AlCl_3$ was added slowly over 30 minutes. Once the addition was complete, the reaction mixture was heated to 50° C. overnight. The reaction was then cooled, quenched with $H_2O$, concentrated, and purified by column chromatography using 5% ethyl acetate/hexane, to give compound 331.

Compound 331 was dissolved in THF, 1M, and 10 eq of NaOH in minimal $H_2O$ was added. The reaction mixture was refluxed overnight, cooled and quenched with 1M HCl to afford an acetic pH. The reaction was then extracted with dichloromethane and concentrated to give compound 332.

$^1$H NMR (300 MHz, $CD_3OD$): δ 1.24 (s, 6H), 1,27 (s, 6H), 1.69 (s, 4H), 2.55 (s, 3H), 2.65 (s, 3H), 3.80 (s, 3H), 4.16 (s, 2H), 6.17 (d, 1H), 6.36 (s, 1H), 7.15 (d, 1H), 7.28 (s, 1H), 7.32 (s, 1H), APCI-MS m/z 521.0 $(M+H)^+$.

Example C5

5-[(3,5,5,8,8-Pentamethyl-5,6,7,8-tetrahydro-2-naphthalenyl)methyl]-N'-(2-quinolinyl]-2-furohydrazide Compound C5

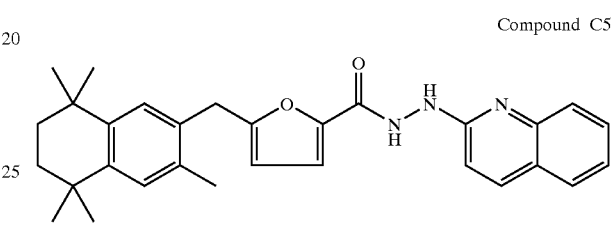

Compound C5 was synthesized from the naphtyl building block described above, utilizing a modified version of the scheme described in Example C1 wherein starting reagent 15 was replaced with a quinoline hydrazide shown below:

quinoline hydrazide

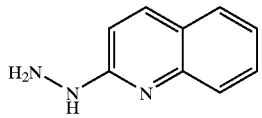

$^1$H NMR (300 MHz, DMSO-$d_6$): δ 1.19 (s, 6H), 1.22 (s, 6H), 1.61 (s, 4H), 2.24 (s, 3H), 3.97 (s, 2H), 6.24 (d, 1H, J=3 Hz), 6.89–6.92 (d, 1H, J=9 Hz), 7.10 (s, 1H), 7.11 (s, 1H), 7.21 (d, 1H, J=3 Hz), 7.23–7.28 (m, 1H), 7.50–7.57 (m, 2H), 7.71–7.74 (d, 1H, J=9 Hz), 8.03 (d, 1H, J=9 Hz), 8.97 (s, 1H), 10.31 (brd, 1H), APCI-MS m/z 468.3 $(M+H)^+$.

Example C6

N'-(4-amino-6-cyclopropyl-1,3,5-triazin-2-yl)-5-[(3,5,5,8,8-pentamethyl-5,6,7,8-tetrahydro-2-naphthalenyl)methyl]-2-furohydrazide Compound C6

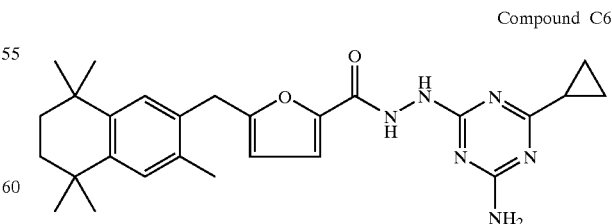

Compound C6 was synthesized from the naphtyl building block described above, utilizing a modified version of the scheme described in Example C1 wherein compound 15 was replaced with a substituted triazine hydrazide shown below:

triazine hydrazide

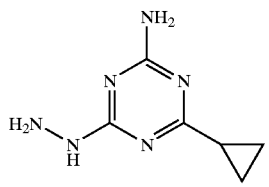

¹HMR (300 MHz, DMSO-d₆): δ 0.85–0.92 (m, 4H), 1.19 (s, 6H), 1.21 (s, 6H), 1.60 (s, 4H), 2.22 (s, 3H), 3.93 (s, 2H), 6.19–6.20 (d, 1H, J=3 Hz), 6.76 ($S_{brd}$, 2H), 7.08 (s, 2H), 7.12–7.23 (m, 1H), 8.86 (s, 1H), 10.07 (s, 1H), APCI-MS m/z 475.6 (M+H)⁺.

Example C7

5-[(3-methoxy-5,5,8,8-tetramethyl-5,6,7,8-tetrahydro-2-naphthalenyl)methyl-N'-{4-[(tertahydro-2-furanylmethyl)amino]-2-pyrimidinyl}-2-furohydrazide Compound C7

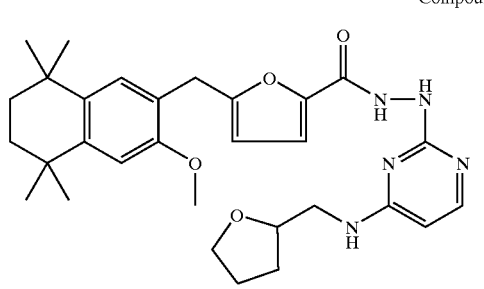

Compound C7 was synthesized using a modified version of the scheme described in Example C1 using 5-[(5,5,8,8-tetramethyl-3-methoxy-5,6,7,8-tetrahydro-2-naphtholenyl) methyl]-2-furoyl chloride in place of starting reagent 8 and wherein compound 15 was replaced with a substituted pyrimidine hydrazide shown below:

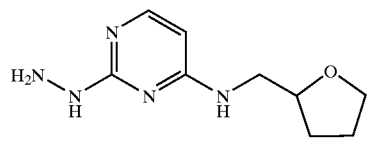

pyrimidine hydrazide

¹H NMR (300 MHz, CDCl₃): δ 1.16 (s, 9H), 2.28 (s, 3H), 4.30 (s, 2H), 6.29 (d, 1H), 7.07 (d, 1H), 7.13 (s, 2H), 7.26 (s, 1H), 12.90 (br s, 1H), APCI-MS m/z 534.2 (M+H)⁺.

Example C8

N'-(3,5-dichloro-4-pyridinyl)-5-[(3,5,5,8,8-pentamethyl-5,6,7,8-tetrahydro-2-naphthalenyl) methyl]-2-furohydrazide Compound C8

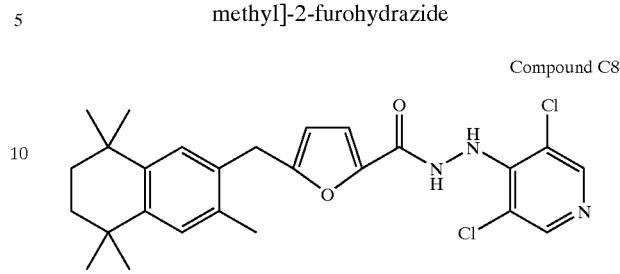

Compound C8 was synthesized from the naphtyl building block described above, utilizing a modified version of the scheme described in Example C1 wherein compound 15 was replaced with a substituted pyridine hydrazide shown below:

pyridine hydrazide

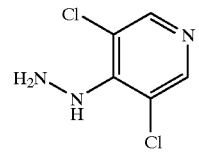

¹H NMR (300 MHz, CDCl₃): δ 1.24 (s, 6H), 1.28 (s, 6H), 1.67 (s, 4H), 2.25 (s, 3H), 3.96 (s, 2H), 6.10 (d, 1H), 6.92 (d, 1H), 7.03 (s, 1H), 7.10 (s, 1H), 7.11 (s, 1H), 8.29 (d, 1H), 8.31 (s, 2H), APCI-MS m/z 486.1 (M+H)⁺.

Example C9

5-[(3,5,5,8,8-Pentamethyl-5,6,7,8-tetrahydro-2-naphthalenyl)methyl]-N'-[5-(trifluoromethyl)-2-pyridinyl]-2-furohydrazide Compound C9

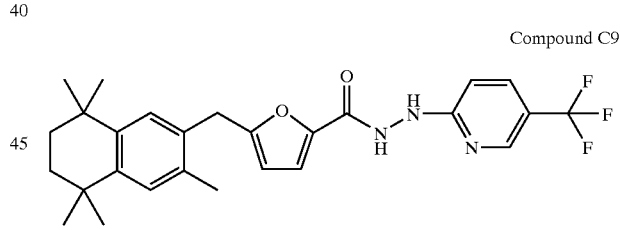

Compound C9 was synthesized from the naphthyl building block described above, utilizing a modified version of the scheme described in Example C1 wherein compound 15 was replaced with a substituted pyridine hydrazide shown below:

pyridine hydrazide

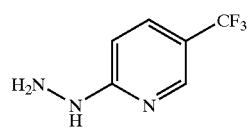

¹H NMR (300 MHz, CDCl₃): δ 1.24, 1.27 (2s, 6H each), 1.66 (s, 4H), 2.23 (s, 6H), 3.95 (s, 2H), 6.07 (d, 1H, J=3.4 Hz), 7.05–7.15 (m, 3H), 7.10 (d, 1H, J=3.4 Hz), 7.93 (d, 1H, J=7.17 Hz), 8.27 (br s, 1H), APCI-MS m/z 486.2 (M+H)⁺.

Example C10

5-[(3,5,5,8,8-Pentamethyl-5,6,7,8-tetrahydro-2-napthalenyl)methyl]-N'-(2-pyridinyl)-2-furohydrazide Compound C10

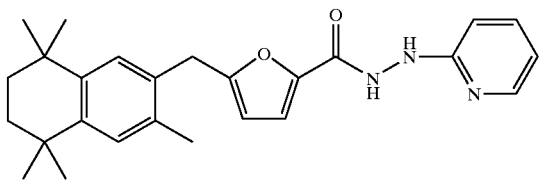

Compound C10 was synthesized from the naphthyl building block described above, utilizing a modified version of the scheme described in Example C1 wherein compound 15 was replaced with the pyridine hydrazide shown below:

pyridine hydrazide

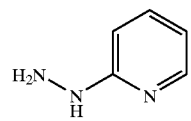

$^1$H NMR (300 MHz, CD$_2$Cl$_2$): δ 6 1.27, 1.29 (2s, 6H each), 1.69 (s, 4H), 2.26 (s, 3H), 3.97 (s, 2H), 6.07 (d, 1H, J=3.4 Hz), 6.95 (m, 1H), 7.09 (d, 1H, J=10.9 Hz), 7.18 (d, 1H, J=3.4 Hz), 7.85–7.98 (m, 2H), 8.5(br s, 1H), 11.5 (br s, 1H), APCI-MS m/z 418.1 (M+H)$^+$.

Example C11

5-[(3,5,5,8,8-Pentamethyl-5,6,7,8-tetrahydro-2-naphthalenyl)methyl]-N'-[3-(trifluoromethyl)-2-pyridinyl]-2-furohydrazide Compound C11

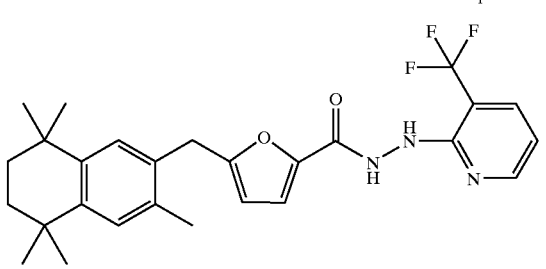

Compound C11 was synthesized from the naphthyl building block described above, utilizing a modified version of the scheme described in Example C1 wherein compound 15 was replaced with a substituted pyridine hydrazide shown below:

pyridine hydrazide

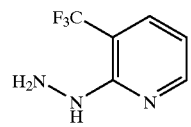

$^1$H NMR (300 MHz, CDCl$_3$): δ 6 1.27, 1.29 (2s, 6H each), 1.69 (s, 4H), 2.26 (s, 3H), 3.97 (s, 2H), 6.02 (d, 1H, J=3.4 Hz), 7.04 (dd, 1H, J=5.67 and 7.55 Hz), 7.11 (d, 1H, J=4.91 Hz), 7.15 (d, 1H, J=3.78 Hz), 7.28 (s, 1H), 8.01 (d, 1H, J=7.18 Hz), 8.36 (d, 1H, J=4.53 Hz), APCI-MS m/z 486.2 (M+H)$^+$.

Example C12

N'-[3-Chloro-5-(trifluoromethyl)-2-pyridinyl]-5-[(3,5,5,8,8-pentamethyl-5,6,7,8-tetrahydro-2-naphthalenyl)methyl]-2-furohydrazide Compound C12

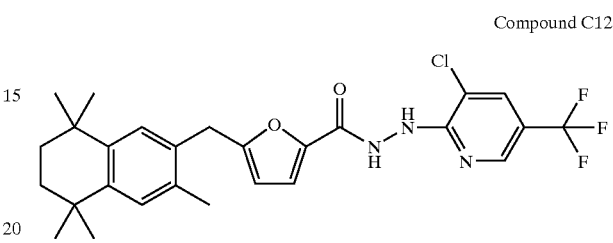

Compound C12 was synthesized from the naphthyl building block described above, utilizing a modified version of the scheme described in Example C1 wherein compound 15 was replaced with a substituted pyridine hydrazide shown below:

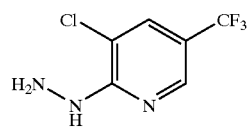

pyridine hydrazide $^1$H NMR (300 MHz, CDCl$_3$): δ 1.24, 1.27 (2s, 6H each), 1.66 (s, 4H), 2.25 (s, 3H), 3.96 (s, 2H), 6.02 (d, 1H, J=3.4 Hz), 7.06 (s, 1H), 7.10 (s, 1H), 7.17 (d, 1H, J=3.4 Hz), 7.83 (br s, 1H), 8.35 (br s, 1H), APCI-MS m/z 522.1 (M+2), 520.1 (M+H)$^+$.

Example C13

N'-[6-methyl-4-(trifluoromethyl)-2-pyridinyl]-5-[(3,5,5,8,8-pentamethyl-5,6,7,8-tetrahydro-2-naphthalenyl)methyl]-2-furohydrazide Compound C13

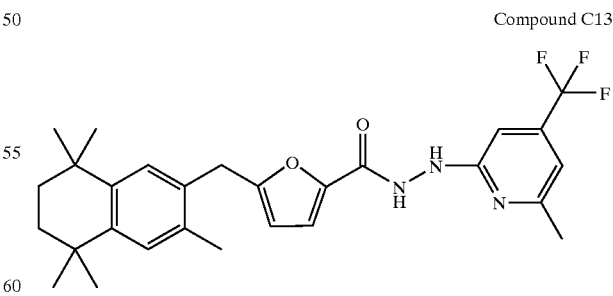

Compound C13 was synthesized from the naphthyl building block described above, utilizing a modified version of the scheme described in Example C1 wherein compound 15 was replaced with a substituted pyridine hydrazide shown below:

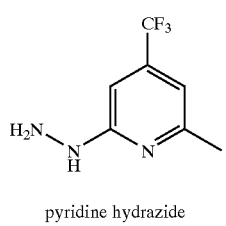

pyridine hydrazide

¹H NMR (300 MHz, CDCl₃): δ 1.23,1.27 (2s, 6H each), 1.66 (s, 4H), 2.25 (s, 3H), 2.65 (s, 3H), 3.96 (s, 2H) 6.09 (d, 1H, J=3.4 Hz), 6.83 (s, 1H), 6.99 (s, 1H), 7.11 (s, 1H), 7.18 (s, 1H), 7.19 (d, 1H, J=3.4 Hz), 8.2 (br s, 1H), APCI-MS m/z 500.2 (M+H)⁺.

Example D1

5-[(4-Benzylphenoxy)methyl]-N'-(1,3,4-trimethyl-1H-pyrazolo[3,4-b]pyridin-6-yl)-2-furohydrazide

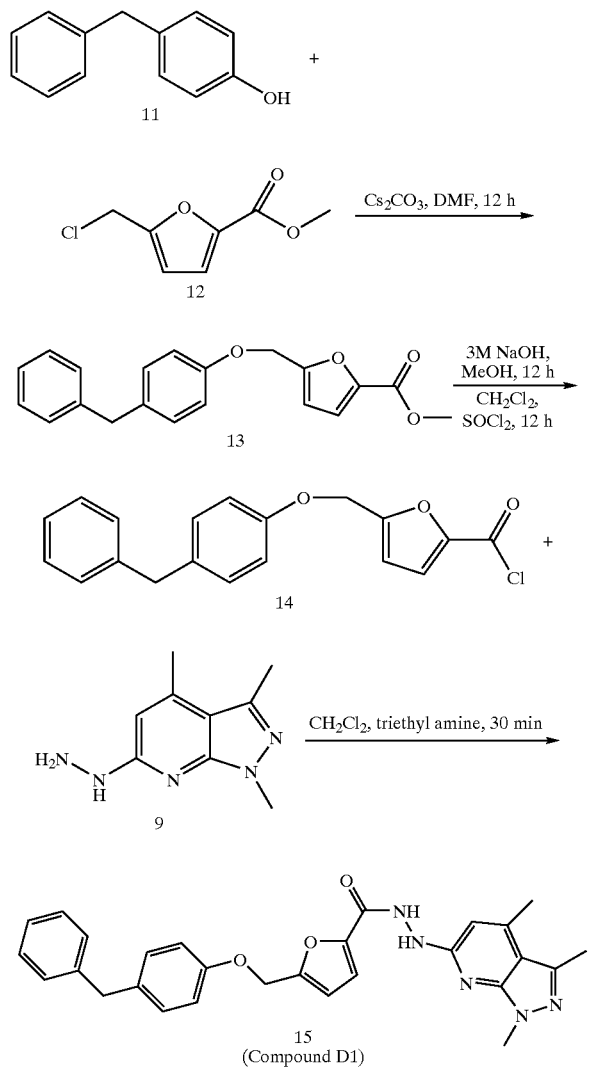

To a solution containing methyl 5-(Chloromethyl)-2-furoate, 12, (5.00 g, 28.6 mmol, 0.5 M) in DMF (60 mL), 4-Benzylphenol, 17, (5.27 g, 28.6 mmol) was added along with Cesium carbonate (9.32 g, 28.6 mmol) and stirred 12 hours at room temperature. The solution was then dissolved in ethyl acetate and washed with water. After evaporation of solvents, the crude mixture was purified by recrystallization in 10% ethyl acetate hexanes to yield 13 (4.3 g, 47%). The ester, 13, (3.71 g, 11.5 mmol, 0.2M) was dissolved in methanol (30 mL) and 3 M sodium hydroxide solution (30 mL) was added. After stirring for 12 hours, the reaction was acidified to pH 2 with concentrated hydrochloric acid. The product was then exctracted into ethyl acetate and evaporated to dryness. The syrup was then crystallized in 50% ethyl acetate hexanes to give 2.12 g (60%) of acid. After converting to acid chloride 20, compound 20 was then coupled with hydrazine 21 to give Compound D1. Additional compounds, other than those listed below, was prepared under these reaction conditions, using above Scheme D or variations or modifications thereof. ¹H NMR (DMSO-d₆): δ 7.30–7.14 (8H, m); 6.99 (2H, d, J=8.7 Hz); 6.76 (1H, d, J=3.4 Hz); 6.23 (1H, s); 5.09 (2H, s); 3.87 (2H, s); 3.70 (3H, s); 2.49 (3H, s); 2.46 (3H, s); MS APCI m/z 482.2 (M+H)⁺.

Example E1

5-[(1,1,3,3,6-pentamethyl-1,3-dihydro-2-benzofuran-5-yl)methyl]-N'-(1,3,4-trimethyl-1H-pyrazolo[3,4-b]pyridin-6-yl)-2-furohydrazide

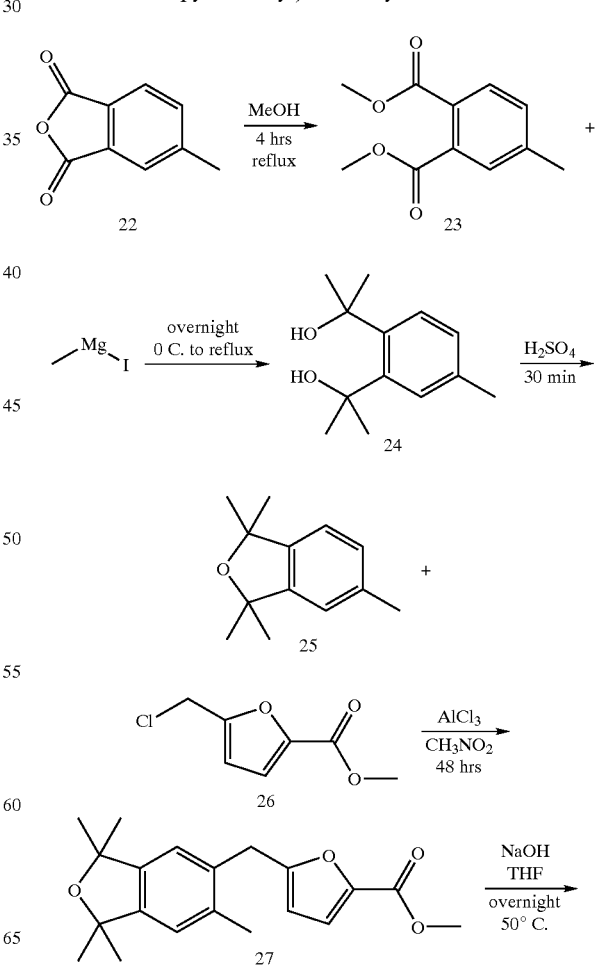

-continued

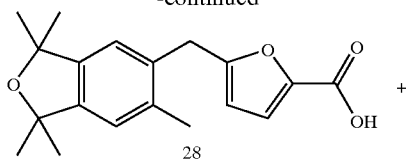

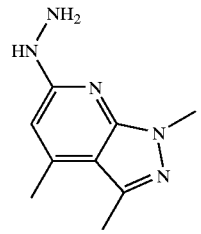

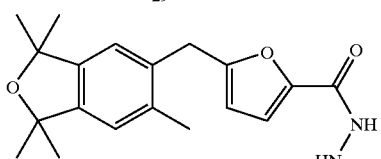

Compound E1

The anhydride, compound 22, was dissolved in methanol and 1% H₂SO₄ and refluxed overnight. Solution was quenched with sat. NaHCO₃, concentrated, plug column, 1:10 ethyl acetate:hexane, and dried over MgSO₄ to give the diester, 23. The diester, compound 23, was dissolved in anhydrous THF, 1M, and cooled to 0° C. Methyl magnesium iodide was added, 6 eq., slowly to the solution of the diester at 0° C. After addition, reaction mixture was allowed to warm to room temperature overnight. The reaction mixture was then refluxed 4 hours. Reaction was quenched with 1M HCl and extracted with ethyl acetate, conc. Mixture was taken in methanol and added cat H₂SO₄ and heated to 50° C. for 30 minutes. Product, compound 25, was purified by distillation, bp 87° C. @ 1 barr. A mixture of product, compound 25, and furan, compound 26, were added to dichloroethane, 0.5M and AlCl₃ was added slowly over 30 minutes. After the addition, the reaction mixture was heated to 50° C. overnight. The reaction was quenched with H₂O, conc. and plug column 5% ethyl acetate/hexane, to give ester. Ester was dissolved in THF, 1M, and was added 10 eq of NaOH in minimal H₂O. Reaction mixture was refluxed overnight. Quenched with 1M HCl to acidic pH. Extracted with DCM and conentrated to give acid. To a mixture of 1 eq of acid, 1.5 eq of HATU, and 4.5 eq of TEA was added to DMF (0.5M) and cooled to 0° C. for thirty minutes. 1.5 eq of the hydrazine compound was added to the mixture and the mixture was allowed to warm to room temperature overnight. Final products were purified by prep HPLC. ¹H NMR (300 MHz, CDCl₃): δ: 1.47 (6H, s), 1.49 (6H, s), 2.33 (3H, s), 2.45 (3H, s), 2.54 (3H, s), 3.86 (3H, s), 4.02 (2H,s) 6.03–6.09 (1H, d, J=3.40 Hz), 6.23 (1H, s), 6.85 (1H, s), 6.91 (1H, s), 7.10–7.15 (1H, d, J=3.40 Hz), APCI-MS m/z 488 (M+H)⁺.

Example E2

N-(5-acetyl-1,3,4-trimethyl-1H-pyrazolo[3,4-b]pyridin-6yl)-5-[(1,1,3,3,6-pentamethyl-1,3-dihydro-2-benzofuran-5-yl)methyl]-2-furohydrazide

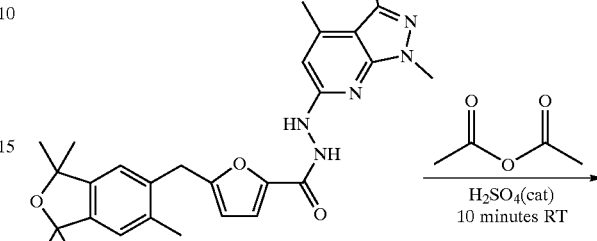

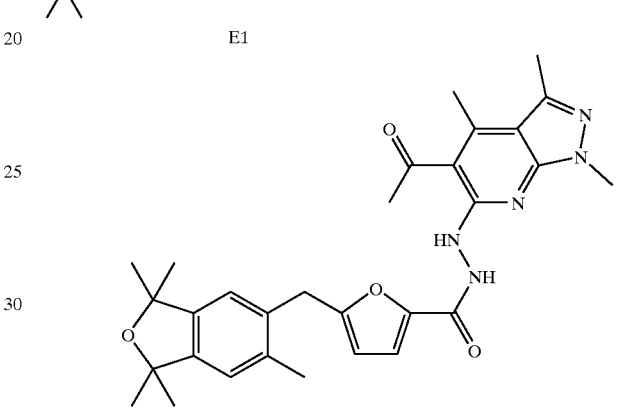

Compound E2 was synthesized in a manner analogous to that of compound E1, using a 5-acetylated 6-hydrazino-1,3,4-trimethyl-1H-pyrazolo [3,4-b] pyridine instead of compound 29. Alternatively, Compound E2 may be synthesized from Compound E1, by adding an acetyl group at the 5-position of the pyridine moiety (recovery 52%). NMR consistent with the desired product were as follows: ¹H NMR (300 MHz, CH₃OD): δ 1.42 (6H, s), 1.47 (6H, s), 2.33 (3H, s), 2.35 (3H, s), 2.61 (3H, s), 2.68 (3H, s), 3.74 (3H, s), 4.12 (2H, s) 6.14–6.18 (1H, d, J=3.40 Hz), 6.98 (1H, s), 7.03 (1H, s), 7.22–7.26 (1H, d, J=3.40 Hz).

Example E3

N'-[3-chloro-5-(trifluoromethyl)pyridin-2-yl]-5-[(1,1,3,3,6-pentamethyl-1,3-dihydro-2-benzofuran-5-yl)methyl]-2-furohydrazide

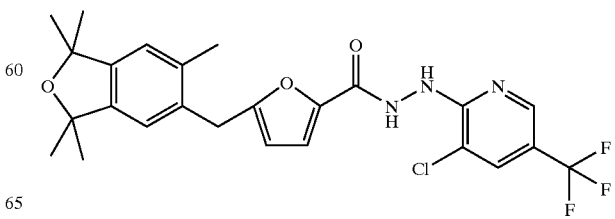

Compound E3 was synthesized in a manner analogous to the procedure used to synthesize compound E1. $^1$H NMR (MeOH-d$_4$): δ 1.46(12H, s), 2.33(3H, s), 4.10(2H, s), 6.08 (1H, d, J=3.02 Hz), 6.98(1H, s), 7.00(1H, s), 7.13(1H, d, J=3.40 Hz), 7.94(1H, s), 8.27(1H, s); APCI-MS m/z 508 (M+H)$^+$.

Example E4

5-(1,1,3,3,6-Pentamethyl-1,3-dihydro-isobenzofuran-5-ylmethyl)-furan-2-carboxylic acid N'-quinolin-2-yl-hydrazide Compound E4

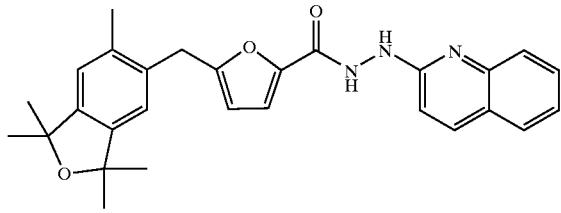

Compound E4 was synthesized in a manner analogous to the procedure used to synthesize compound E1. $^1$H NMR (MeOH-d$_4$): δ 1.48(12H, s), 2.36(3H, s), 4.15(2H, s), 6.22 (1H, d, J=3.40 Hz), 7.00(1H, s), 7.04(1H, s), 7.22(1H, d, J=9.44 Hz), 7.27(1H, d, J=3.40 Hz), 7.60(1H, m), 7.83(1H, m), 7.89(1H, d, J=8.69 Hz), 7.97(1H, d, J=7.93 Hz), 8.50 (1H, d, J=9.44 Hz); APCI-MS m/z 456 (M+H)$^+$.

Example E5

5-(1,1,3,3,6-Pentamethyl-1,3-dihydro-isobenzofuran-5-ylmethyl)-furan-2-carboxylic acid N'-(5-trifluoromethyl-pyridin-2-yl)-hydrazide Compound E5

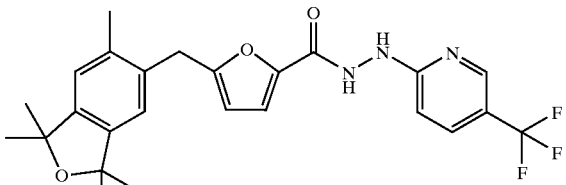

Compound E5 was synthesized in a manner analogous to the procedure used to synthesize compound E1. $^1$H NMR (MeOH-d$_4$): δ 1.61(12H, s), 2.48(3H, s), 4.25(2H, s), 6.25 (1H, d, J=3.40 Hz), 7.03(1H, m), 7.13(1H, s), 7.16(1H, s), 7.30(1H, d, J=3.40 Hz), 8.00(1H, m), 8.47(1H, s); APCI-MS m/z 474 (M+H)$^+$.

Example F1

5-{[-3,5,5,6,8,8-Hexamethyl-5,6,7,8-tetrahydro-2-naphthalenyl]oxy}-N'-(1,3-dimethyl-1H-pyrazolo[3,4-b]pyridin-6-yl)-2-furo hydrazide

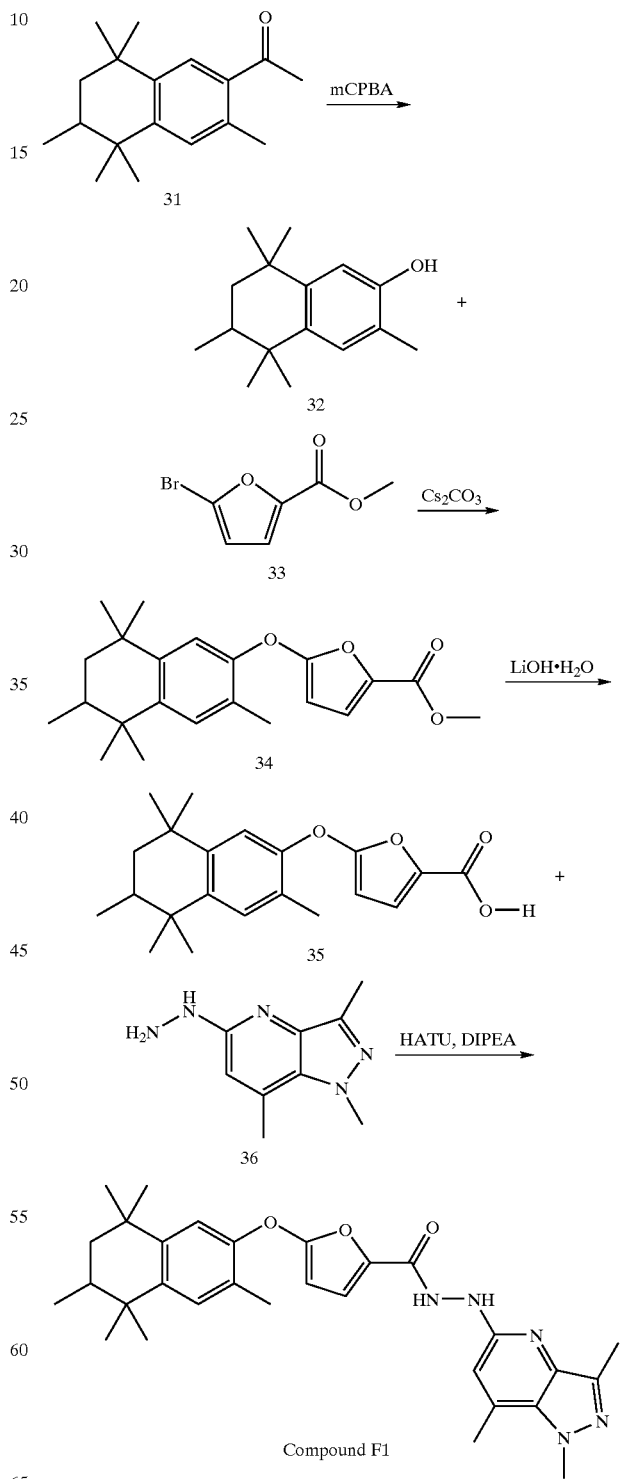

Compound F1

To a solution of 1-[3,5,5,6,8,8,-hexamethyl-5,6,7,8-tetrahydro-2-naphthalenyl] ethanone, 31, (10.32 g, 40 mmol) in dichloromethane (200 ml), was added m-chloroperbenzoic acid (9.86 g, about 70%, 40 mmol). The reaction mixture was stirred at room temperature for 6 hours, and quenched with aqueous sodium bicarbonate (100 ml). The dichloromethane layer was separated, and the aqueous layer was extracted again with dichloromethane (200 ml). The combined organic layer was dried ($Na_2SO_4$), and evaporated. The light yellow-colored syrup was dissolved in methanol (300 ml) and treated with 25% sodium methoxide (13 ml, 60 mmol) for 1 hour. The reaction mixture was neutralized using dilute hydrochloric acid. The methanol evaporated, and the residue triturated with ethyl acetate-water (1:1, 300 ml). The ethyl acetate layer was separated, washed with brine (50 ml), dried ($Na_2SO_4$), and filtered through a silica gel plug. The solvent was evaporated under reduced pressure, and the crude product was crystallized with hexane-ethyl acetate gave a white solid (6.32 g, 68% yield). A mixture of 3,5,5,8,8-Hexamethyl-5,6,7,8-tetrahydro-2-naphthalenol, 32, (232 mg, 1.0 mmol), 5-bromo-2-furoate, 33, (205 mg, 1.0 mmol) and cesium carbonate (1.62 g, 5.0 mmol) in dimethylformamide (10 ml) was stirred for 16 hours at 100–110° C., and was cooled to room temperature (ca. 25° C.). Water (50 ml) was added, and the mixture was extracted with ethyl acetate (2×75 ml). The combined organic extract was washed with water (50 ml), brine (50 ml), dried ($Na_2SO_4$), filtered and evaporated under reduced pressure. The residue on quick chromatography on silica gel gave methyl 5-{[-3,5,5,6,8,8-hexamethyl-5,6,7,8-tetrahydro-2naphthalenyl]oxy}-2-furoate as colorless syrup, 34, (272 mg, 76% yield).

To a solution of methyl 5-{[3,5,5,6,8,8-hexamethyl-5,6,7,8-tetrahydro-2naphthalenyl]oxy}-2-furoate, 34, (250 mg, 0.7 mmol) in THF-MeOH-$H_2O$(7:5:5, 7 ml) was added lithium hydroxide monohydrate (147 mg, 3.5 mmol). The reaction mixture was stirred at room temperature for 4 hours and evaporated under reduced pressure. The residue was triturated with ethyl acetate-water (50 ml, 1:1) and acidified with 1N HCl to pH 5.0. The organic extract was washed with brine (20 ml), dried ($Na_2SO_4$), filtered through a plug of silica gel and evaporated under reduced pressure to give a light brown syrup, 35 (212 mg, 88% yield).

A mixture of 5-{[3,5,5,6,8,8-hexamethyl-5,6,7,8-tetrahydron-2-naphthalenyl]oxy}-2-furoic acid, 35, (100 mg, 0.28 mmol), 1,3,4-trimethyl-1H-pyrazolo[3,4-b]pyrid-6-yl hydrazine, 36, (53 mg, 0.28 mmol), diisopropyl ethylamine (52 ml, 0.33 mmol), in dimethylformamide (5.6 ml) was added HATU(106 mg, 0.28 mmol). The reaction mixture was stirred at room temperature for 16 hours and evaporated to dryness under reduced pressure. The residue was triturated with ethyl acetate-water (50 ml, 1:1), ethyl acetate layer separated, dried ($Na_2SO_4$), filtered through a silica plug, and evaporated. The residue was purified by prep TLC using hexane-ethyl acetate (7:3, 3 development). The band at $R_f$ 0.3 was isolated, crystallized using the same solvent to give N'-(1,3-dimethyl-1H-pyrazolo[3,4-b]pyridin-6-yl)-5-{[(6S)-3,5,5,6,8,8-hexamethyl-5,6,7,8-tetrahydro-2naphthalenyl]oxy}-2-furohydrazide as light brown solid (44 mg, 31% yield), melting point of 169–170° C. $^1$H NMR (300 MHz, DMSO-$d_6$): δ 0.99 (d, 3H, J=6.42 Hz), 1.06 (s, 3H), 1.22, 1.24, 1.32 (3s, 3H each), 1.3–1.45 (m, 1H), 1.62 (t, 1H, J=12.82 Hz), 1.8–1.95 (m, 1H), 2.25, 2.46, 2.55, 3.88 (4s, 3H each), 5.35 (d,1H, J=3.4 Hz), 6.25 (s, 1H), 6.98 (s, 1H), 7.18 (d, 1H, J=3.78), 7.22 (s, 1H), 7.26 (s, 1H), 7.34 (br s, 1H), 8.47 (br s, 1H), APCI-MS m/z 516.2.1 (M+H)$^+$, HRMS (M+H)$^+$expected 516.29740. found (M+H)$^+$516.297.

Example F2

5-[(3,5,5,8,8-pentamethyl-5,6,7,8-tetrahydro-2-naphthalenyl)oxy]-N-(1,3,4-trimethyl-1H-pyrazolo[3,4-b]pyridin-6-yl)-2-furohydrazide Compound F2

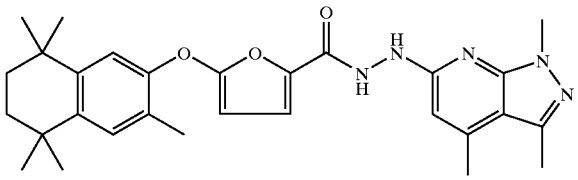

Compound F2 was synthesized in a manner analogous to the procedure used to synthesize compound F1, using 1-[3,5,5,8,8,-pentamethyl-5,6,7,8-tetrahydro-2-naphthalenyl] ethanone in place of compound 31. Compound 31 was synthesized according to the following scheme.

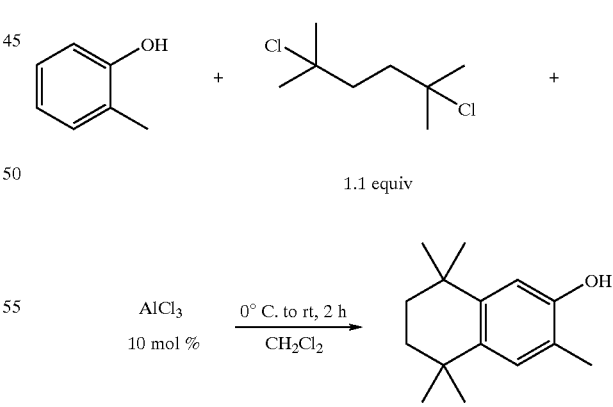

$^1$H NMR (300 MHz, CDCl$_3$): δ 1.16 (s, 6H), 1.21 (s, 6H), 1.61 (s, 4H), 2.18 (s, 3H), 2.44 (s, 3H), 2.49 (s, 3H), 3.82 (s, 3H), 5.28 (d, 1H), 6.21 (s, 1H), 6.93 (s, 1H), 7.07 (brs, 1H), 7.10 (d, 1H), 7.19 (s, 1H), 8.32 (br s, 1H).

Example F3

4-Bromo-5-[(3,5,5,8,8-pentamethyl-5,6,7,8-tetrahydro-2-naphthalenyl)oxy]-N'-[1,3,4-trimethyl-1H-pyrazolo[3,4-b]pyridin-6-yl)-2-furohydrazide

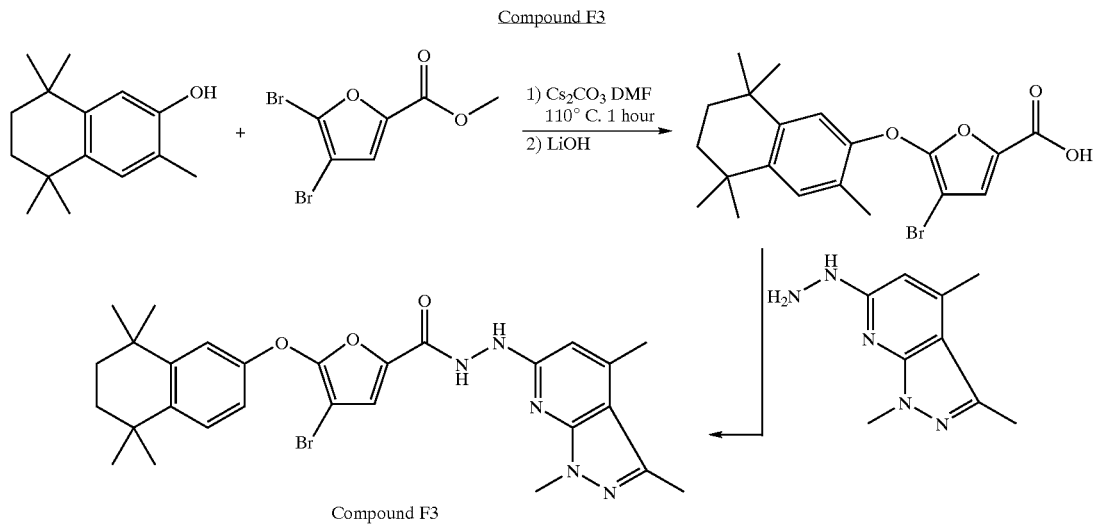

Compound F3 was synthesized in a manner analogous to the procedure used to synthesize compound F1, using 1-[5,5,8,8,-tetramethyl-3-methyl-5,6,7,8-tetrahydro-2-naphthalenyl] ethanone in place of compound 31. $^1$H NMR (300 MHz, DMSO-d$_6$): δ 1.19, 1.27 (s, 6H each), 1.65 (s, 4H), 2.30 (s, 3H), 2.50 (s, 3H), 2.53 (s, 3H), 3.74 (s, 3H), 6.27 (s, 1H), 6.84 (s, 1H), 7.30 (s, 1H), 7.55 (s, 1H). 8.80 (br, 1H), 10.40 (br, 1H), APCI-MS m/z 580.4 (M+H)$^+$.

Example F4

5-[(5,5,8,8-tetramethyl-5,6,7,8-tetrahydro-2-naphthalenyl)oxy]-N'-(1,3,4-trimethyl-1H-pyrazolo[3,4-b]pyridin-6-yl)-2-furohydrazide

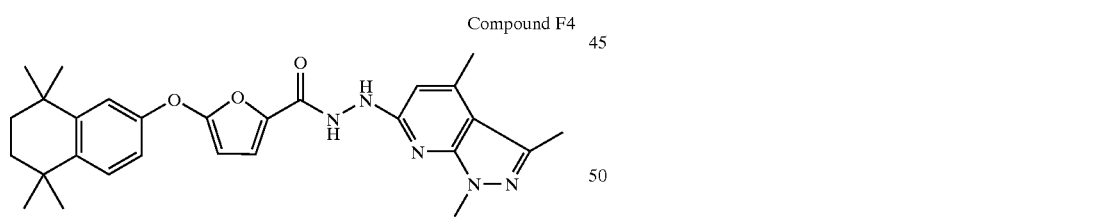

Compound F4 was synthesized in a manner analogous to the procedure used to synthesize compound F1, using 1-[5,5,8,8,-tetramethyl-5,6,7,8-tetrahydro-2-naphthalenyl] ethanone in place of compound 31. $^1$H NMR (300 MHz, CDCl$_3$): δ 1.27 (s, 12H), 1.69 (s, 4H), 2.57 (s, 3H), 2.59 (s, 3H), 3.41 (s, 3H), 5.55 (d, 1H), 6.40 (s, 1H), 6.90 (d, 1H), 7.07 (d, 1H), 7.22 (s, 1H), 7.31 (d, 1H), 10.40 (br, 1H), APCI-MS m/z 488.3 (M+H)$^+$.

Examples G1 and G2

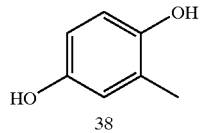 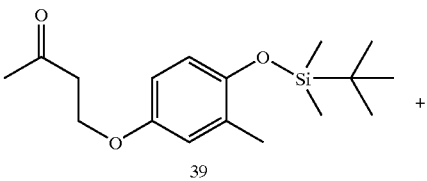

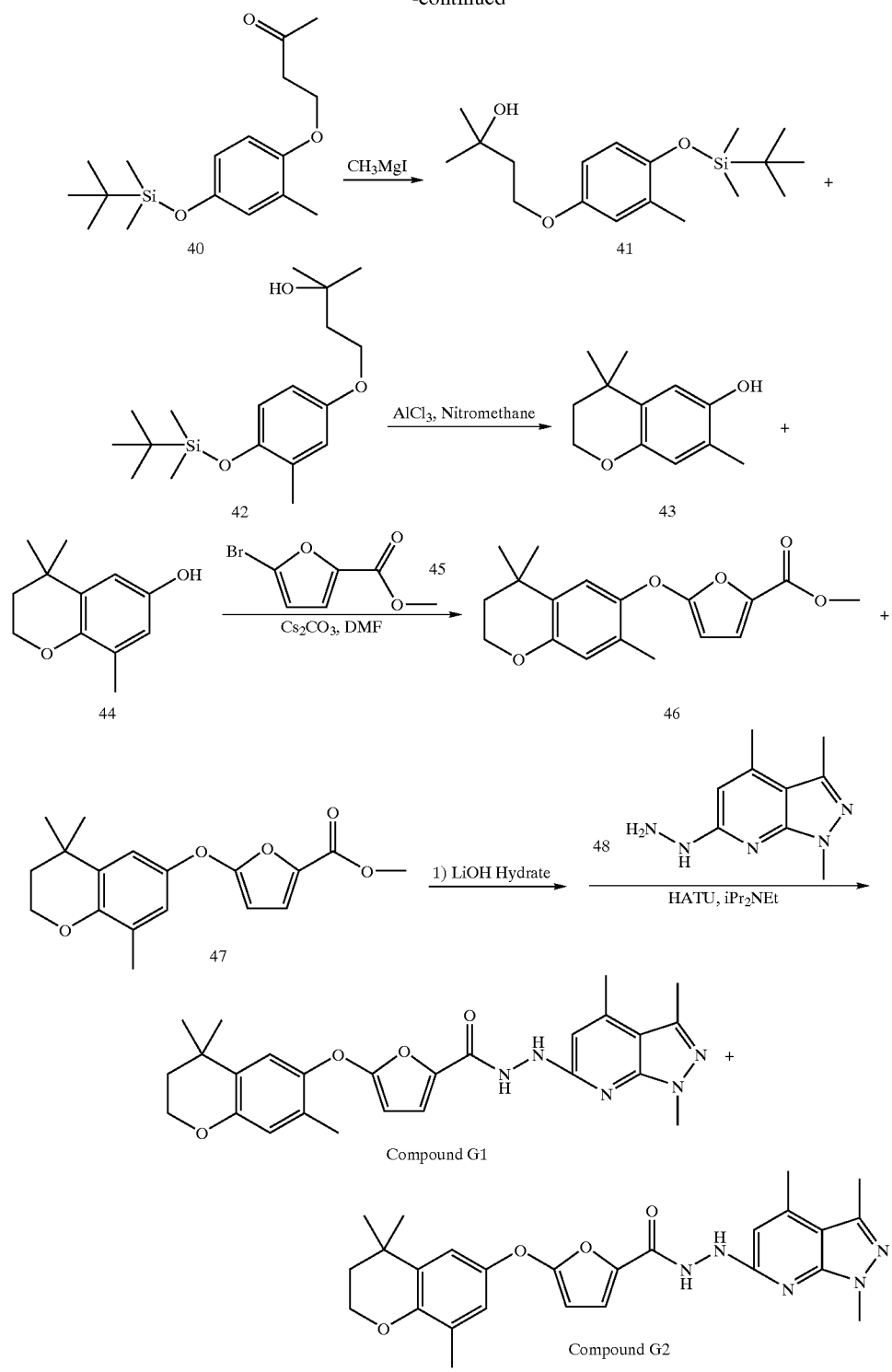

To methylhydroquinone (49.6 g, 400 mmol), methyl vinyl ketone (95%, 29.5 gm, 400 mmol) in chloroform (800 mL), added diispropyl ethyl amine (10.3 gm, 80 mmol). The mixture was heated at reflux for 16 hours, allowed to cool to room temperature and evaporated. The residue had about 50% of both products and 50% starting material. The products were separated from starting material by quick silica plug filtration. The crude products dissolved in DMF (100 mL), and treated with TBDMS-Cl (13.48 g, 89.48 mmol) and imidazole (6.09 gm, 89.08 mmol) for 6 hours. The reaction mixture was partitioned between water and ethyl acetate (500 mL, 1:1). The ethyl acetate layer was dried over sodium sulfate and filtered through a silica plug. Yield was 19.3 g (70% based on starting material recovered).

To a 3.0 M solution of methyl magnesium iodide in diethyl ether (45.8 mL, 137.6 mmol) was added a mixture of 4-(4-{tert-butyl(dimethyl)silyl]oxy}-3-methylphenoxy)-2-butanone and 4-(4-{tert-butyl(dimethyl)silyl]oxy}-2-methylphenoxy)-2-butanone 39 and 40 (19.3 g, 62.56 mmol) in diethyl ether (300 mL) in about 3 hours. The solution was stirred at room temperature for 30 minutes, after which quenched with water and dilute hydrochloric acid. The organic layer was separated, dried over sodium sulfate, filtered through a silica plug. Colorless syrup 16.44 g (81% yield).

To aluminium chloride (11.5 g, 86.23 mmol) in 115 mL nitromethane, was added a mixture 4-(4-[tert-butyl(dimethyl)silyl]oxy)-3-methylphenoxy)-2-butanol and 4-(4-{tert-butyl(dimethyl)-silyl]oxy}-2-methylphenoxy)-2-butanol (14.0 gm, 43.13 mmol) in 100 mL of nitromethane. The mixture was stirred at room temperature for 16 hours. Solvent evaporated, the residue was triturated with ethyl acetate-water mixture (1:1, 500 mL). The organic layer was separated, dried over sodium sulfate, and purified by filtering through a silica plug. Colorless syrup 7.5 g (90% yield). To a mixture of 4,4,7-trimethyl-6-chromanol, 4,4,8-trimethyl-6-chromanol (150 mg, 0.78 mmol) and methyl 5-bromo-2-furoate 45 (160 mg, 0.78 mmol) in DMF (8 mL) was added cesium carbonate (0.508 g, 1.56 mmol). The mixture was stirred at 120° C. for 16 hours. Evaporated to dryness and triturated with ethyl acetate-water (1:1,100 mL). The organic layer on usual work up, and plug filtration gave a mixture 167 mg (68% based on chromanol).

To a mixture of methyl 5-[(4,4,7-trimethyl-3,4-dihydro-2H-chromen-6-yl)oxy]-2-furoate and methyl 5-[(4,4,8-trimethyl-3,4-dihydro-2H-chromen-6-yl)oxy]-2-furoate, 46 and 47 (167 mg, 0.52 mmol) in THF-MeOH-$H_2O$ (7:5:5, 5 mL) was added lithium hydroxide monohydride (109 mg, 2.6 mmol). The reaction was stirred for 4 hours at room temperature. The mixture evaporated to dryness, diluted with 30 mL ethyl acetate and 50 mL of water. After acidification with diluted HCl, ethyl acetate layer separated, dried and evaporated to give mixture of corresponding acids, 143 mg (91% yield). The acids could not be separated using column chromatography or crystallization.

To the mixture of acids (35 mg, 0.11 mmol) in DMF (1.15 mL) were added 1,3,4-trimethyl-1H-pyrazolo [3,4-b]pyrid-6-ylhydrazine (22 mg, 0.11 mmol), 48, DIPEA (15 mg, 0.11 mmol) and HATU (42 mg, 0.11 mmol). The reaction was stirred for 16 hours at room temperature, and evaporated. The residue on purification using HPLC gave compound G1 (15 mg) and compound G2 (4.5 mg). Additional compounds, other than those listed below, was prepared under these reaction conditions, using above Scheme G or variations or modifications thereof.

Example G1

5-[(4,4,8-Trimethyl-3,4-dihydro-2H-chromen-6-yl)oxy]-N'-(1,3,4-trimethyl-1H-pyrazolo[3,4-b]pyridin-6-yl)-2-furohydrazide $^1$H NMR (300 MHz, CDCl$_3$): δ 1.32 (s, 6H), 1.84 (t, 2H, J=5.29 Hz), 2.20, 2.60, 2.63 (3s, 3H each), 3.45 (br s, H$_2$O), 4.06 (s, 3H), 4.21 (t, 1H, J=5.29 Hz), 5.24 (d, 1H, J=3.77 Hz), 6.47 (s, 1H), 6.70 (s, 1H), 7.03 (s, 1H), 7.22 (d, 1H, J=3.78 Hz), 8.23 (br s, 1H), 10.9 (br s, 1H), APCI-MS m/z 476.1 (M+H)$^+$.

Example G2

5-[(4,4,7-Trimethyl-3,4-dihydro-2H-chromen-6-yl)oxy]-N'-(1,3,4-trimethyl-1H-pyrazolo[3,4-b]pyridin-6-yl)-2-furohydrazide $^1$H NMR (300 MHz, CDCl$_3$): δ 1.34 (s, 6H), 1.86 (t, 2H, J=5.29 Hz), 2.20 (s, 3H), 2.59, 2.62 (2s, 3H each), 4.05 (s, 3H), 4.25 (t, 1H, J=5.29 Hz), 5.44 (d, 1H, J=3.78 Hz), 6.44 (s, 1H), 6.79 (d, 1H, J=3.02 Hz), 6.95 (d, 1H, J=3.02 Hz), 7.23 (d, 1H, J=3.77 Hz), 8.26 (br s, 1H), 10.58 (brs, 1H), APCI-MS m/z 476.2 (M+H)$^+$. HRMS (M+H)$^+$expected 476.2298. found (M+H)$^+$476.2294.

Example H1

N,N-diethyl-4-methyl-3-[(5-{[2-(1,3,4-trimethyl-1H-pyrazolo[3,4-b]pyridin-6-yl)hydrazino]carbonyl}-2-furyl)oxy]benzamide

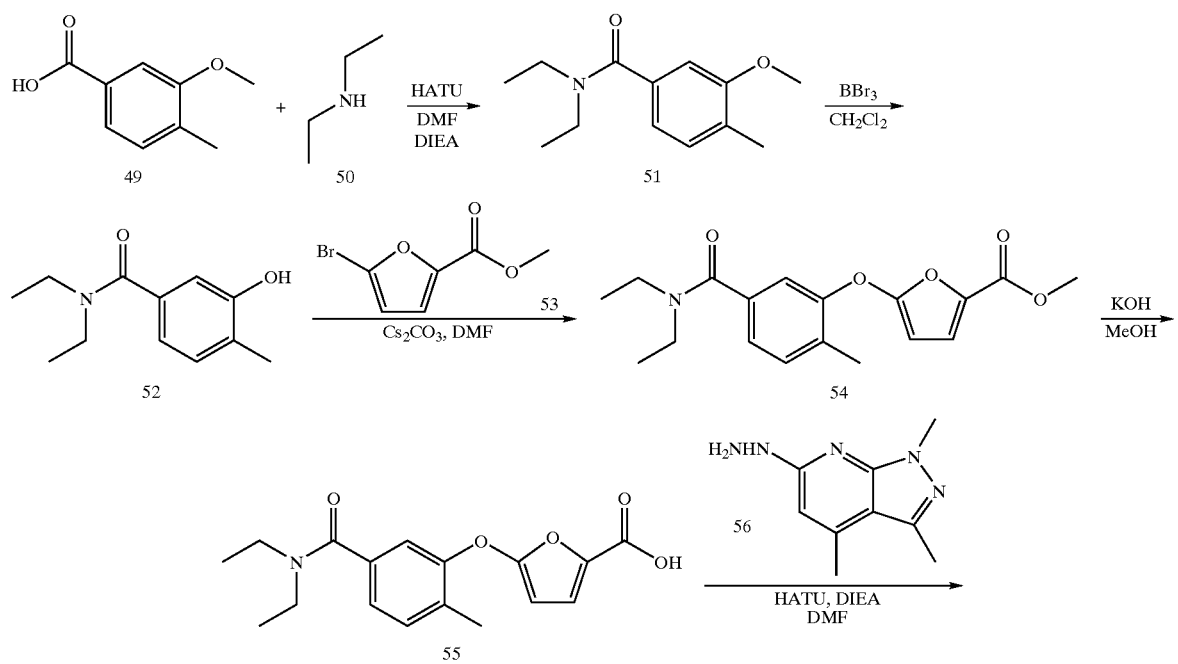

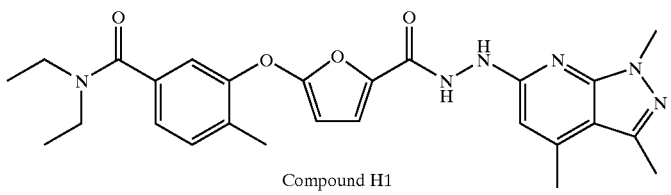

Compound H1

To a DMF solution (15 mL) of 49 (0.831 g, 5 mmol) was added DIEA (7.5 mmol), HATU (5 mmol), and diethylamine 50 (5.5 mmol) successively. The reaction mixture was stirred at room temperature overnight. DMF was removed under reduced pressure. The oily residue was dissolved in ethyl acetate, washed with aqueous 10% HCl, saturated sodium bicarbonate, brine, dried over magnesium sulfate and evaporated to a dark oil 51 (91 g, 90% yield). A methylene chloride solution (10 mL) of 51 (0.686 g, 3.1 mmol) was cooled in dry ice/acetone bath.

To this cooled solution was added dropwise a solution of 1M BBr$_3$ in CH$_2$Cl$_2$ (6.2 mL). The reaction mixture was allowed to warm to room temperature. After 2 hours at room temperature, the reaction was stopped by addition of methanol (5 mL). The mixture was washed with aqueous 10% HCl, and brine. The organic layer was dried over magnesium sulfate and evaporated. The yield of 52 was close to quantitative. A mixture of 52 (0.68 g, 3.29 mmol), 53 (0.338 g, 1.65 mmol), and cesium carbonate (1.07 g, 3.29 mmol) in DMF (15 mL) was stirred at 85° C. overnight under argon atmosphere. DMF was then removed under reduced pressure. The residue was dissolved in ethyl acetate, washed with aqueous 10% HCl, brine, dried over magnesium sulfate and evaporated. The product 54 was purified by flash chromatography (1:1 EtOAc/hexanes): 0.534 g. The methyl ester 54 (0.524 g, 1.58 mmol) was saponified to the acid 55 under standard conditions (methanolic KOH). The reaction was monitored by TLC. A portion of the isolated crude carboxylic acid 55 (0.12 g, 0.378 mmol) was dissolved in DMF (3 mL).

To this solution were added HATU (0.416 mmol), DIEA (1.13 mmol), and 56 (0.080 g, 416 mmol). The reaction mixture was stirred at room temperature overnight. DMF was removed under reduced pressure. The residue was taken up in ethyl acetate and washed with 10% HCl, saturated sodium bicarbonate, brine, dried (magnesium sulfate), and evaporated. The product, compound H1 (10 mg) was purified by prep TLC (5% MeOH/95%CH$_2$Cl$_2$). $^1$H NMR (CDCl$_3$): δ 0.97–1.15 (br s, 6H), 2.36 (s, 3H), 2.54 (s, 3H), 2.57 (s, 3H), 3.28–3.65 (br d, 4H), 3.89 (s, 3H), 5.52 (d, 1H), 6.29 (s, 1H), 6.97 (s, 1H), 7.08 (s, 1H), 7.15–7.32 (m, 3H), 8.47 (br s, 1H), MS (APCI+): 491.2 (M+H)$^+$.

Scheme I

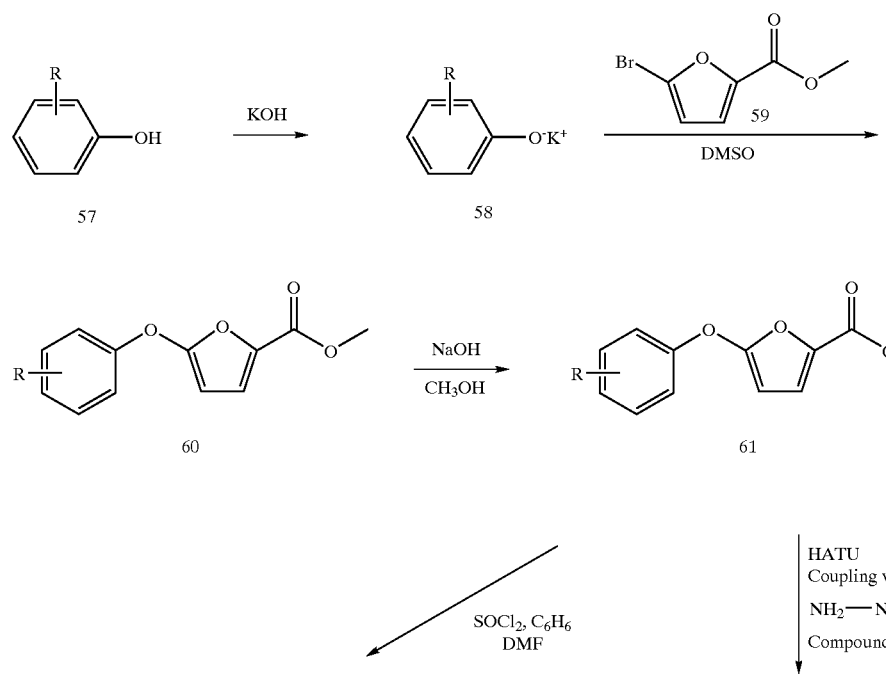

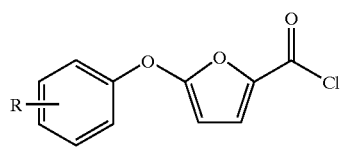

A mixture of potassium hydroxide (2.55 g, 44.8 mmol) and the appropriate phenol, 57, (52.9 mmol) is heated in an oil bath at 150–155° C. for 1–2 hours. The dark colored liquid is then evacuated at 130–140° C. to remove water. The residue is dried in vacuo overnight to give compound 58. Alternatively, the phenoxide 58 may be prepared by reaction with potassium t-butoxide in tetrahydrofuran.

Condensation: A mixture of potassium phenoxide, 58, (7 mmol) and methyl 5-bromo-2-furoate, 59, (5.8 mmol) in DMSO (10 mL) is heated at 85° C. under nitrogen atmosphere. The reaction mixture was then diluted with water, and the aqueous mixture was acidified with concentrated HCl, and extracted with diethyl ether. The combined ether extracts are concentrated and the product, compound 60, is purified by silica gel chromatography, eluting with a mixture of ethyl acetate and hexanes (1:5 to 1:1 v/v). Yield was in the range of 50–80%.

Saponification: The methyl ester, 60, obtained from above is dissolved in methanol (4 mmol in 15 mL of solvent) and aqueous sodium hydroxide (0.7 g in 5 mL water) is added. The reaction is monitored by TLC for completion. It is concentrated, diluted with water, and extracted with diethyl ether. The aqueous layer is then acidified with concentrated HCl, and extracted with ethyl acetate. The ethyl acetate extracts are washed with brine, dried over magnesium sulfate and concentrated to give a solid residue. The product 5-substituted-2-furoic acid, compound 61, may be purified, if necessary, by silica gel chromatography. Yield is generally greater than 90%. Various coupling procedures for various hydrazides from either the acid 61 or the acid halide reagent 62 gave the desired products.

Example I1

5-(1-Acetyl-7-chloro-4,4-dimethyl-1,2,3,4-tetrahydro-quinolin-6-yloxy)-furan-2-carboxylic acid N'-(1,3,4-trimethyl-1H-pyrazolo[3,4-b]pyridin-6-yl)-hydrazide Compound I1

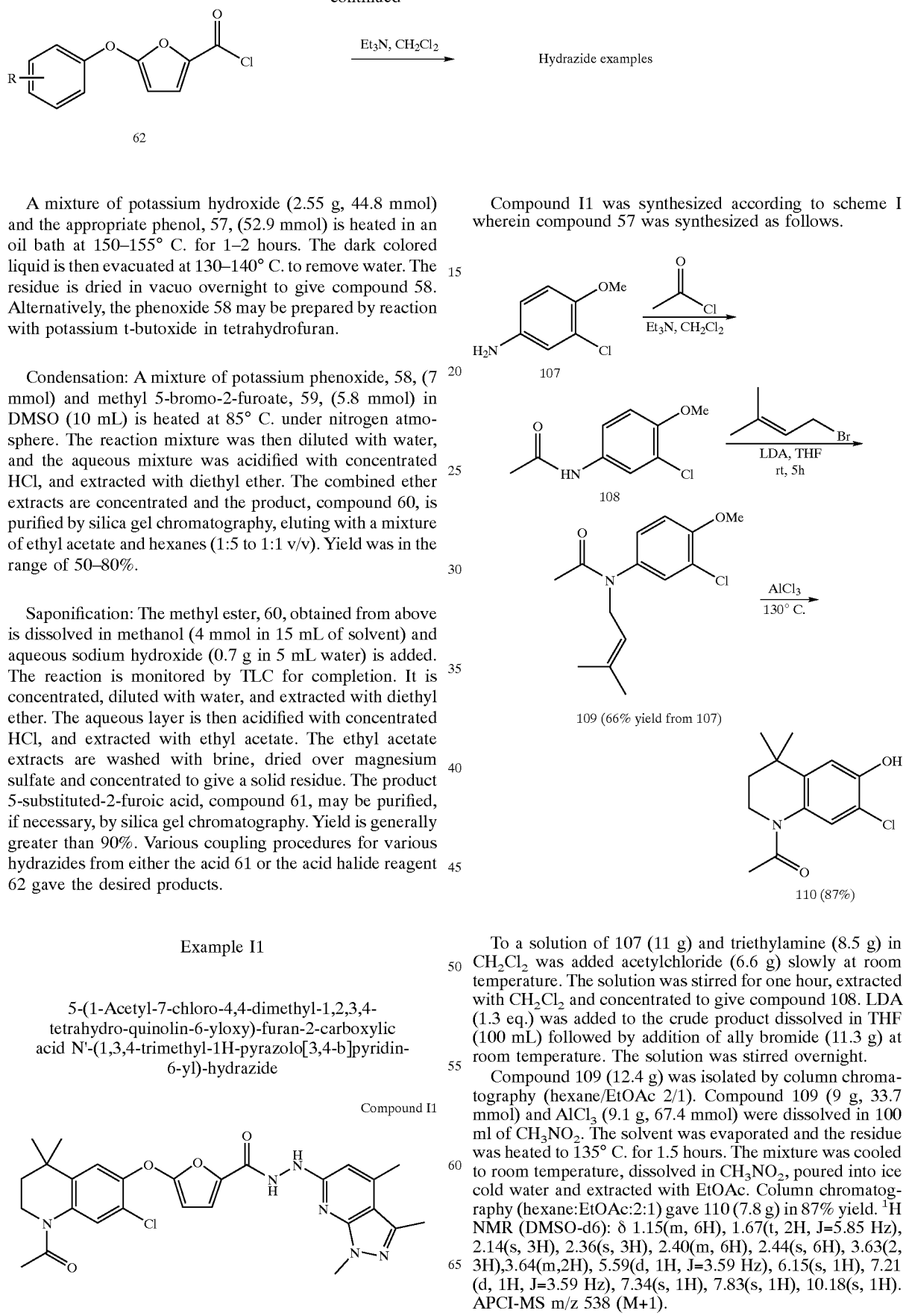

Compound I1 was synthesized according to scheme I wherein compound 57 was synthesized as follows.

To a solution of 107 (11 g) and triethylamine (8.5 g) in CH$_2$Cl$_2$ was added acetylchloride (6.6 g) slowly at room temperature. The solution was stirred for one hour, extracted with CH$_2$Cl$_2$ and concentrated to give compound 108. LDA (1.3 eq.) was added to the crude product dissolved in THF (100 mL) followed by addition of ally bromide (11.3 g) at room temperature. The solution was stirred overnight.

Compound 109 (12.4 g) was isolated by column chromatography (hexane/EtOAc 2/1). Compound 109 (9 g, 33.7 mmol) and AlCl$_3$ (9.1 g, 67.4 mmol) were dissolved in 100 ml of CH$_3$NO$_2$. The solvent was evaporated and the residue was heated to 135° C. for 1.5 hours. The mixture was cooled to room temperature, dissolved in CH$_3$NO$_2$, poured into ice cold water and extracted with EtOAc. Column chromatography (hexane:EtOAc:2:1) gave 110 (7.8 g) in 87% yield. $^1$H NMR (DMSO-d6): δ 1.15(m, 6H), 1.67(t, 2H, J=5.85 Hz), 2.14(s, 3H), 2.36(s, 3H), 2.40(m, 6H), 2.44(s, 6H), 3.63(2, 3H),3.64(m,2H), 5.59(d, 1H, J=3.59 Hz), 6.15(s, 1H), 7.21 (d, 1H, J=3.59 Hz), 7.34(s, 1H), 7.83(s, 1H), 10.18(s, 1H). APCI-MS m/z 538 (M+1).

Example I2

5-(3-Isopropyl-1,1,2,6-tetramethyl-indan-5-yloxy)-furan-2-carboxylic acid N'-(1,3,4-trimethyl-1H-pyrazolo[3,4-b]pyridin-6-yl)-hydrazide Compound I2

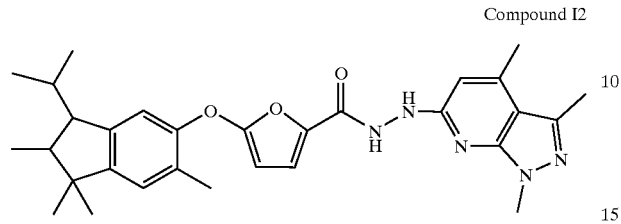

Compound I2 was synthesized according to scheme I where compound 57 was

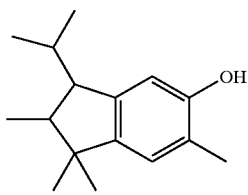

$^1$H (300 MHz, MeOH-d$_4$): δ 0.95 (s, 3H), 0.99 (d, 6H, J=8.31 Hz), 0.98 (d, 3H, J=7.74 Hz), 1.09 (d, 3H, J=6.99 Hz), 1.27 (s, 3H), 1.85 (dd, 2H, J=6.4 and 9.82 Hz), 2.25 (s, 3H), 2.30–2.60 (m, 1H), 2.55, 2.57 (2s, 3H each), 2.75 (dd, 1H, J=2.58 and 5.66 Hz), 3.81 (s, 3H), 5.34 (d,1H, J=3.59 Hz), 6.36, 6.92, 7.06 (3s, 1H each), 7.20 (d, 1H, J=3.59 Hz). APCI-MS m/z 516.2 (M+H)$^+$

Example I3

5-(3-Chloro-2-isopropyl-5-methylphenoxy)-N'-(1,3,4-trimethyl-1H-pyrazolo[3,40b]pyridin-6-yl)-2-furohydrazide Compound I3

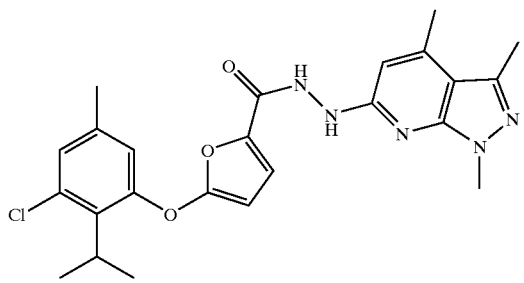

Scheme I was tailored for the synthesis of Compound I3 by using 2-isopropyl, 3-chloro, 5-methyl phenol as the starting reagent 57 and coupling the resultant acid as described above. $^1$H NMR (300 MHz, CDCl$_3$): δ 1.24 (s, 3H), 1.27 (s, 3H), 2.34 (s, 3H), 2.59 (s, 3H), 2.60 (s, 3H), 3.25 (septet, 1H), 3.99 (s, 3H), 5.47 (d, 1H, J=3 Hz), 6.40 (s, 1H), 6.93 (s, 1H), 7.22 (d, 1H, J=3 Hz), 7.32 (s, 1H), 8.36 (s, 1H), 9.50 (br s, 1H), APCI-MS m/z 468.2 (M+H)$^+$.

Example I4

5-(2-Methylphenoxy)-N'-(1,3,4-trimethyl-1H-pyrazolo[3,4-b]pyridin-6-yl)-2-furohydrazide Compound I4

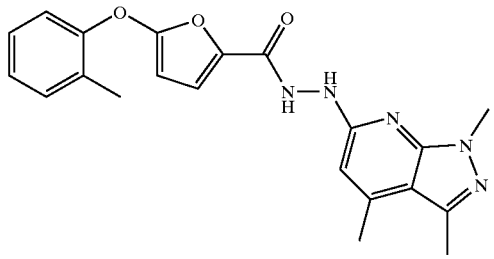

Scheme I was tailored for the synthesis of compound I4 by using o-cresol as the starting reagent 57 and coupling the resultant acid 61 as described above. $^1$H NMR (300 MHz, CDCl$_3$): δ 8.36 (s, 1H), 7.28–7.12 (m, 4H), 7.06 (s, 1H, J=8 Hz), 6.95 (d, 1H, J=3 Hz), 6.29 (s, 1H), 5.43 (d, 1H, J=3 Hz), 3.87 (s, 3H), 2.56 (s, 3H), 2.54 (s, 3H), 2.33 (s, 3H).

Example I5

5-[(6-Methoxy-3,3-dimethyl-1-oxo-2,3-dihydro-1H-inden-5-yl)oxy]-N'-(1,3,4-trimethyl-1H-pyrazolo[3,4-b]pyridin-6-yl)-2-furohydrazide Compound I5

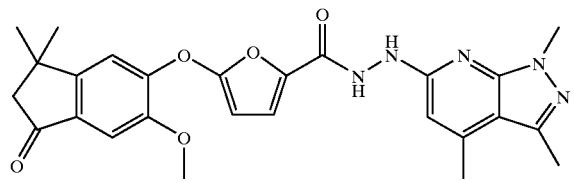

Scheme I was tailored for the synthesis of Compound I5 by using an indene phenol as the starting reagent 57 and coupling the resultant acid 61 as described above. The phenol was synthesized according to the following scheme.

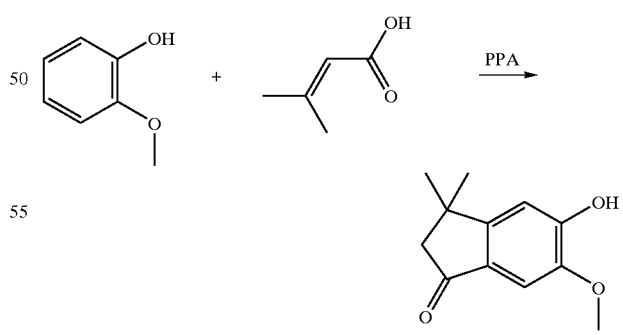

$^1$H NMR (300 MHz, CDCl$_3$): δ 1.15 (s, 6H), 1.26 (s, 6H), 1.40–1.70 (m, 1H), 1.60 (s, 4H), 1.78–1.90 (m, 3H), 3.11 (m, 2H), 3.45–3.84 (m, 2H), 3.70 (s, 3H), 3.89 (s, 2H), 3.93 (m, 1H), 5.29 (br s, 1H), 5.76 (d, 1H), 6.00 (d, 1H), 6.71 (s, 1H), 7.00 (s, 1H), 7.02 (d, 1H), 7.81 (d, 1H), APCI-MS m/z 490.2 (M+H)$^+$.

Example I6

5-(2-Bromo-5-tert-butyl-phenoxy)-furan-2-carboxylic acid N'-(1,3,4-trimethyl-1H-pyrazolo[3,4-b]pyridin-6-yl)-hydrazide Compound I6

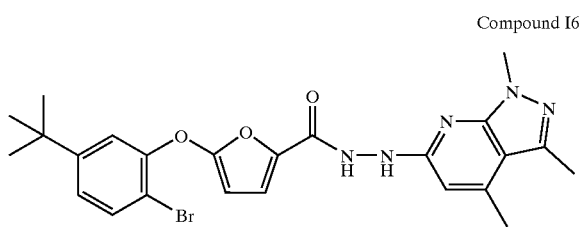

Compound I6 was synthesized according to scheme I from the using the following phenol:

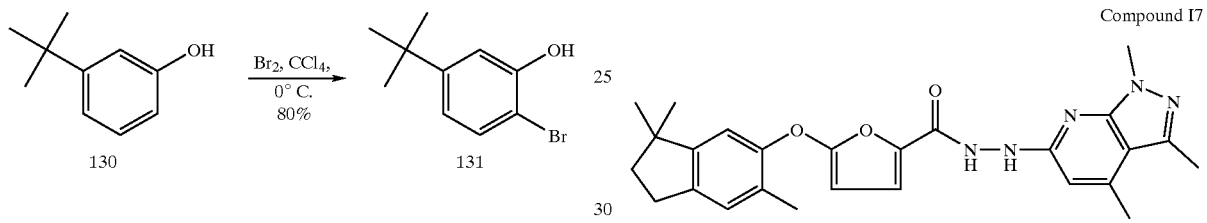

2-Bromo-5-(tert-butyl)phenol compound 131: To an anhydrous carbon tetrachloride (75 mL) solution of 3-tert-butylphenol (130) (199.7 mmol) was added dropwise a solution of an anhydrous carbon tetrachloride (35 mL) of bromine (201 mmol) at 0° C. then allowed to warm up to room temperature. The hydrobromic acid side product was neutralized by aqueous sodium hydroxide solution. The content was diluted with methylene chloride (100 mL) and washed with saturated solution of sodium bicarbonate (3×50 mL), brine (3×50 mL) and water. The organic solution was dried over anhydrous sodium sulfate and brought to dryness. The reaction yielded two products: 6-bromo-3-tert-butylphenyl and 4,6-dibromo-3-tert-butylphenol (9:1), compound 131. $^1$H NMR (300 MHz, CDCl$_3$) δ 61.29 (s, 9H), 2.53 (s, 3H), 2.56 (s, 3H), 3.88 (s, 3H), 5.47 (d, 1H), 6.29 (s, 1H), 7.00 (bs, 1H), 7.20–7.14 (m, 3H), 7.56 (d, 1H), 8.39 (s, 1H).

Example I7

5-(3,3,6-Trimethyl-indan-5-yloxy)-furan-2-carboxylic acid N'-(1,3,4-trimethyl-1H-pyrazolo[3,4-b]pyridin-6-yl)-hydrazide Compound I7

Compound I7 was synthesized according to scheme I where the phenol was synthesized according to the following scheme:

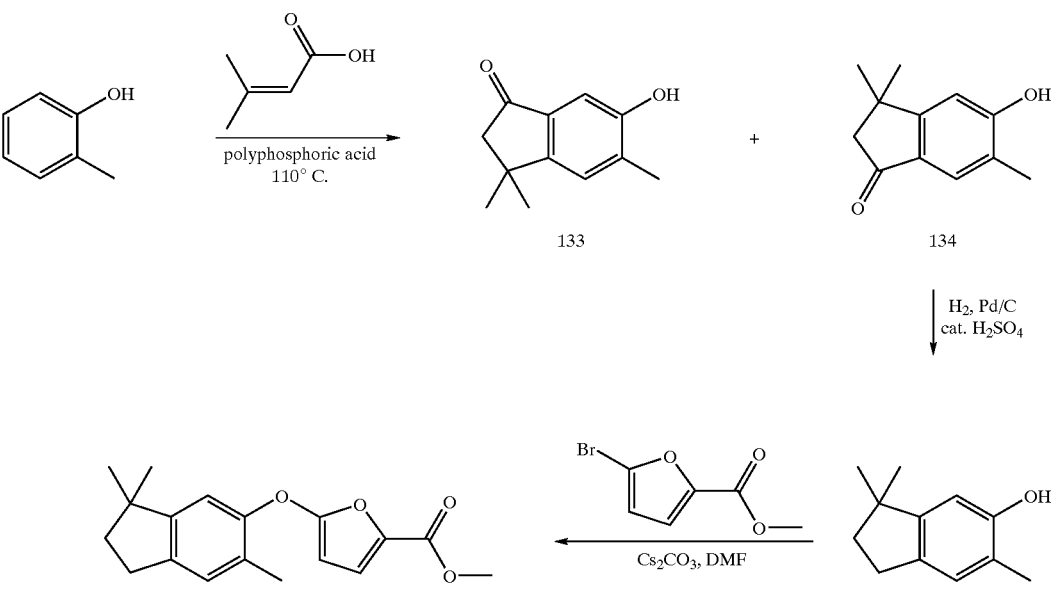

Synthesis of 5-hydroxy-3,3,6-trimethyl-1-indanone (134): o-Cresol (8.2 g, 75.6 mmol), 3,3-dimethylacrylic acid (9.7 g, 96.6 mmol) and polyphosphoric acid (1196.2 g) were combined in a two-necked flask assembled with a condenser. The content was mechanically stirred at 40° C. for 1 h under Nitrogen then gradually heated to 110° C. for 2 h. The reaction was quenched by slowly adding water after the content was cooled down to 40° C. The content was extracted with ethyl acetate (1 L) using a continuous extraction apparatus for two days. The organic layer was neutralized, washed with water and brine. Column chromatography with ethyl acetate:hexane (1:5 then 2:5) afforded light yellow solid of compounds 133 and 134. 5-Hydroxy-3,3,6-trimethyl-1-indanone was recrystalized with ethyl acetate and hexane. (2.6 g of white solid, 15% yield) Ref. Qd419150, Anastasis, P.; Brown, P. E.; *J. Chem. Soc. Perkin Trans.* I. 1, 1982, 2013.

3,3,6-Trimethyl-5-indanol (135): Compound 135 was prepared by the catalytic hydrogenation (40 psi.) of 5-hydroxy-3,3,6-trimethyl-1-indanone (134) (1.54 g, 8.1 mmol) in methanol (13 mL) followed by the addition of sulfuric acid (169 μL). The content was degassed several times with nitrogen before palladium-on-charcoal (10%) was added. The hydrogenation was allowed to react overnight under hydrogen pressure. The reaction content was filtered through celite then brought to dryness. The residue was redissolved in diethyl ether, neutralized with sodium bicarbonate (10%) and washed with water and brine. 3,3,6-Trimethyl-5-indanol was purified with ethyl acetate and hexane (3%, 10% and 30%) to obtain 0.91 g of light yellow solid. (64% yield) Ref. Qd419-161, Wilt, J. W.; Schneider, C. A.; *J. Org. Chem*, 1961, 26, 4196. $^1$H NMR (300 MHz, CDCl$_3$) δ 6 1.22 (s, 6H), 1.94 (dd, 2H, J=7.37, 6.99 Hz), 2.25 (s, 3H), 2.54 (s, 3H), 2.56 (s, 3H), 2.85 (d, 2H, J=7.18 Hz), 3.89 (s, 3H), 5.31 (d, 1H, J=3.59 Hz), 6.31 (s, 1H), 6.84 (s, 1H), 6.99 (bs, 1H), 7.07 (s, 1H), 7.16 (d, 1H, J=3.59 Hz), 8.33 (bs, 1H).

Example I8

5-(1-Bromo-3,5,5,8,8-pentamethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I8

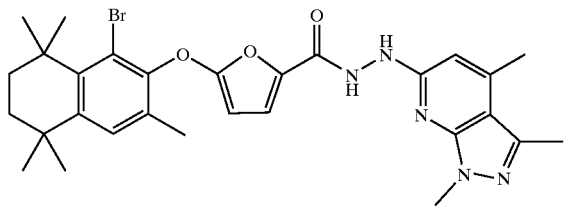

Compound I8 was synthesized according to scheme I where the phenol was synthesized according the the following scheme:

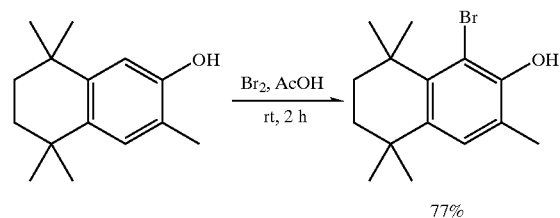

$^1$H NMR (MeOD-d$_4$): δ 1.23(s, 6H), 1.48(s, 6H), 1.58(d, 2H, J=10.76 Hz), 1.67(d, 4H, J=10.58 Hz), 2.15(s, 3H), 2.47(s, 3H), 2.49(s, 3H), 3.74(s, 3H), 5.03(d, 1H, J=3.59 Hz), 6.30(s, 1H), 7.08(d, 1H, J=3.59 Hz), 7.28(s, 1 H).

Example I9

5-(1,3,5,5,8,8-Hexamethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I9

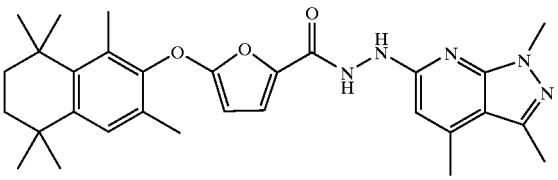

Compound I9 was prepared according to scheme I where the phenol was synthesized according the the following scheme:

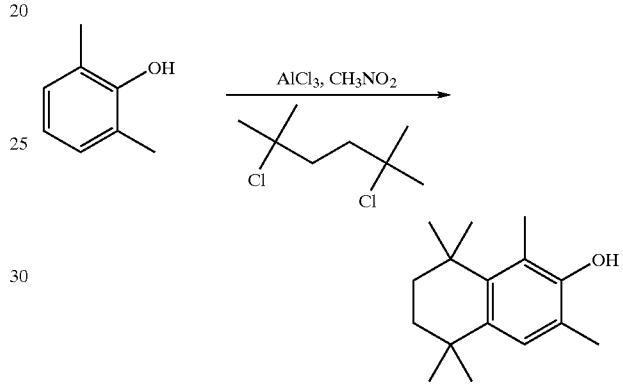

To a one necked round bottom flask 2,6-dimethylphenol (13.88 g, 113.6 mmol), 2,5-dichloro-dimethylhexane were added followed by 460 mL of nitromethane. A clear light yellow solution was cooled in a water bath. Aluminum chloride (15.2 g, 113.9 mmol) was added in small portions into the flask. The reaction mixture changed color from pale yellow to green then brown during the addition of aluminum chloride. The reaction was stirred overnight at room temperature and quenched with water. The content was extracted with ethyl acetate and washed with sodium bicarbonate and brine. Crude product was purified by plug of silica gel 5:95 ethyl acetate:hexane to obtain 19.3 g of 1,3,5,5,8,8-hexamethyl-5,6,7,8-tetrahydronaphthalen-2-ol. $^1$H NMR (300 MHz, CDCl$_3$) δ 1.40 (s, 6H), 1.67(m, 4H), 2.16 (s, 3H), 2.36 (s, 3H), 2.56 (s, 3H), 3.90 (s, 3H), 5.03(d, 1H, J=3.59 Hz), 6.33 (s, 1H), 6.89(d, 1H, J=3.59 Hz), 7.07 (s, 1H), 7.11(d, 1H, J=3.59 Hz), 8.29 (bs, 1H).

Example I10

5-(1-Methoxy-3,8,8-trimethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I10

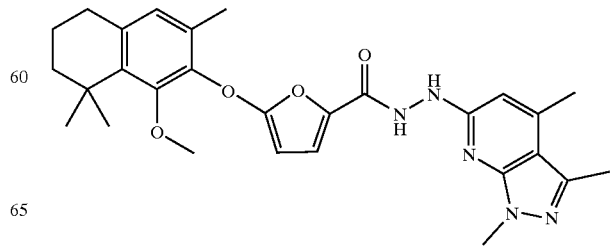

Compound I10 was synthesized according to scheme I wherein the phenol was synthesized according to the following scheme:

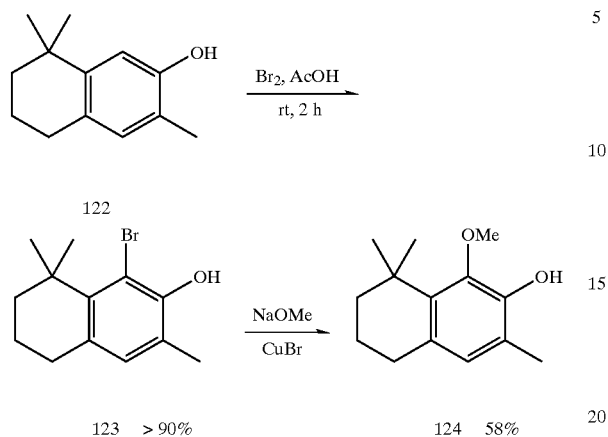

A mixture of 122 (6.8 g, 25.3 mmol), NaOMe (5 M in MeOH, 51 ml, 25.3 mmol), CuBr (0.72 g, 5 mmol) and EtOAc (1.3 g, 15.2 mmol) in 50 ml of MeOH was heated to reflux overnight. Compound 123 (3.2 g) was isolated by a silica gel column chromatography (hexane/EtOAC 15:1 to 9:1). $^1$H NMR (MeOD-$d_4$): δ 1.23(s, 6H), 1.68(s, 2H), 1.79(s, 2H), 2.17(s, 3H), 2.59(m, 6H), 2.75(s, 2H), 3.71(s, 3H), 3.85(s, 3H), 5.38(s, 1H), 6.40(s, 1H), 6.95(s, 1H), 7.24(s, 1H). APCI-MS m/z 504(M+1).

Example I11

5-(1-Bromo-3,8,8-trimethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I11

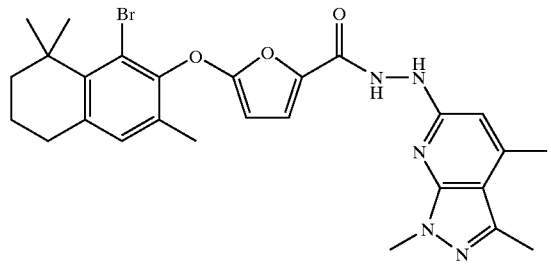

Comopund I11 was synthesized according to scheme I where the phenol was synthesized according to the following procedure:

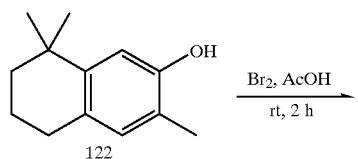

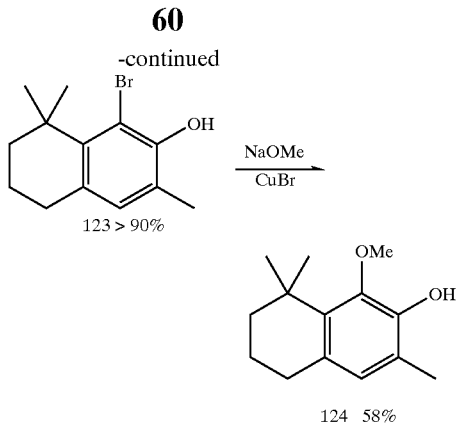

A mixture of 122 (6.8 g, 25.3 mmol), NaOMe (5 M in MeOH, 51 ml, 25.3 mmol), CuBr (0.72 g, 5 mmol) and EtOAc (1.3 g, 15.2 mmol) in 50 ml of MeOH was heated to reflux overnight. Compound 123 (3.2 g) was isolated by a silica gel column chromatography (hexane/EtOAC 15:1 to 9:1). $^1$H NMR (MeOD-$d_4$): δ 1.16(s, 6H), 1.56(m, 2H), 1.76 m, 2H), 2.25(s, 3H), 2.48(m, 6H), 2.68(s, 2H), 3.73(s, 3H), 5.34(d, 1H), 6.28(s, 1H), 7.10(s, 1H), 7.14(s, 1H). APCI-MS m/z 553(M+1).

Example I12

5-(2,4-Dibromo-5-tert-butyl-phenoxy)-furan-2-carboxylic acid N'-(1,3,4-trimethyl-1H-pyrazolo[3,4-b]pyridin-6-yl)-hydrazide Compound I12

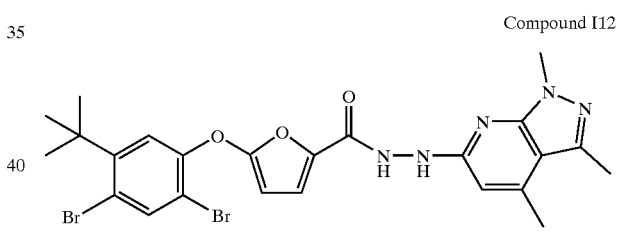

Compound I12 was synthesized according to scheme I where the phenol was synthesized according to the following scheme:

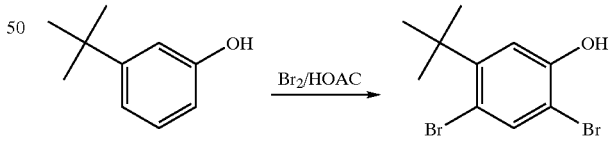

To a solution of 3-tert-butylphenol (1.5 g, 10 mmol) in HOAc (4 mL) was added Br$_2$ (2 mL, 15 mmol). The reaction mixture was stirred at room temperature overnight. It was quenched with ascorbic acid the following day. The crude product was extracted with EtOAc, washed with brine, dried over Na$_2$SO$_4$ and taken to dryness. Column chromatography with EtOAc and hexane (1:10) offered white solid product (0.42 g, 14%). $^1$H NMR (300 MHz, CDCl$_3$): δ 1.46 (s, 9 H), 2.53 (s, 3H), 2.56 (s, 3H), 3.88 (s, 3H), 5.53(d, 1H, J=3.59 Hz), 6.28 (s, 1H), 6.98 (bs, 1H), 7.19(d, 1H, J=3.59 Hz), 7.86 (s, 1H), 8.41 (bs, 1H).

Example I13

N'-(4-Amino-6-cyclopropyl-1,3,5-triazin-2-yl)-5-[(3,3,6-trimethyl-2,3-dihydro-1H-inden-5-yl)oxy]-2-furohydrazide

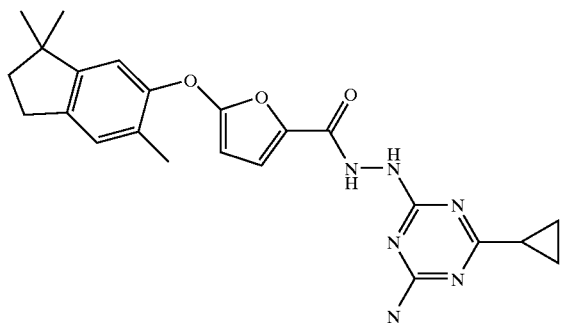

Compound I13

Compound I13 was synthesized according to Scheme I wherein the phenol was synthesized according to the following scheme:

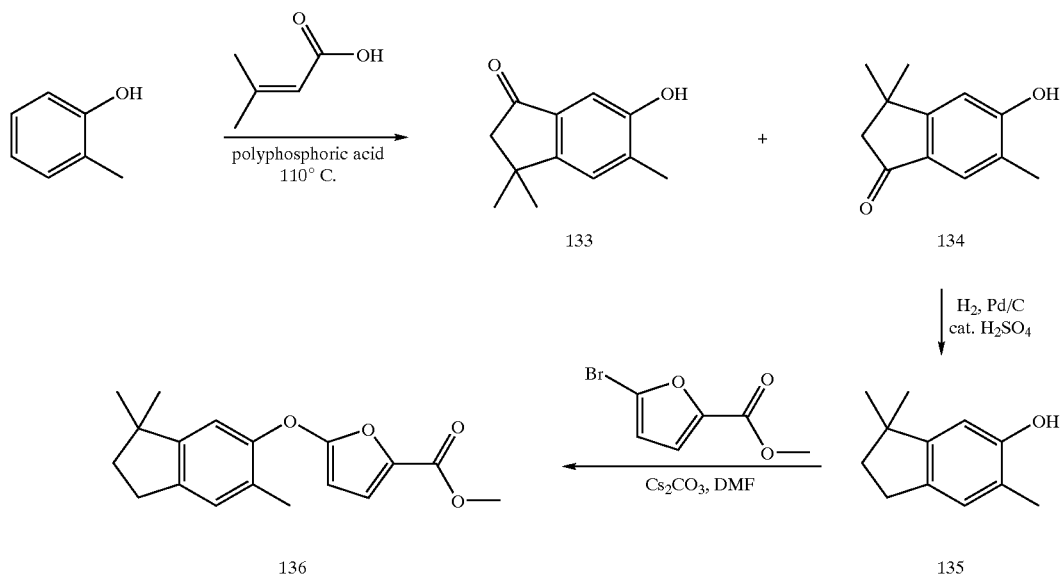

Synthesis of 5-hydroxy-3,3,6-trimethyl-1-indanone (134): o-Cresol (8.2 g, 75.6 mmol), 3,3-dimethylacrylic acid (9.7 g, 96.6 mmol) and polyphosphoric acid (1196.2 g) were combined in a two-necked flask assembled with a condenser. The content was mechanically stirred at 40° C. for 1 h under Nitrogen then gradually heated to 110° C. for 2h. The reaction was quenched by slowly adding water after the content was cooled down to 40° C. It was extracted with ethyl acetate (1 L) using a continuous extraction apparatus for two days. The organic layer was neutralized, washed with water and brine. Column chromatography with ethyl acetate:hexane (1:5 then 2:5) afforded light yellow solid of compounds 133 and 134. 5-Hydroxy-3,3,6-trimethyl-1-indanone was recrystalized with ethyl acetate and hexane. (2.6 g of white solid, 15% yield) Ref. Qd419150, Anastasis, P.; Brown, P. E.; *J. Chem. Soc. Perkin Trans*. I, 1982, 2013. $^1$H NMR: (300 MHz, CDCl$_3$) δ 7.50 (s, 1H), 5.68 (s, 1H), 2.54 (s, 2H), 2.26 (s, 3H) and 1.37 (s, 6H). gcms 191.1 at 10.17 retention time.

3,3,6-Trimethyl-5-indanol (135): Compound 135 was prepared by the catalytic hydrogenation (40 psi.) of 5-hydroxy-3,3,6-trimethyl-1-indanone (134) (1.54 g, 8.1 mmol) in methanol (13 mL) followed by the addition of sulfuric acid (169 μL). The content was degassed several times with nitrogen before palladium-on-charcoal (10%) was added. The hydrogenation was carried out overnight under hydrogen pressure. The reaction was fileterd and the solvents evaportated. The residue was dissolved in diethyl ether, neutralized with sodium bicarbonate (10%) and washed with water and brine. 3,3,6-Trimethyl-5-indanol was purified by column chromatography using ethyl acetate and hexane (3%, 10% and 30%) to obtain 0.91 g of light yellow solid. (64% yield) Ref. Qd419-161, Wilt, J. W.; Schneider, C. A.; *J. Org. Chem*, 1961, 26, 4196. $^1$H NMR: (300 MHz, CDCl$_3$) δ 6.93 (s, 1H), 6.56 (s, 1H), 2.78 (t, 2H), 2.20 (s, 3H), 1.89 (t, 2H) and 1.21 (s, 6H). GCMS 176 at 7.91 retention time. Compound 160 is

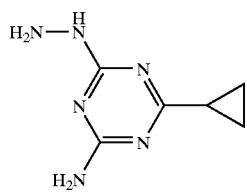

$^1$H NMR: (300 MHz, CDCl$_3$) δ 8 0.88 (bm, 2H), 1.06 (bm, 2H), 1.20 (s, 6H), 1.78 (bm, 1H), 1.92 (t, 2H, J=6 Hz), 2.21 (s, 3H), 2.83 (t, 2H, J=6 Hz), 5.23 (d, 1H, J=3 Hz), 5.53 (bs, 1H), 6.83 (s, 1H), 7.04 (s, 1H) 7.11 (d, 1H, J=3 Hz), 8.61 (bs, 1H).

Example I14

4-(2-{5-[(3,3,6-Trimethyl-2,3-dihydro-1H-inden-5-yl)oxy]-2-furoyl}hydrazino)benzenesulfonamide.

Compound I14

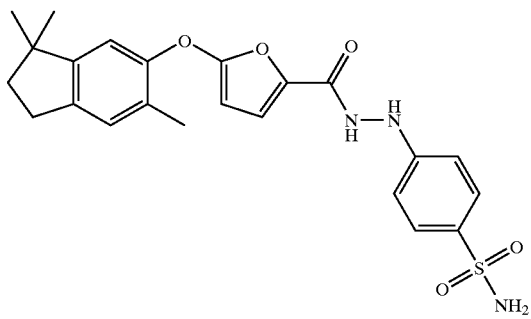

Compound I14 was synthesized according to Scheme I where compound 57 was

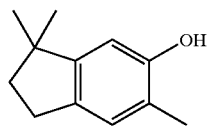

and compound 160 was

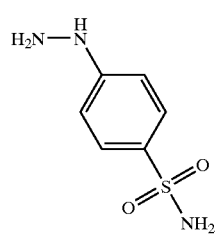

$^1$H NMR: (300 MHz, DMSO-$d_6$) δ 1.18(s, 6H), 1.88(d, 2H, J=7.33 Hz), 2.18(s, 3H), 2.82(t, 2H, J=7.20 Hz), 5.46(d, 1H, J=3.54 Hz), 6.77(d, 2H, J=8.84 Hz), 6.96(s, 1H), 7.03(s, 2H), 7.13(s, 1H), 7.22(d, 1H, J=3.79 Hz), 7.59(d, 2H, J=8.59 Hz), 8.49(s, 1H), 10.25(s, 1H).

Example I15

5-(3,5,5,6,8,8-Hexamethyl-5,6,7,8-tetrahydro-naphthalen-2-yloxy)-furan-2-carboxylic acid N'-(5-methyl-thieno[2,3-d]pyrimidin-4-yl)-hydrazide Compound I15

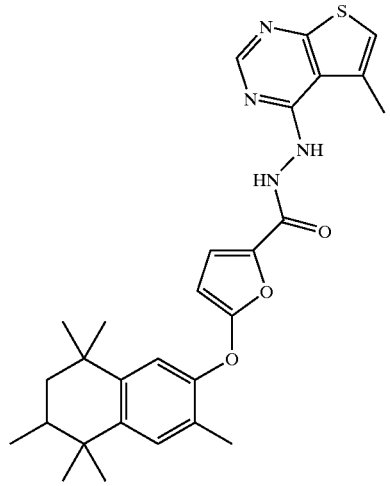

Compound I15 was synthesized according to Scheme I shown above wherein 57 was

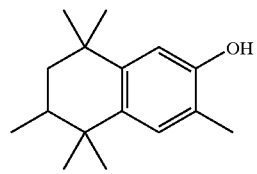

and compound 160 was

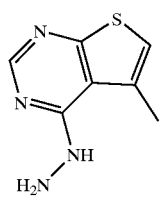

$^1$H (300 MHz, MeOH-$d_4$): δ 0.92 (d, 3H, J=6.8 Hz), 0.98, 1.13, 1.15, 1.24 (4s, 3H each), 1.31–1.35 (m, 1H), 1.56 (t, J=13.2 Hz), 1.70–1.85 (m, 1H), 2.14 (s, 3H), 2.60 (s, 3H), 5.31 (d, 1H, J=3.4 Hz), 6.93(s, 1H), 7.15–7.30 (m, 3H), 8.33 (s, 1H). APCI-MS m/z 505.2 (M+H)$^+$

Example I16

5-(3,5,5,6,8,8-Hexamethyl-5,6,7,8-etrahydro-naphthalen-2-yloxy)-furan-2-carboxylic acid N'-methyl-N'-(6-methyl-pyridazin-3-yl)-hydrazide Compound I16

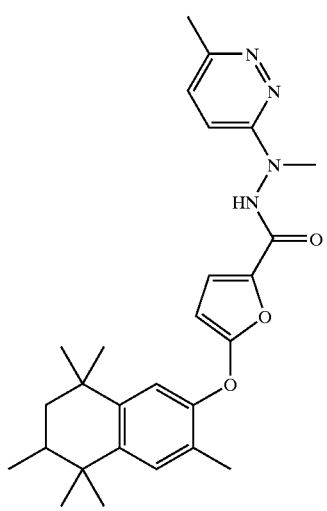

Compound I16 was synthesized according to Scheme I wherein 57 was

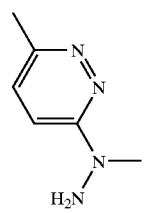

and compound 160 was

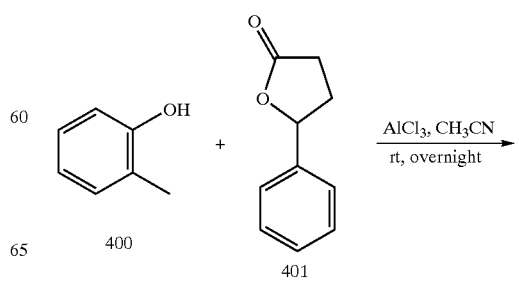

¹H (300 MHz, MeOH-d₄): δ 0.91 (d, 3H, J=6.8 Hz), 0.98, 1.13, 1.15, 1.24 (4s, 3H each), 1.25–1.35 (m, 1H), 1.56 (t, J=13.2 Hz), 1.70–1.85 (m, 1H), 2.12 (s, 3H), 2.58 (s, 3H), 3.35 (s, 3H), 5.29 (d, 1H, J=3.4 Hz), 6.93(s, 1H), 7.20 (d, J=3.4 Hz, 1H), 7.21 (s, 1H), 7.70–7.85 (m, 2H). APCI-MS m/z 463.4 (M+H)⁺

Example I17

5-(5-tert-Butyl-2-methyl-phenoxy)-furan-2-carboxylic acid N'-quinolin-2-yl-hydrazide Compound I17

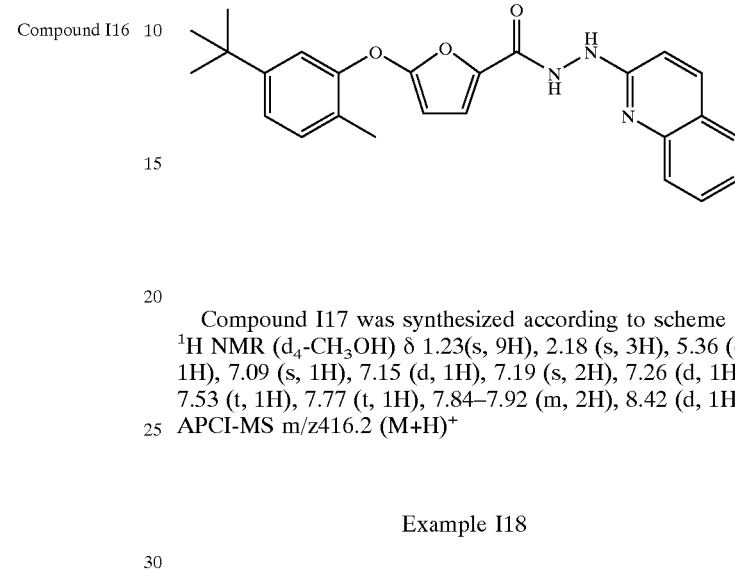

Compound I17 was synthesized according to scheme F. ¹H NMR (d₄-CH₃OH) δ 1.23(s, 9H), 2.18 (s, 3H), 5.36 (d, 1H), 7.09 (s, 1H), 7.15 (d, 1H), 7.19 (s, 2H), 7.26 (d, 1H), 7.53 (t, 1H), 7.77 (t, 1H), 7.84–7.92 (m, 2H), 8.42 (d, 1H); APCI-MS m/z416.2 (M+H)⁺

Example I18

5-(3-Methyl-8-phenyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I18

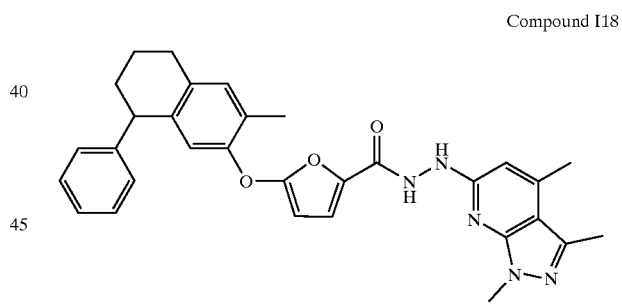

Compound I18 was synthesized according to scheme I where compound 57 was synthesized according to the following scheme:

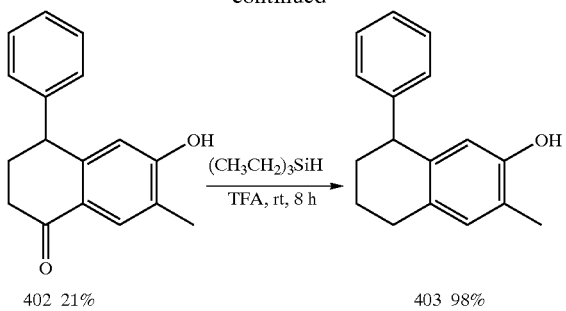

402 21%   403 98%

A solution of 400 (3 g), 401 (4.5 g) and AlCl₃ (5.6 g) was stirred at room temperature overnight. The solution was extracted with EtOAc. Compound 402 (1.5 g) was purified by column (hexane:EtOAc 2:1). To a solution of compound 402 (1.3 g) in TFA (5 ml) was added (CH₃CH₂)₃SiH at 0° C. The solution was stirred for 2 hours. The solution was warmed up to room temperature and stirred overnight. The solution was extracted with EtOAc, concentrated to give compound 403 (1.2 g). ¹H NMR (DMSO-d6): □ 1.58–1.83 (m, 3H), 1.98 (m, 1H), 2.01(s, 3H), 239 (s, 3H), 2.42 (s, 3H), 2.68–2.72 (m, 2H), 3.65 (s, 3H), 4.02 (t, 1H), 5.6 (d, 1H), 6.17 (s, 1H), 6.6 (s, 1H), 6.8 (s, 1H), 7.02 (d, 2H), 7.14 (m, 1H), 7.20–7.24 (m, 3H), 8.88 (s, 1H), 10.1 (s, 1H) APCI-MS m/z 522.3 (M+H)

Example I19

5-(5-tert-Butyl-2-methyl-phenoxy)-furan-2-carboxylic acid N'-(1,3,4-trimethyl-1H-pyrazolo[3,4-b]pyridin-6-yl)-hydrazide Compound I19

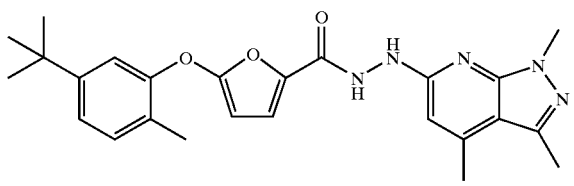

Compound I19 was synthesized according to scheme I. ¹H NMR (CH₃OH-d₄): δ 1.29 (s, 9H), 2.25 (s, 3H), 2.56 (s, 3H), 2.58 (s, 3H), 3.83 (s, 3H), 5.41 (d, 1H), 6.39 (s, 1H), 7.13 (s, 1H), 7.22 (d, 1H), 7.23 (m, 2H); APCI-MS m/z 448.2 (M+H)⁺

Example I20

5-(3,5,5,6,8,8-Hexamethyl-5,6,7,8-tetrahydro-naphthalen-2-yloxy)-furan-2-carboxylic acid N'-quinolin-2-yl-hydrazide Compound I20

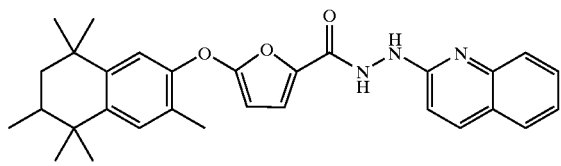

Compound 120 was synthesized according to scheme I. ¹H (300 MHz, CDCl₃): □ 0.97 (d, 3H, J=6.8 Hz), 1.06, 1.22, 1.24, 1.33 (4s, 3H each), 1.37–1.40 (m, 1H), 1.63 (t, J=13.2 Hz), 1.80–1.91 (m, 1H), 2.26 (s, 3H), 5.33 (d, 1H, J=3.4 Hz), 6.93 (d, J=6.5 Hz, 1H), 7.16 (d, 1H, J=3.4 Hz), 7.21 (s, 1H), 7.31 (t, J=5.1 Hz, 1H), 7.58 (t, J=5.1 Hz, 1H), 7.65 (d, J=6.7 Hz, 1H), 7.78 (d, J=6.7 Hz, 1H), 7.92 (d, J=6.7 Hz, 1H). APCI-MS m/z 484.2 (M+H)⁺

Example I21

N'-(1,3,4-trimethyl-1H-pyrazolo[3,4-b]pyridin-6-y)-5-[(3,8,8-trimethyl-5,6,7,8-tetrahydro-2-naphthalenyl)oxy]-2-furohydrazide:

Compound I21

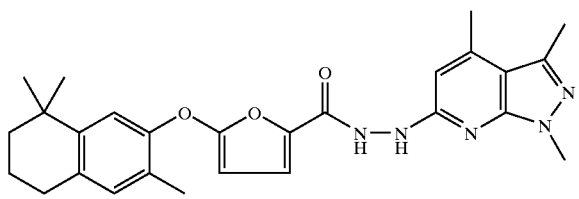

Compound I21 was synthesized according to Scheme I. ¹H NMR (300 MHz, CD₃OD): 7.46 (1H, d, J=3.6 Hz); 7.32 (1H, s); 7.22 (1H, s); 6.62 (1H, s); 5.58 (1H, d, J=3.6 Hz); 4.07 (3H, s); 2.98 (2H, t, J=6.23 Hz); 2.83 (3H, s); 2.81 (3H, s); 2.45 (3H, s); 2.10–1.89 (4H, m); 1.49 (6H, s), APCI-MS m/z 474.2 (M+H)⁺.

Example I22

5-(4-Bromo-3,3,6-trimethyl-indan-5-yloxy)-furan-2-carboxylic acid N'-(1,3,4-trimethyl-1H-pyrazolo[3,4-b]pyridin-6-yl)-hydrazide Compound I22

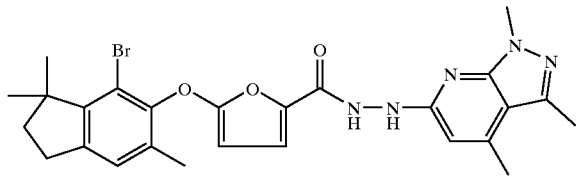

Compound I22 was synthesized according to Scheme I where compound 57 was synthesized according to the following scheme:

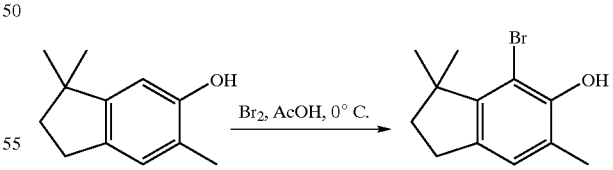

To a 25 mL one necked round bottom flask, 3,3,6-trimethylindan-5-ol was dissolved in acetic acid (10 mL). The solution was cooled down to 0° C. followed by slow addition of bromine (290 μL, 5.65 mmol). The reaction was slowly warmed up to room temperature. After 3 h of stirring, the reaction was completed. Excess acetic acid was removed by rotavap, and the residue was quenched with ascorbic acid solution. The content was extracted with sodium bicarbonate and brine. Plugged column with silica gel 5:95 ethyl acetate-:hexane gave colorless oil, 4-bromo-3,3,6-trimethylindan-5- ol (82% yield). $^1$H NMR (300 MHz, CDCl$_3$): δ 1.42 (s, 6H), 1.98(dd, 2H, J=15.11, 7.55 Hz), 2.24 (s, 3H), 2.54 (s, 3H), 2.57 (s, 3H), 2.85(d, 2H, J=7.55 Hz), 3.89 (s, 3H), 5.12(d, 1H, J=3.40 Hz), 6.31 (s, 1H), 6.95(m, 1H), 7.01 (s, 1H), 7.12(d, 1H, J=3.40) 8.34 (bs, 1H).

Example I23

5-(4-Chloro-5-isopropyl-2-methyl-phenoxy)-furan-2-carboxylic acid N'-(1,3,4-trimethyl-1H-pyrazolo[3,4-b]pyridin-6-yl)-hydrazide Compound I23

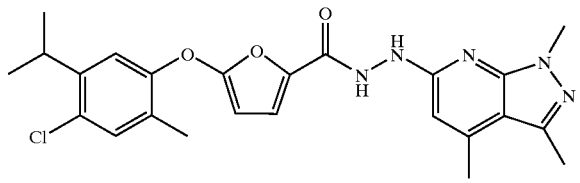

The synthesis of compound I23 was synthesized according to scheme I where compound 57 was 5-(4-chloro-5-isopropyl-2-methylphenoxy)-2-furoic acid (88.4 mg) to yield the product (70.7 mg, 50.5%, scheme 8). $^1$H NMR (DMSO-d$_6$) 0.38 (s, 3H), 0.40 (s, 3H), 1.44 (s, 3H), 1.74 (s, 3H), 1.76 (s, 3H), 3.00 (s, 3H), 4.68(d, 1H, J=3.78 Hz), 5.56 (s, 1H), 6.27 (s, 1H), 6.41(d, 1H, J=3.78 Hz), 6.51 (s, 1H).

Example I24

5-(4-Bromo-3,3,6-trimethyl-1,3-dihydro-isobenzofuran-5-yloxy)-furan-2-carboxylic acid N'-(1,3,4-trimethyl-1H-pyrazolo[3,4-b]pyridin-6-yl)-hydrazide Compound I24

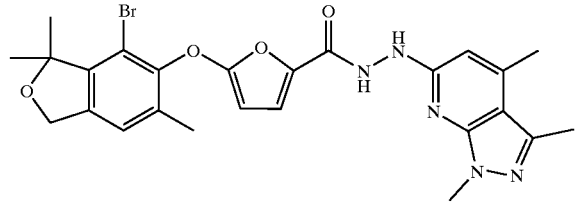

Compound I24 was synthesized according to scheme I. $^1$H (300 MHz, MeOH-d$_4$): □ 1.59, 1.61 (2s, 3H each), 2.31, 2.58, 2.56, 3.83 (4s, 3H each), 5.02 (s, 2H), 5.02 (d, 1H, J=3.59 Hz), 6.39 (s, 1H), 7.15–7.22 (m, 2H). MS m/z 540.2 M$^+$, 542.1(M+2H)$^+$

Example I25

5-(3-Methoxy-1,5,5,8,8-pentamethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I25

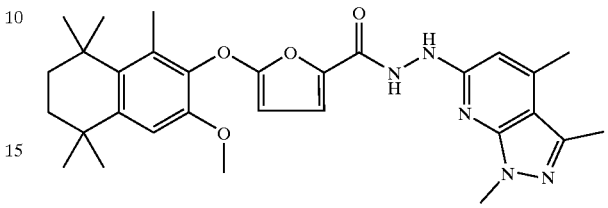

Compound I25 was synthesized according to scheme I wherein compound 57 was synthesized according to the following scheme:

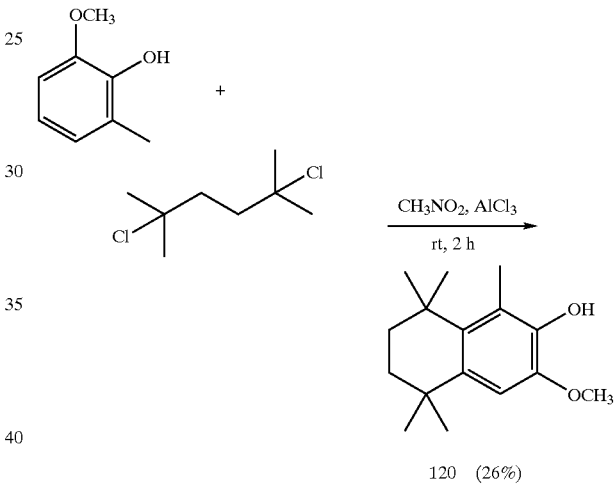

$^1$H NMR (CDCl$_3$): δ 1.31 (s, 6H), 1.387 (s, 6H), 1.67 (s, 4H), 2.39 (s, 3H), 2.55 (s, 3H), 2.57 (s, 3H), 3.79 (s, 3H), 3.98 (s, 3H), 5.11 (d, 1H), 6.41 (S, 1H), 5.53 (bs, 1H), 6.80 (s, 1H), 7.14 (d, 1H), 8.42 (s, 1H), 9.60 (s. 1H). APCI-MS m/z 532.3 (M+1).

Example I26

5-(7-Chloro-4,4-dimethyl-1,2,3,4-tetrahydro-quinolin-6-yloxy)-furan-2-carboxylic acid N'-(1,3,4-trimethyl-1H-pyrazolo[3,4-b]pyridin-6-yl)-hydrazide Compound I26

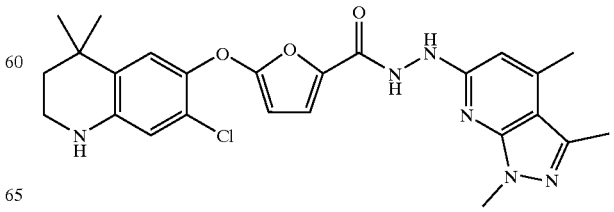

Compound I26 was synthesized from compound I1 by the following reaction.

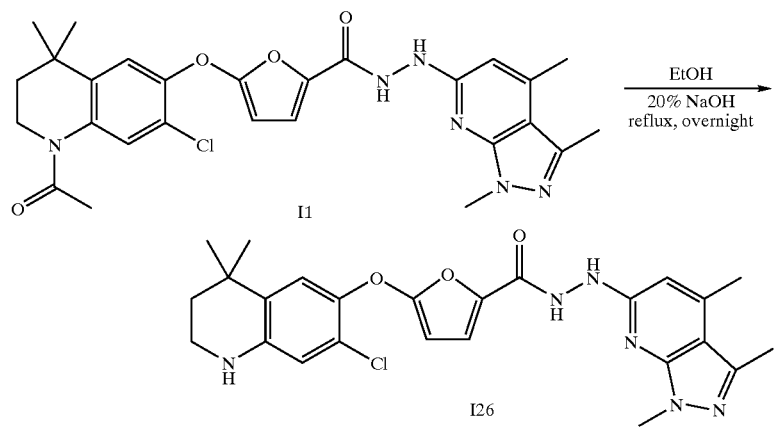

A solution of I1 (1.0 g) in 20% NaOH-EtOH was heated to reflux overnight to yield compound 126 (635 mg). $^1$H NMR (MeOH-d$_4$): δ 1.28 (s, 6H), 1.74 (t, 2H), 2.56 (s, 3H), 2.66 (s, 3H), 3.82 (s, 3H), 5.32 (d, 1H), 6.38 (s, 1H), 6.70 (s, 1H), 7.17 (d, 1H), 7.19 (s, 1H). APCI-MS m/z 495.2 (M+1).

Example I27

5-(7-Chloro-1,4,4-trimethyl-1,2,3,4-tetrahydro-quinolin-6-yloxy)-furan-2-carboxylic acid N'-(1,3,4-trimethyl-1H-pyrazolo[3,4-b]pyridin-6-yl)-hydrazide Compound I27

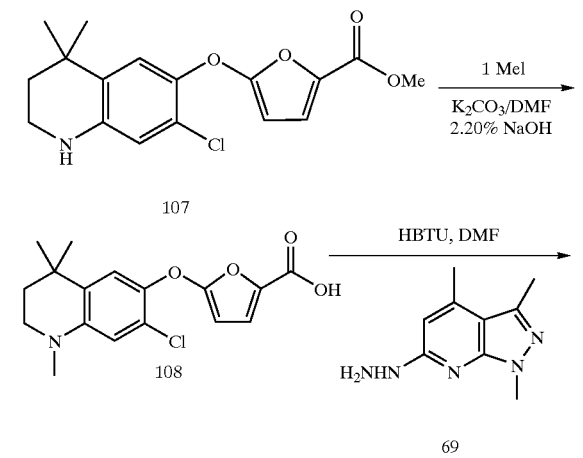

Compound I27 was synthesized according to scheme I wherein compound 107 was alkylated according the the following scheme:

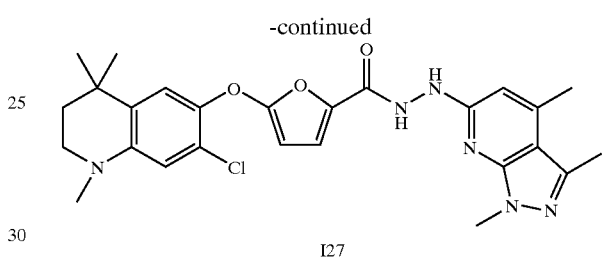

-continued

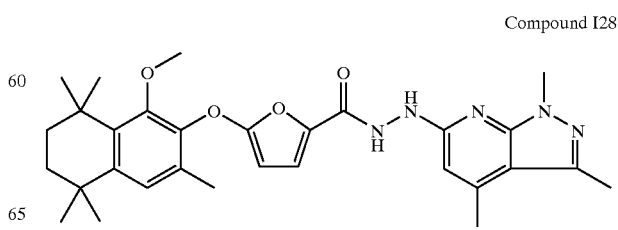

A solution of compound 107 (600 mg, MeI (1 ml) and K$_2$CO$_3$ (2 eq.) in 5 ml of DMF was heated to 80° C. for 5 hours. The solution was extracted with EtOAc. The concentrated organic layer was treated with a mixture solvent of 20% NaOH/MeOH/THF (1:1:1) at r.t for 3 hours. 300 mg of compound 108 was obtained. Compound 108 (100 mg) was coupled with 6-hydrazino-1,3,4-trimethyl-1H-pyrazolo[3,4-b]pyridine (58 mg) by HBTU (171 mg and Et$_3$N (61 mg) in DMF at rt. to give Compound I27 (32 mg). $^1$H NMR (MeOH-d$_4$): δ 1.07 (s, 6H), 1.58 (t, 2H), 2.38 (s, 3H), 2.40 (s, 3H), 2.73 (s, 3H), 3.08 (t, 2H), 3.65 (s, 3H), 5.08 (d, 1H), 6.21 (s, 1H), 6.45 (s, 1H), 6.96 (s, 1H), 7.01 (d, 1H). APCI-MS m/z 509.2 (M+1).

Example I28

5-(1-Methoxy-3,5,5,8,8-pentamethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I28

Compound I28 was synthesized according to scheme I where the synthesis of compound 57 is shown below:

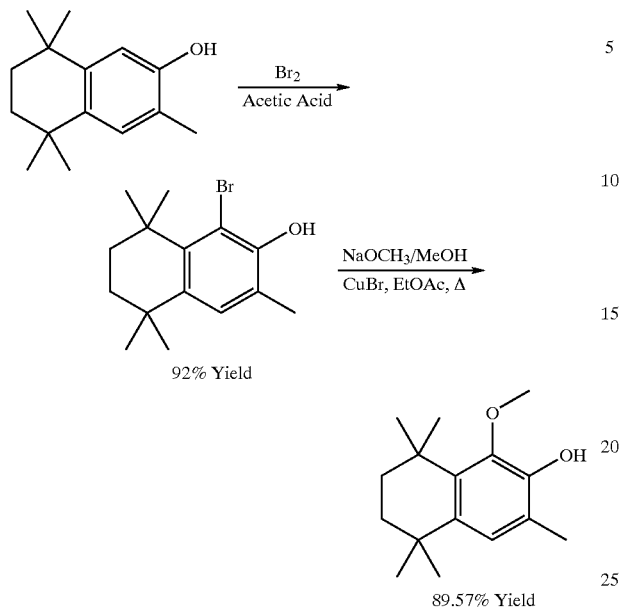

92% Yield 89.57% Yield

In 500 mL roundbottom flask, 3,5,5,8,8-pentamethyl-5,6,7,8-tetrahydro-2-naphthalenol (10.2 g, 46.72 mmol) was dissolved in 100 mL Acetic Acid. To this solution Bromine (8.2 g, 51.39 mmol) was added. The reaction was stirred at room temperature for 20 minutes. The reaction mixture was poured into water and extracted with ethyl acetate. The separated organic layer was washed with brine, dried over magnesium sulfate and concentrated. The crude product was purified by silica gel chromatography eluted with hexane to yield 1-Bromo-3,5,5,8,8-pentamethyl-5,6,7,8-tetrahydro-2-naphthalenol (12.8 g, 92% yield).

To the solution of 1-Bromo-3,5,5,8,8-pentamethyl-5,6,7,8-tetrahydro-2-naphthalenol (12.8 g, 43.06 mmol) and sodium methoxide in methanol (5.0M) was added CuBr (1.24 g, 8.61 mmol) followed by ethyl acetate (2.5 mL). The reaction was stirred and heated to reflux for 16 hours. The reaction mixture was cooled to room temperature then poured into water and extracted with ethyl acetate. The separated organic layer was washed with brine, dried over magnesium sulfate and concentrated to yield 1-Methoxy-3,5,5,8,8-pentamethyl-5,6,7,8-tetrahydro-2-naphthalenol (9.58 g, 89.57%). $^1$H NMR (CDCl$_3$): δ 1.27 (s, 6H), 1.36 (s, 6H), 1.63–1.67 (m, 4H), 2.21 (s, 3H), 2.53 (s, 3H), 2.57 (s, 3H), 3.87 (s, 3H), 3.90 (s, 3H), 5.15 (d, 1H), 6.30 (s, 1H), 6.94 (s, 1H), 6.98 (s, 1H), 7.13 (d, 1H), 8.35 (s, 1H). APCI-MS m/z 532 (M+1).

Example I29
5-(1-Hydroxy-3,5,5,8,8-pentamethyl-5,6,7,8-tetrahydro-naphthalen-2-yloxy)-furan-2-carboxylic acid N'-(1,3,4-trimethyl-1H-pyrazolo[3,4-b]pyridin-6-yl)-hydrazide Compound I29

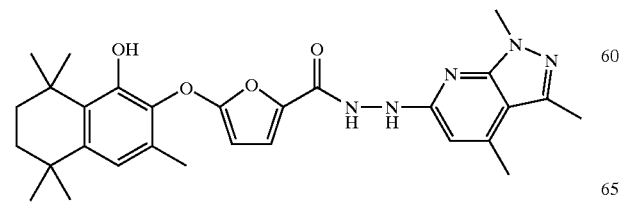

Compound I29 was synthesized from compound I28 according to the following scheme:

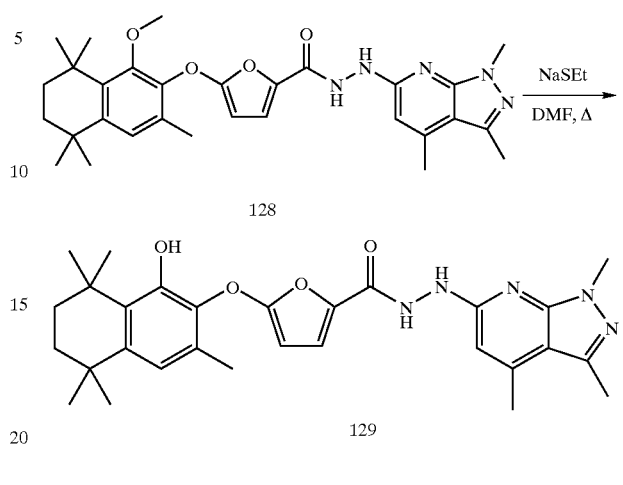

128

129

In a 50 mL round bottom flask, 5-[(1-methoxy-3,5,5,8,8-pentamethyl-5,6,7,8-tetrahydro-2-naphthalenyl)oxy]-N'-(1,3,4-trimethyl-1H-pyrazolo[3,4-b]pyrimidin-6-yl)-2-furohydrazide (200 mg, 376 mmol) was dissolved in DMF (2.0 mL). To the solution, 124 mg (1.51 mmol) of sodium ethanethiolate was added. The mixture of heated to 100° C. for overnight. The reaction mixture was poured into water, acidified with acetic acid, and extracted with ethyl acetate. The separated organic layer was washed with brine, dried over magnesium sulfate and concentrated. The crude product was purified by HPLC, eluting with acetonitrile/water to yield 5-[(1-hydroxy-3,5,5,8,8-pentamethyl-5,6,7,8-tetrahydronaphthalen-2-yl)oxy]-N'-(1,3,4-trimethyl-1H-pyrazolo[3,4-b]pyridin-6-yl)-2-furohydrazide. $^1$H NMR (MeOD-d$_4$): δ 1.19 (s, 6H), 1.34 (s, 6H), 1.55–157 (m, 4H), 2.03 (s, 3H), 2.44 (s, 3H), 2.47 (s, 3H), 3.69 (s, 3H), 5.08 (d, 1H), 6.19 (s, 1H) 6.72 (s, 1H), 7.18 (d, 1H), 8.64 (s, 1H), 8.99 (s, 1H), 10.10 (s, 1H). APCI-MS m/z 518.3 (M+1).

Example I30

AXC08716-N-Methyl-N-(4-methyl-3-{5-[N'-(1,3,4-trimethyl-1H-pyrazolo[3,4-b]pyridin-6-yl)-hydrazinocarbonyl]-furan-2-yloxy}-phenyl)-acetamide Compound I30

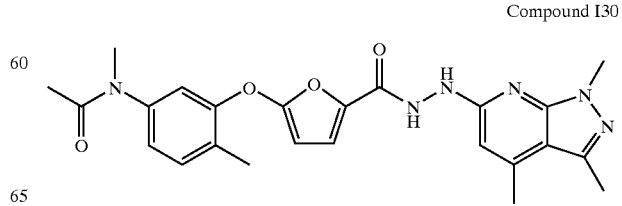

Compound I30 was synthesized according to scheme I where compound 57 was synthesized according to the following scheme and the final product was synthesized by a coupling reaction using HBTU.

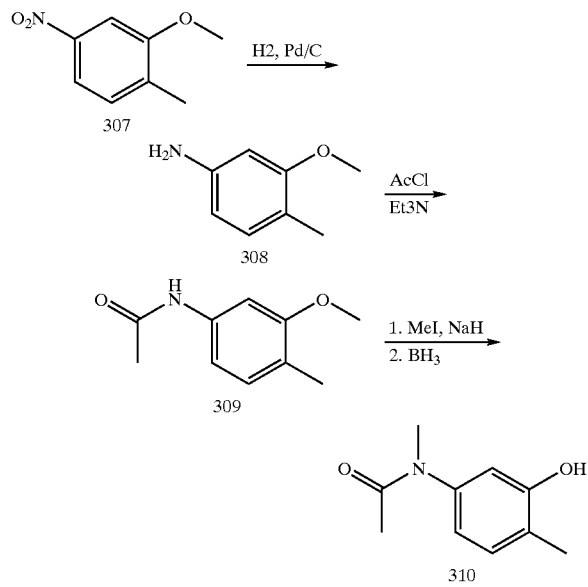

A solution of 307 (10 g, 60 mmol) in EtOH was hydrogenated (50 psi) overnight to give 308 (8 g, 97.6%). To a solution of 308 (6.3 g, 46 mmol) and Et$_3$N (4.7 g, 46 mmol) in 100 mL dry THF was added AcCl (3.6 g, 46 mmol) at 0° C. The mixture was stirred at rt. for 15 min. Diluted with water, extracted with hexane, Dried over MgSO$_4$, removed hexane to give 5.5 g (67%) of 309.

To a solution of 309 in anhydrous THF was added 1.5 eq. NaH (85%). The mixture was stirred for 5 min. 2 eq. of MeI was added followed by stiring overnight. Diluted with water, extracted with hexane, dried over MgSO$_4$. After removing hexane, the residue was dissolved in dry CH$_2$Cl$_2$, 1.5 eq. BH$_3$ in THF was added at 0° C. Stirred overnight, 100 mL water was added. Organic layer was dried over MgSO$_4$, concentrated to give crude product 310, which purified by column chromatography (Hexane/EtOAc=1/1). $^1$H NMR (CDCl$_3$): δ 1.78(s, 3H), 2.25(s, 3H), 2.38(s, 3H), 2.45(s, 3H), 3.13(s, 3H), 3.77(s, 1H), 5.39(d, J=3.0 Hz, 1H), 6.15(s, 1H), 6.81 (s, 1H), 6.89(dd, J=2.1 Hz, J=8.1 Hz, 1H), 7.1 (s, J=3.0 Hz, 1H), 7.17–7.23(m, 2H), 8.45(s, 1H). LC/MS (M+H)$^+$: 463.

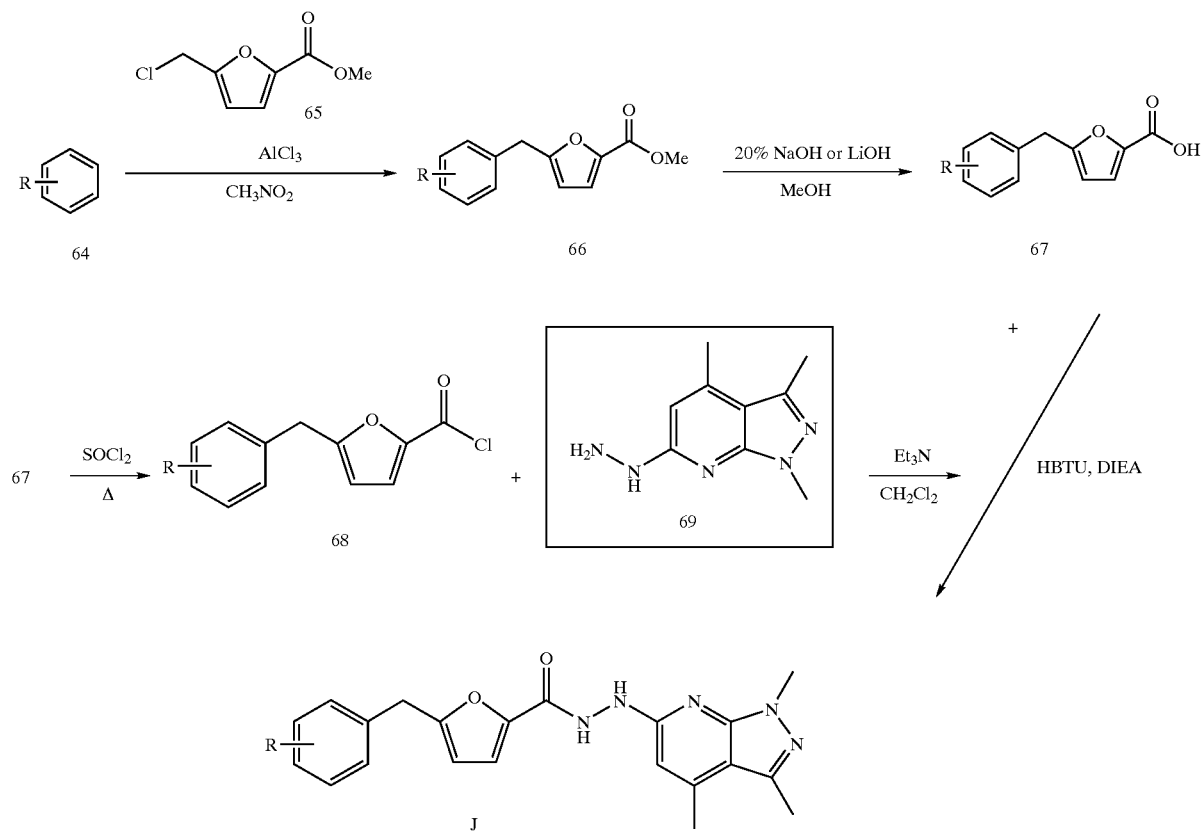

Scheme J

To a solution containing 64 (16.88 g, 97.75 mmol) and methyl 5-(chloromethyl)-2-furoate, 65, (14.22 g, 81.46 mmol) in nitromethane (300 mL, 0.3 M) is added slowly aluminum trichloride (9.56 g, 97.75 mmol). The solution is stirred at room temperature for 4 hours. The reaction is quenched with water (0° C.) and the crude product is extracted with ethyl acetate. The separated organic layer is washed with brine, dried over magnesium sulfate and concentrated. The crude product is purified by silica gel chromatography using hexane/ethyl acetate (19:1 v/v) to yield 66, (21.56 g, 85.8% yield).

To a solution of 66, in methanol (75 mL), a solution of 20% NaOH in water is added. The reaction mixture is stirred overnight. After completion as judged by TLC, the solution is washed with diethyl ether. The aqueous layer is acidified with 4N HCl to pH 2. The crude mixture is extracted with ethyl acetate, and concentrated to afford 67, (8.27 g, 86.66% yield).

A solution of 67, is made in 10 mL thionyl chloride ($SOCl_2$). The reaction is heated to 100° C. for 30 minutes. The crude mixture is concentrated and co-evaporated with toluene to yield 1.05 g of 68. Compound 68, (0.200 g, 0.639 mmol) in $CH_2Cl_2$ (0.3 M) is added to 69 (0.122 g, 0.639 mmol) followed by triethylamine (0.129 g, 1.277 mmol). Reaction is stirred at room temperature overnight. The crude product is purified by silica gel chromatography eluted with hexane/ethyl acetate (2:1) to yield J. (42.6 mg, 14% yield).

Alternately, compounds may be synthesized by a coupling reaction between compund 67 and compound 69 using HBTU. The procedure is as follows: To a solution of 67 (0.33 g, 1 mmol), HBTU (0.45 g, 1.2 mmol) in 10 mL DMF is added 0.5 ml $Et_3N$. The mixture is stirred at rt. for 30 min. 1,3,4-trimethyl-1H-pyrazolo[3,4-b]pyrid-6-ylhydrazine (305, 0.191 g, 1 mmol) is added to above solution, and the mixture is stirred overnight. 50 mL EtOAc is added and washed with water. Organic layer is dried with $MgSO_4$. Concentration gave crude product, which is purified by HPLC.

Example J1

5-(3-chloro-6-methoxy-2,4-dimethyl benzyl)-N'-(1,3,4-trimethyl-(H-pyrazolo[3,4-b]pyridin-6-yl-2-furohydrazide Compound J1

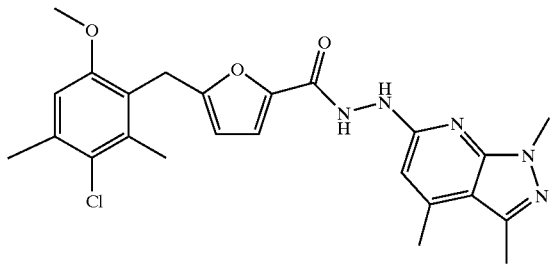

Compound J1 was synthesized according to Scheme J, wherein compound 64 was synthesized according to the following scheme.

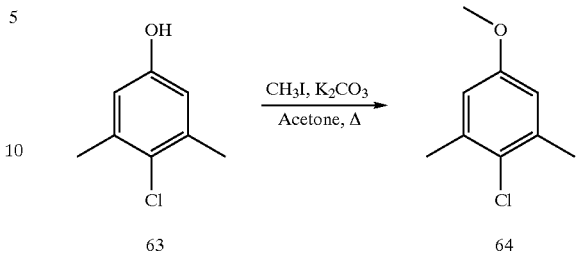

63

64

To a 1 L round-bottom flask 4-chloro-3,5-dimethylphenol 63 (20 g, 127.7 mmol) and acetone (500 mL, 0.2 M) was placed. To this solution were added potassium carbonate (35.3 g, 255.4 mmol) and iodomethane (63.44 g, 447 mmol). The reaction was stirred and heated to reflux for 3 hours. The reaction mixture was poured into water and extracted with ethyl acetate. The separated organic layer was washed with brine, dried over magnesium sulfate and concentrated. The crude product was purified by silica gel chromatography eluted with hexane to yield 4-chloro-3,5-dimethylphenyl methyl ether 64 (16.88 g, 77%). $^1$HNMR (300 MHz, $CDCl_3$): δ 2.41 (s, 3H), 2.59 (s, 3H), 2.62 (s, 3H), 2.68 (s, 3H), 3.82 (s, 3H), 4.06 (s, 3H), 4.11 (s, 2H), 5.97 (d, 1H), 6.44 (s, 1H), 6.70 (s, 1H), 7.15 (d, 1H), 8.41 (brd, 1H), 10.31 (brd, 1H), APCI-MS m/z 468.2 $(M+H)^+$.

Example J2

5-(3-Bromo-2,4,6-trimethylbenzyl-N'-(1,3,4-trimethyl-1H-pyrazolo[3,4-b]pyridin-6-yl)-2-furohydrazide Compound J2

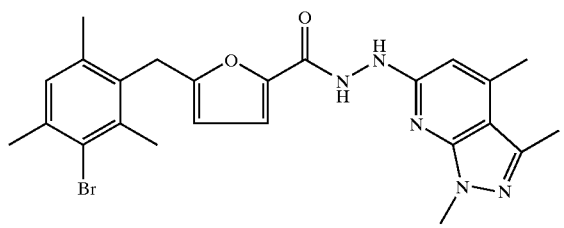

Compound J2 was synthesized according to scheme J. $^1$H NMR (300 MHz, DMSO-$d_6$): δ 2.08 (s, 3H), 2.28 (s, 3H), 2.32 (s, 3H), 2.42 (s, 3H), 2.46 (s, 3H), 3.70 (s, 3H), 4.12 (s, 2H), 6.06 (d, 1H, J=3 Hz), 6.22 (s, 1H), 7.10 (s, 1H), 7.16 (d, 1H, J=3 Hz), 8.72 (s, 1H), 10.21 (s, 1H), APCI-MS m/z 496 $(M+H)^+$.

Compound J3: 5-(Mesitylmethyl)-N'-(1,3,4-trimethyl-1H-pyrazolo[3,4-b]pyridin-6-yl)-2-furohydrazide:

Compound J3

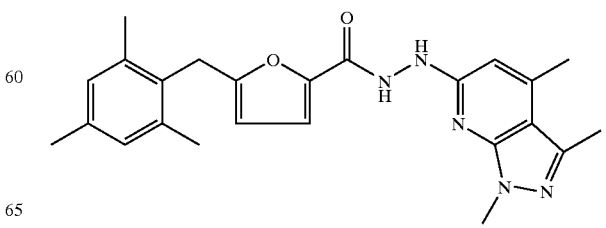

Compound J3 was synthesized according to scheme J. $^1$H NMR (300 MHz, DMSO-$d_6$): δ 2.07 (s, 3H), 2.21–2.27 (m, 9H), 2.46 (s, 3H), 3.70 (s, 3H), 3.99 (s, 2H), 6.00 (d, 1H, J=3 Hz), 6.22 (s, 1H), 6.87 (s, 2H), 7.16 (d, 1H, J=3 Hz), 8.72 (s, 1H), 10.19 (s, 1H), APCI-MS m/z 418 (M+H)$^+$.

Example J4

5-(4,5-dimethoxy-2-methylbenzyl)-N'-(3,4-dimethyl-1H-pyrazolo[3,4-b]pyrin-6-yl)-2-furohydrazide Compound J4

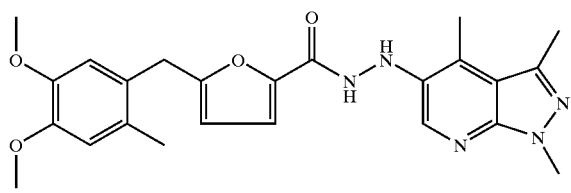

Compound J4 was synthesized according to scheme J. $^1$H NMR (300 MHz, CDCl$_3$): δ 7.10 (1H, d, J=3.4 Hz); 6.70 (1H, s); 6.68 (1H, s); 6.26 (1H, s); 6.02 (1H, d, J=3.4 Hz); 3.95 (2H, s); 3.86 (6H, s); 3.83 (3H, s); 2.55 (3H, s); 2.50 (3H, s); 2.26 (3H, s), APCI-MS m/z 450.2 (M+H)$^+$.

Example J5

5-(2,3,4,5,6-Pentamethyl benzyl)-N'-(1,3,4-trimethyl-1H-pyrazolo[3,4-b]pyridin-6-yl)-2-furohydrazide Compound J5

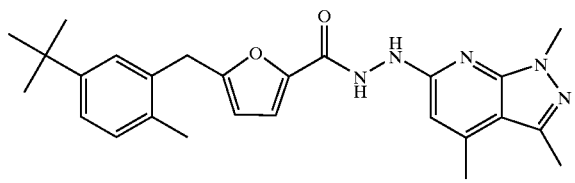

Compound J5 was synthesized according to scheme J. $^1$H NMR (300 MHz, CDCl$_3$): δ 2.03–2.06 (m, 15H), 2.34 (s, 3H), 2.36 (s, 3H), 3.68 (s, 3H), 3.90 (s, 2H), 5.71 (d, 1H, J=3 Hz), 6.10 (s, 1H), 6.75 (s, 2H), 6.85 (d, 1H, J=3 Hz), 8.25 (s, 1H), APCI-MS m/z 446 (M+H)$^+$.

Example J6

5-(2,5-Dimethoxy-benzyl)-furan-2-carboxylic acid N'-(1,3,4-trimethyl-1H-pyrazolo[3,4-b]pyridin-6-yl)-hydrazide Compound J6

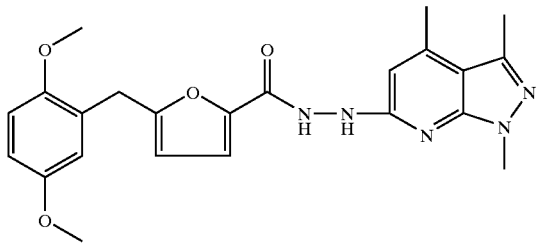

Compound J6 was synthesized according to scheme J. $^1$H NMR (300 MHz, CDCl$_3$): δ 2.23 (s, 3H), 2.43 (s, 3H), 3.64 (s, 3H), 3.69 (s, 3H), 3.73 (s, 3H), 3.88 (s, 2H), 6.01 (d, 1H, J=3 Hz), 6.07 (s, 1H), 6.65–6.74 (m 3H), 7.05 (d, 1H, J=3 Hz), 7.83 (s, 1H), 8.95 (s, 1H), APCI-MS m/z 436 (M+H)$^+$.

Example J7

5-[5-(tert-butyl)-2-methylbenzyl]-N'-(1,3,4-trimethyl-1H-pyrazolo[3,4-b]pyridin-6-yl)-2-furohydrazide Compound J7

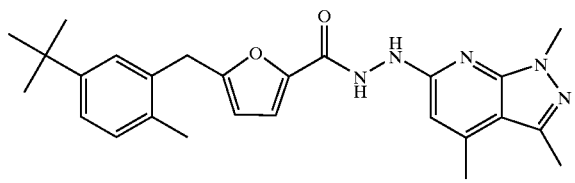

Compound J7 was synthesized according to scheme J. $^1$H NMR (300 MHz, CD$_3$OD): δ 7.12 (1H, d, J=8.0 Hz), 7.06 (1H, d, J=3.4 Hz); 7.62 (1H, d, J=7.55 Hz); 6.24 (1H, s); 5.98 (1H, d, J=3.4 Hz); 3.99 (2H, s); 3.69 (3H, s); 2.46 (3H, s); 2.45 (3H, s); 2.19 (3H, s); 1.20 (9H, s), APCI-MS m/z 446.3 (M+H)$^+$.

Example J8

5-(2,3,5-trimethoxybenzyl)-N'-(1,3,4-trimethyl-1H-pyrazolo[3,4-b]pyridin-6-yl)-2-furohydrazide Compound J8

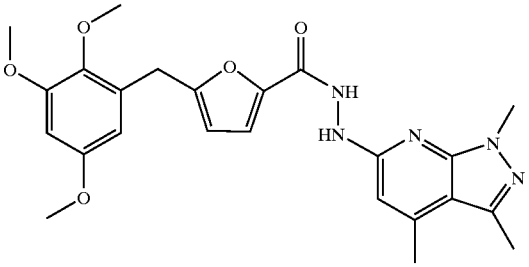

Compound J8 was synthesized according to scheme J. $^1$H NMR (300 MHz, CDCl$_3$): δ 2.51 (s, 3H), 2.54 (s, 3H), 3.73 (s, 3H), 3.74 (s, 3H), 3.84 (s, 3H), 3.93 (s, 3H), 4.01 (s, 2H), 6.14 (d, 1H, J=3 Hz), 6.29 (d, 1H, J=3 Hz), 6.33(s, 1H), 6.41 (d, 1H, J=3 Hz), 7.11 (d, 1H, J=3 Hz), APCI-MS m/z 466 (M+H)$^+$.

Example J9

5-(2,3,6-trimethoxybenzyl)-N'-(1,3,4-trimethyl-1H-pyrazolo[3,4-beta]pyridin-6-yl)-2-furohydrazide Compound J9

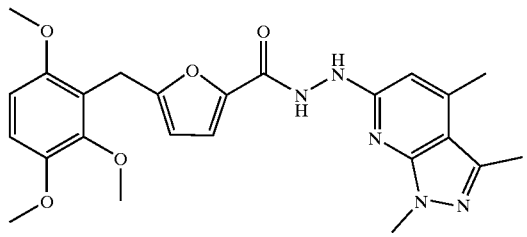

Compound J9 was synthesized according to scheme J. $^1$H NMR (300 MHz, CDCl$_3$): δ 2.44 (s, 3H), 2.48 (s, 3H), 3.71 (s, 3H), 3.75 (s, 3H), 3.76 (s, 3H), 3.84 (s, 3H), 4.02 (s, 2H), 5.96 (d, 1H, J=3 Hz), 6.23 (s, 1H), 6.52 (d, 1H, J=9 Hz), 6.73 (d, 1H, J=9 Hz), 7.01 (d, 1H, J=3 Hz), 8.49 (s, 1H), APCI-MS m/z 466 (M+H)$^+$.

Example J10

5-(2,4,6-trimethoxybenzyl)-N-(1,3,4-trimethyl-1H-pyrazolo[3,4-b]pyridin-6-yl)-2-furohydrazide Compound J10

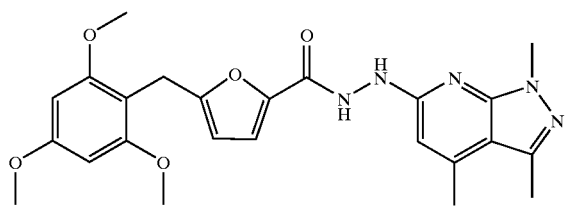

Compound J10 was synthesized according to scheme J. $^1$H NMR (300 MHz, CDCl$_3$): δ 2.24 (s, 3H), 2.39 (s, 3H), 3.66–3.73 (m, 12H), 3.84 (s, 3H), 5.78 (d, 1H, J=6 Hz), 6.02–6.06 (m, 3H), 6.93 (d, 1H, J=3 Hz), 7.52 (s, 1H), 8.54 (s, 1H), APCI-MS m/z 466 (M+H)$^+$.

Exmaple J11

5-(4-Hydroxy-2,5-dimethoxybenzyl)-N-(1,3,4-trimethyl-1H-pyrazolo(3,4-b)pyridin-6-yl)-2-furohydrozide Compound J11

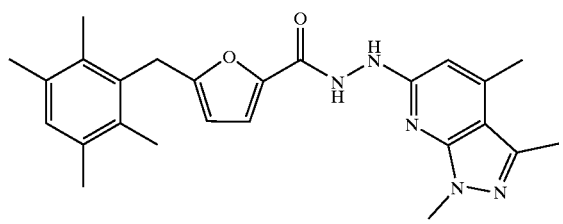

Compound J11 was synthesized according to scheme J. $^1$H NMR (300 MHz, CDCl$_3$): δ 2.26 (s, 3H), 2.33 (s, 3H), 3.53 (s, 3H), 3.58 (s, 3H), 3.63 (s, 3H), 3.73 (s, 2H), 5.85 (d, 1H, J=3 Hz), 6.04 (s, 1H), 6.36 (s, 1H), 6.46 (d, 1H), 6.89 (d, 1H, J=3 Hz), 7.18 (s, 1H), 8.40 (s, 1H), APCI-MS m/z 452 (M+H)$^+$.

Example J12

5-(2,3,5,6-Tetramethylbenzyl)-N'-(1,3,4-trimethyl-1H-pyrazolo[3,4-b]pyridin-6-yl)-2-furohydrazide Compound J12

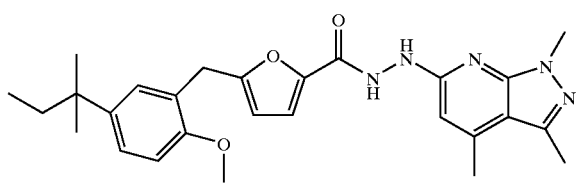

Compound J12 was synthesized according to scheme J. $^1$H NMR (300 MHz, MeOD): δ 2.19–2.23 (m, 12H), 2.54 (s, 3H), 2.56 (s, 3H), 3.79 (s, 3H), 5.80 (d, 1H, J=3 Hz), 6.34 (s, 1H), 6.91 (s, 1H), 7.08 (d, 1H, J=3 Hz), APCI-MS m/z 432 (M+H)$^+$.

Example J13

5-[2-Methoxy-5-(tert-pentyl)benzyl]-N'-(1,3,4-trimethyl-1H-pyrazolo[3,4-b]pyridin-6-yl)-2-furohydrazide Compound J13

Compound J13 was synthesized according to scheme J. $^1$H NMR (300 MHz, CDCl$_3$): δ 2.06 (t, 3H, J=6 Hz), 1.24 (s, 6H), 1.59 (q, 2H), 2.54 (s, 3H), 2.55 (s, 3H), 3.80 (s, 3H), 3.98 (s, 3H), 4.10 (s, 2H), 6.03 (d, 1H, J=6 Hz), 6.37 (s, 1H), 6.81 (d, 1H, J=9 Hz), 7.11–7.20 (m, 3H), 8.57(Brs, 1H), 10.14 (Br s, 1H), APCI-MS m/z 476 (M+H)⁺.

Example J14

5-(2,4,5-trimethoxybenzyl)-N-(1,3,4-trimethyl-1H-pyrazolo[3,4-b] pyridin-6-yl)-2-furohydrazide Compound J14

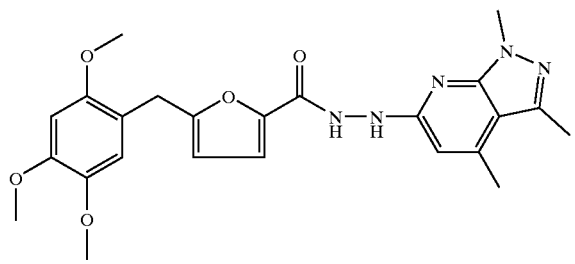

Compound J14 was synthesized according to scheme J.
$^1$H NMR (300 MHz, CDCl$_3$): δ 2.55 (s, 3H), 2.58 (s, 3H), 3.83–3.91 (m, 9H), 3.99 (s, 2H), 6.10 (br s, 1H), 6.32 (s, 1H), 6.73 (s, 1H), 7.13 (d, 1H, J=3 Hz), 7.54 (s, 1H), 8.48 (s, 1H), APCI-MS m/z 466 (M+H)⁺.

Example J15

5-[(1,1,3,3,6-pentamethyl-2,3-dihydro-1H-inden-5-yl)methyl]-N-(1,3,4-trimethyl-1H-pyrazdo[3,4-b]Pyridin-6-yl)-2-furohydrazide Compound J16

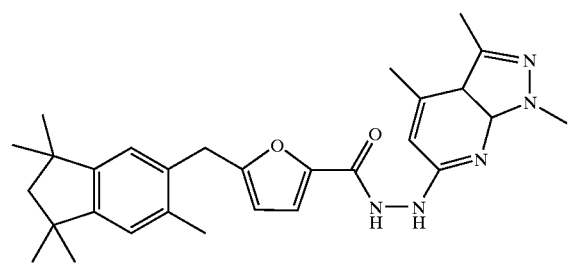

Compound J15 was synthesized according to scheme J.
$^1$H NMR (300 MHz, CDCl$_3$): δ 1.27(6H, s), 1.29 (6H, s), 1.90 (2H, s), 2.32 (3H, s), 2.54 (3H, s), 2.57 (3H, s), 3.88 (3H, s), 4.01 (2H,s) 6.06–6.10 (1H, d, J=3.40 Hz), 6.29 (1H, s), 6.88 (1H, s), 6.94 (1H, s), 7.11–7.14 (1H, d, J=3.40 Hz), APCI-MS m/z 486 (M+H)⁺

Example J16

5-(5-cyclohexyl-2-methylbenzyl)-N'-(1,3,4-trimethyl-1H-pyrazolo[3,4-b]pyridin-6-yl)-2-furohydrazide Compound J16

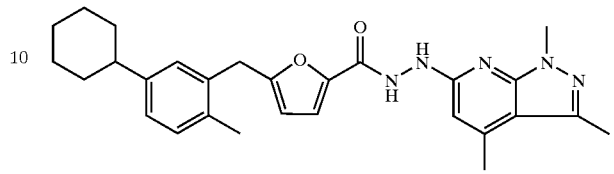

Compound J16 was synthesized according to scheme J.
$^1$H NMR (300 MHz, CDCl$_3$): δ 0.98–1.2 (m, 7H), 1.49–1.61 (m, 3H), 2.03 (s, 3H), 2.24 (m, 1H), 2.35 (s, 3H), 2.37 (s, 3H), 3.77 (s, 2H), 3.82 (s, 3H), 5.82 (d, 1H), 6.21 (s, 1H), 6.75 (s, 1H), 6.79–6.85 (m, 1H), 6.87–6.92 (m, 1H), 6.96 (d, 1H), APCI-MS m/z 472.1 (M+H)⁺.

Example J17

5-(2,5-Dimethylbenzyl)-N'-(1,3,5-trimethyl-1H-pyrazolo[3,4-b]pyridin-6-yl)-2-furohydrazide Compound J17

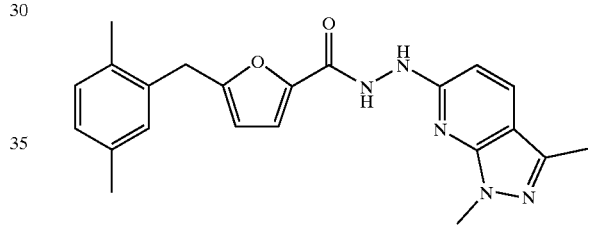

Compound J17 was synthesized according to scheme J.
$^1$H NMR (300 MHz, CH$_3$OD): δ 2.01–2.04 (m, 6H), 2.33–2.34 (m, 6H), 3.57 (s, 3H), 3.82 (s, 3H), 5.85 (d, 1H, J=3 Hz), 6.14 (s, 1H), 6.74–6.88 (m, 3H), 6.92 (d, 1H, J=3 Hz), APCI-MS m/z 404 (M+H)⁺.

Example J18

5-[(4,6-dimethyl[1,1'-biphenyl]-3-yl)methyl]-N'-(1,3,4-trimethyl-1H-pyrazolo[3,4-b]pyridin-6-yl)-2-furohydrazide Compound J18

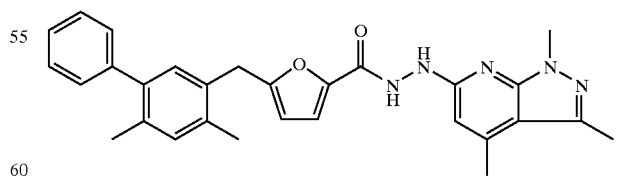

Compound J18 was synthesized according to scheme J.
$^1$H NMR (300 MHz, CH$_3$OD): δ 1.98 (s, 3H), 2.10 (s, 3H), 2.33 (s, 6H), 3.54 (s, 3H), 3.86 (s, 2H), 5.93 (d, 1H, J=3 Hz), 6.14 (s, 1H), 6.81 (s, 1H), 6.88 (s, 1H), 6.92 (d, 1H, J=3 Hz), 7.04–7.16 (m, 5H), APCI-MS m/z 480.3 (M+H)⁺.

Example J19

5-[5-(tert-butyl)-2-methoxybenzyl]-N'-(1,3,4-trimethyl-1H-pyrazolo[3,4-b]pyridin-6-yl)-2-furohydrazide Compound J19

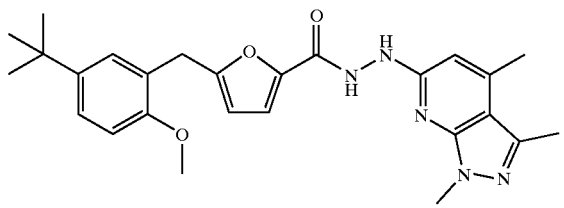

Compound J19 was synthesized according to scheme J. $^1$H NMR (300 MHz, CDCl$_3$): δ 1.31 (s, 9H), 2.59 (s, 6H), 3.83 (s, 3H), 4.03 (s, 3H), 4.04 (s, 2H), 6.11 (d, 1H, J=3 Hz), 6.42 (s, 1H), 6.84 (d, 1H, J=9 Hz), 7.17–7.21 (m, 2H), 7.31 (s, 1H), 8.47(Brs, 1H), 10.50 (Br s, 1H), APCI-MS m/z 462(M+H)$^+$.

Example J20

N,N-diethyl-1-{4-methyl-3-[(5-{[2-(1,3,4-trimethyl-1H-pyrazolo[3,4-b]pyridin-6-yl)hydrazino]carbonyl}-2-furyl)methyl]phenyl}cyclopropanecarboxamide Compound J20

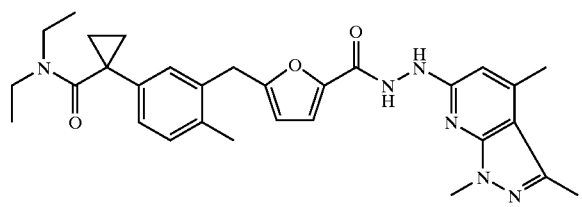

Compound J20 was synthesized according to scheme J. $^1$H NMR (300 MHz, CDCl$_3$): δ 0.76 (t, 3H), 1.04–1.13 (m, 5H), 1.36 (t, 2H), 2.28 (s, 3H), 2.55 (s, 3H), 2.56 (s, 3H), 3.32 (q, 4H), 3.91 (s, 3H), 3.98 (s, 2H), 5.99 (d,1H), 6.33 (s, 1H), 6.97 (d, 1H), 7.07–7.15 (m, 3H), APCI-MS m/z 529.2 (M+H)$^+$.

Example J21

5-(4-Hydroxy-2-methylbenzyl)-N'-(1,3,4-trimethyl-1H-pyrazolo[3,4-b]pyridin-6-yl)-2-furohydrazide Compound J21

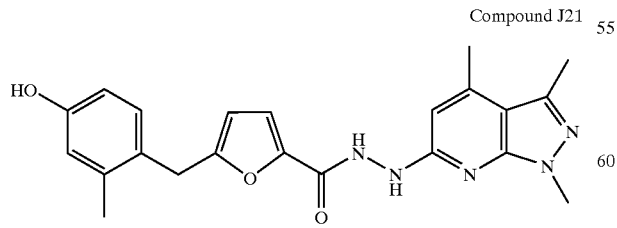

Compound J21 was synthesized according to scheme J. $^1$H NMR (DMSO-d$_6$): δ 2.18, 2.44, 2.47, 3.69 (4s, 3H each), 3.89 (s, 2H), 6.12 (d, 1H, J=3.02 Hz), 6.45–6.6 (m, 2H), 6.95 (d, 1H, J=8.3 Hz), 7.16 (d, 1H, J=3.02 Hz), 8.7 (s, 1H), 9.18 (s, 1H), 10.19 (s, 1H), APCI-MS m/z 406.1 (M+H)$^+$.

Example J22

5-[(4,4,7-trimethyl-3,4-dihydro-2H-chromen-6-yl)methyl]-N'-(1,3,4-trimethyl-1H-pyrazolo[3,4-b]pyridin-5-yl)-2-furohydrazide Compound J22

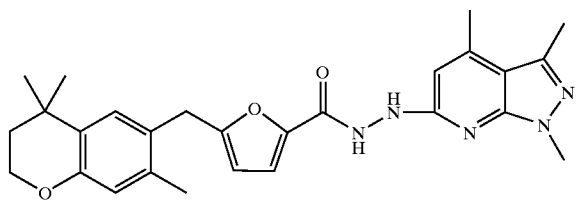

Compound J22 was synthesized according to scheme J. $^1$H NMR (300 MHz, CDCl$_3$): δ 1.33 (s, 6H), 1.84 (t, 2H, J=5.28 Hz), 2.22, 2.59, 2.60 (3s, 3H each), 3.95 (s, 2H), 4.03 (s, 3H), 4.19 (t, 1H, J=5.29 Hz), 4.47 (br s, H$_2$O), 6.01 (d, 1H, J=3.40 Hz), 6.42 (s, 1H), 6.65 (s, 1H), 7.06 (s, 1H), 7.14 (d, 1H, J=3.40 Hz), 8.65 (br s, 1H), 10.45 (br s, 1H), APCI-MS m/z 474.2 (M+H)$^+$.

Example J23

6-[(3,5,5,8,8-Pentamethyl-5,6,7,8-tetrahydro-2-naphthalenyl)oxy]-N'-(1,3,4-trimethyl-1H-pyrazolo[3,4-b]pyridin-6-yl)-2-pyridinecarbohydrazide Compound J23

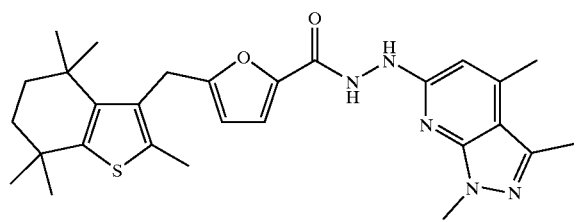

Compound J23 was synthesized according to scheme J. $^1$H NMR (300 MHz, DMSO-d$_6$): δ 1.20,1.28 (s, 6H each), 1.66 (s, 4H ), 2.28 (s, 3H), 2.50 (s, 3H), 2.53 (s, 3H), 3.75 (s, 3H), 4.06 (s, 2H), 6.01 (d, 1H), 6.27 (s, 1H), 7.21 (d, 1H), 8.73 (s, 1H), 10.22 (br, 1H), APCI-MS m/z 506.3 (M+H)$^+$.

Example J24

5-(3-chloro-5-isopropyl-6-methoxy-2-methylbenzyl)-N'-(1,3,4-trimethyl-1H-pyrazolo[3,4-b]pyridin-6-yl)-2-furohydrazide Compound J24

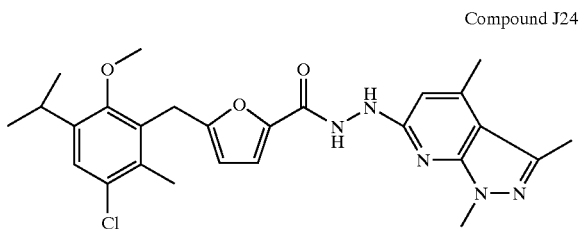

Compound J24 was synthesized according to scheme J. $^1$H NMR (300 MHz, CDCl$_3$): δ 1.21 (s, 3H), 1.23 (s, 3H), 2.29 (s, 3H), 2.56 (s, 3H), 2.58 (s, 3H), 3.26 (m, 1H), 3.66 (s, 3H), 4.01 (s, 3H), 4.13 (s, 2H), 5.93 (d, 1H), 6.40 (s, 1H), 7.11 (d, 1H), 7.23 (s, 1H), 8.66 (br, 1H), APCI-MS m/z 496.3 (M+H)$^+$.

Compound J25: 5-{[(2,6-dimethylphenyl)sulfanyl]methyl}-N'-(1,3,4-trimethyl-1H-pyrazolo[3,4-b]pyridin-6-yl)-2-furohydrazide Compound J25

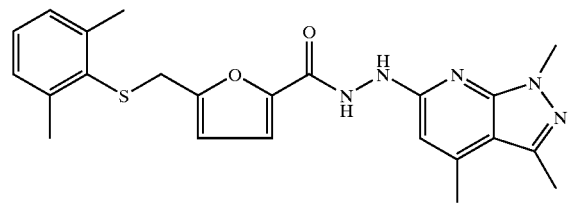

Compound J25 was synthesized according to scheme J. $^1$H NMR (300 MHz, CDCl$_3$): δ 2.45 (s, 6H), 2.56 (s, 3H), 2.60 (s, 3H), 3.82 (s, 2H), 3.90 (s, 3H), 5.98 (d, 1H), 6.28 (s, 1H), 6.88 (br s, 1H), 7.08 (d, 1H), 7.15 (m, 3H), 8.15 (br s, 1H), APCI-MS m/z 436.2 (M+H)$^+$.

Example J26

5-(3,8,8-Trimethyl-5,6,7,8-tetrahydro-naphthalen-2-ylmethyl)-furan-2-carboxylic acid N'-(1,3,4-trimethyl-1H-pyrazolo[3,4-b]pyridin-6-yl)-hydrazide Compound J26

Compound J26 was synthesized according to scheme J. $^1$H (300 MHz, MeOH-d$_4$): δ 1.23 (2s, 3H each), 1.40–1.60 (m, 2H), 1.50–1.70 (m, 2H), 2.21 (s, 3H), 2.55 (s, 6H), 2.70 (t, 2 H, J=6.04 Hz), 3.79 (s, 3H), 4.02 (s, 2H), 6.05 (d,1H, J=3.59 Hz), 6.36, 6.83 (2s, 1H each), 7.14 (br s, 2H). MS m/z 472.3 (M+H)$^+$

Example J27

5-(2-phenylethynyl)-N'-(1,3,4-trimethyl-1H-pyrazolo[3,4-b]pyridin-6-yl)-2-furohydrazide Compound J27

Compound J27 was synthesized according to scheme J. $^1$H NMR (300 MHz, CD$_3$OD): δ 3.36 (2s, 6H each, superimposed with methanol), 3.84 (s, 3H), 6.46 (s, 1H), 6.92 (d, 1H, J=3.4 Hz), 7.29 (d, 1H, J=3.78 Hz), 7.35–7.45 (m, 4H), 7.50–7.60 (m, 2H), APCI-MS m/z 386.2 (M+H)$^+$, HRMS M/Z expected 386.1617. found 386.1607

Example J28

5-(2,4,4,7,7-Pentamethyl-4,5,6,7-tetrahydro-benzo[b]thiophen-3-ylmethyl)-furan-2-carboxylic acid N'-(1,3,4-trimethyl-1H-pyrazolo[3,4-b]pyridin-6-yl)-hydrazide Compound J28

Compound J28 was synthesized according to Scheme J, wherein compound 66 was synthesized as shown below:

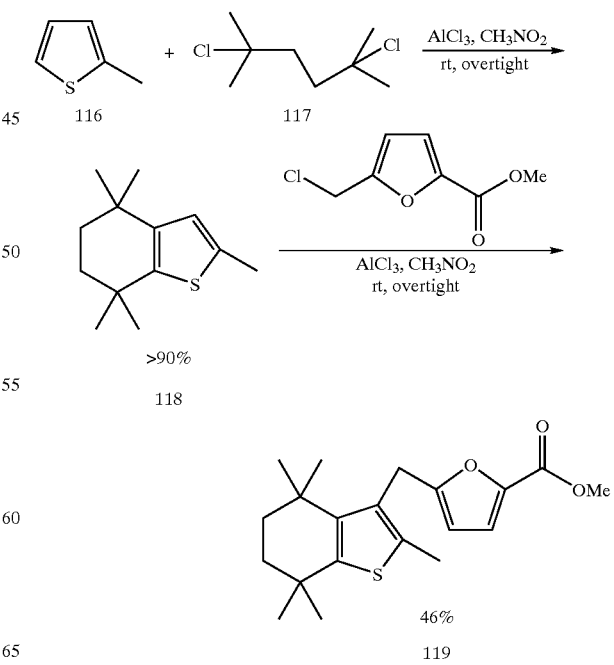

To a solution of 116 (3.0 g) and 117 (5.6 g) in CH₃NO₂ (150 ml) was added AlCl₃ (4.1 g). The solution was stirred at rt. overnight, poured into ice water, extracted with EtOAc, dried (MgSO₄) and concentrated to give compound 118 (7.3-g crude). AlCl₃ (2.9 g, 1.5 eq.) was added to the crude mixture (3 g) in CH₃NO₂ (120 ml) at RT. The solution was stirred overnight. Compound 119 (2.3 g) was isolated by column chromatography. ¹H NMR (DMSO-d6): δ 1.20 (s, 6H), 1.28 (s, 6H), 1.65 (s, 4H), 2.28 (s, 3H), 2.50 (s, 3H), 2.53 (s, 3H), 3.75 (s, 3H), 4.06 (s, 2H), 6.01 (d, 1H), 6.27 (s, 1H), 7.22 (d, 1H), 8.73 (s, 1H), 8.73 (s, 1H), 10.22 (s, 1H). APCI-MS m/z 506.3 (M+H)⁺.

Example J29

3-(2,3,4,6-Tetramethyl-5-{5-[N'-(1,3,4-trimethyl-1H-pyrazolo[3,4-b]pyridin-6-yl)-hydrazinocarbonyl]-furan-2-ylmethyl}-benzyl)-furan-1-carboxylic acid N'-(1,3,4-trimethyl-1H-pyrazolo[3,4-b]pyridin-6-yl)-hydrazide

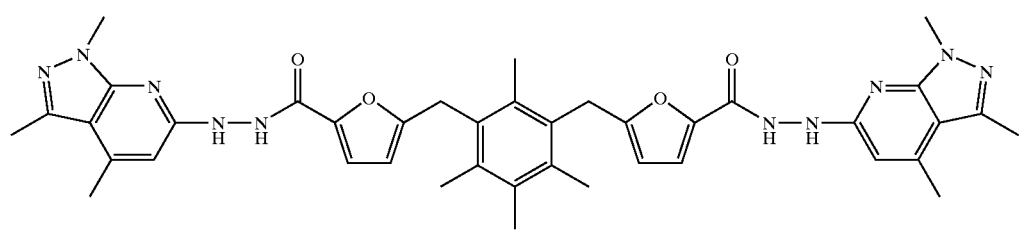

Compound J29

Compound J29 was synthesized in a manner analogous to Scheme J, starting with 196.7 mg of carboxylic acid analog to give 9.0 mg of product (2.4%). ¹H NMR: δ (300 MHz, CDCl₃) 2.29 (t, 12H), 2.53 (s, 6H), 2.56 (s, 6H), 3.87 (s, 6H), 4.13 (s, 4H), 5.89 (d, 2H), 6.28 (s, 2H), 7.05 (d, 2H), 7.08 (bs, 2H).

Example J30

5-(3,5-Dichloro-2-methoxy-4,6-dimethyl-benzyl)-furan-2-carboxylic acid N'-(1,3,4-trimethyl-1H-pyrazolo[3,4-b]pyridin-6-yl)-hydrazide Compound J30

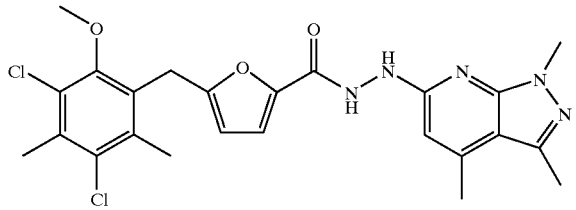

Compound J30 was synthesized according to Scheme J, where compound 67 was synthesized according to the following scheme and the procedure for the coupling involved the use of HATU.

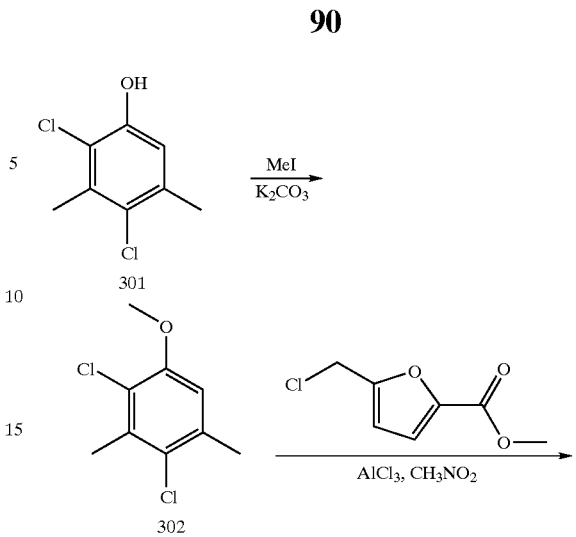

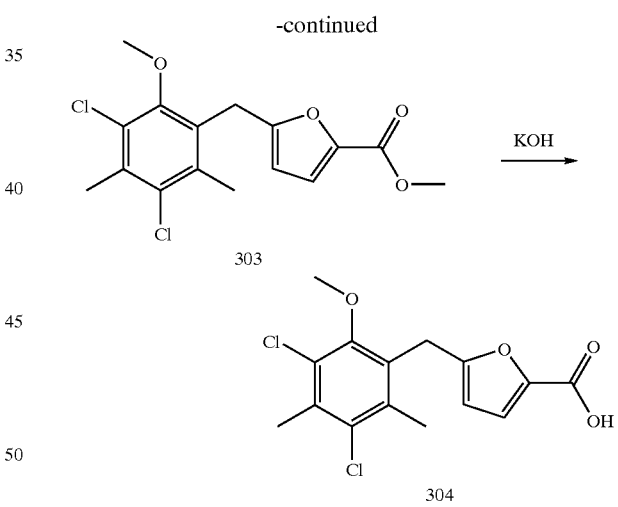

To a solution of 301 (5 g, 26.2 mmol) in 50 mL DMSO was added K₂CO₃ (5 g, 36.2 mmol) followed by MeI (4.5 g, 31.4 mmol). The mixture was stirred at room temperature over night diluted with 100 mL water, extracted with Et₂O, dried with MgSO₄, concentrated to give 5.4 g (95%) white solid.

To a solution of 302 (5 g, 24.4 mmol) and methyl 5-chloromethylfurate (4.2 g, 24 mmol) in 100 mL CH₃NO₂ was added AlCl₃ (3.5 g, 26.3 mmol), the mixture was stirred at room temperature overnight, diluted with 100 mL cooled water, extracted with Et₂O and then concentrated. The recidues was dissolved in 50 mL MeOH, 15 mL 2N KOH was added. The mixture was stirred at rt. for 2 hr. unreacted starting material was extracted by diethyl ether. The aqueous layer was acidified by 2N HCl aqueous solution. Extracted with diethyl ether, dried over MgSO₄ and concentrated to give 4.7 g product (overall yield 60%). ¹HNMR (DMSO-d₆): δ 2.39(s, 3H), 2.50–2.59(m, 9H), 3.78–3.84(d, 6H), 4.26(s, 2H), 6.05 (d, 1H), 6.36(s, 1H), 7.14(d, 1H). LC-MS (APCI, pos.): 502(M+1).

To a solution of compound 102 (0.68 g, 2.41 mmol) in benzene (10 mL) was added aniline (0.33 mL, 3.7 mmol) and AcOH (0.1 mL). The reaction mixture was heated at 135° C. for 7 hours, water was collected in Dean Stark tube. The solvent was removed. Column chromatography afford Compound 103 as a yellow oil (596 mg, 69%). The solution of Compound 103 (596 mg, 1.67 mmol) in diphenyl ether (2

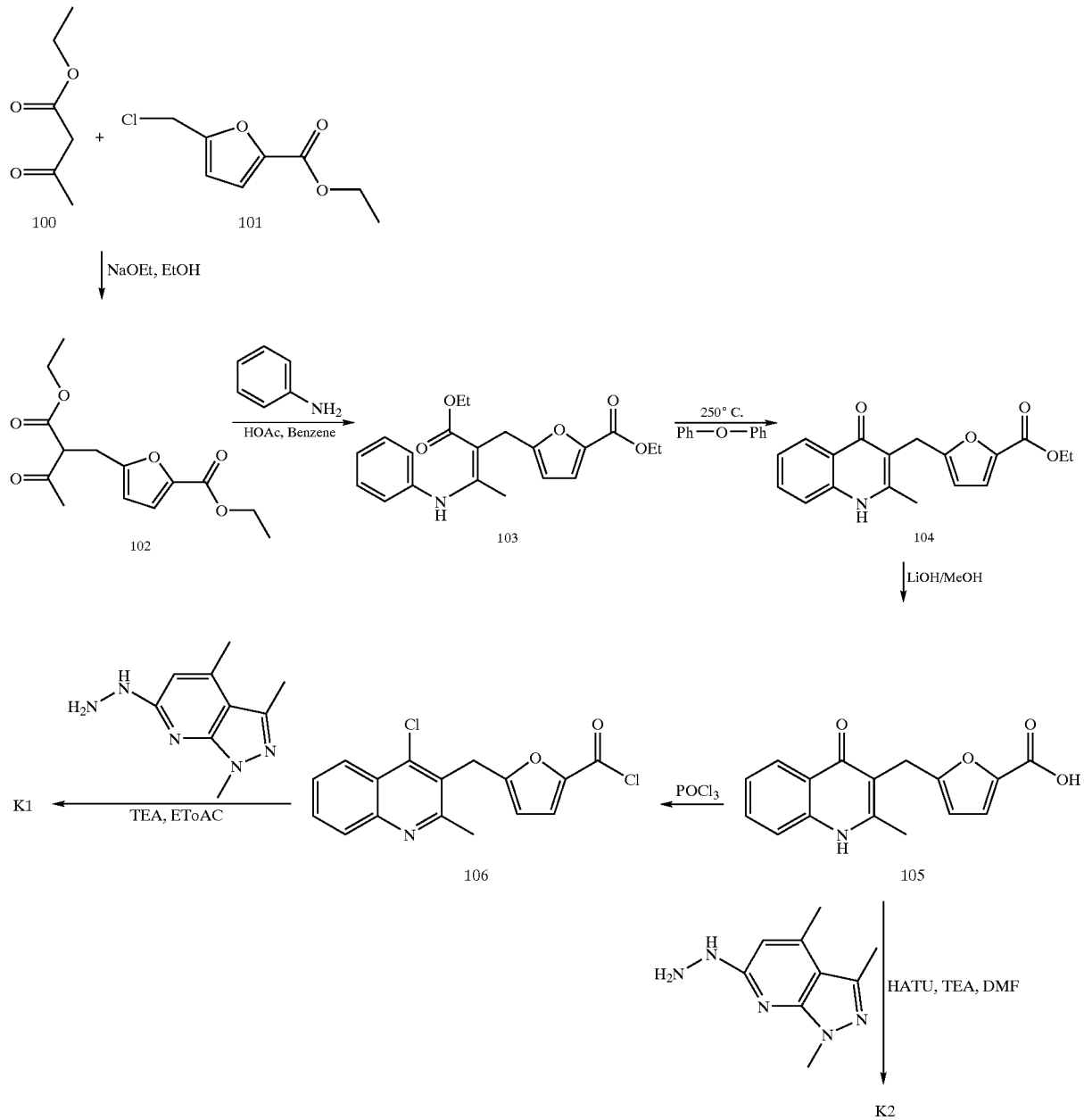

To NaOEt (1.12 mL, 9 mmol, 21% wt in EtOH solution), compound 100 (1 mL, 9 mmol) in EtOH (10 mL) was added drop wise. After stirring for 10 minutes, compound 101 (0.46 mL, 3 mmol) in EtOH (5 mL) was added within 20 minutes. The reaction was stirred overnightn and then evaporated. The crude product was dissolved in EtOAc, washed with NaHSO₄ and brine, dried over NaSO₄ and evaporated to dryness. Column chromatography with DCM afforded compound 102 as a clear oil (450 mg, 53%).

mL) was heated in a silicon oil bath at 250° C. for 15 min. The reaction was cooled and hexanes (100 mL) were added. The solid generated was collected by filtration and compound 104 was obtained as a brown solid (440 mg, 85%).

To the solution of compound 104 (42 mg, 0.135 mmol) in MeOH (2 mL) was added LiOH (2 mL, 2 M). The solution was stirred at room temperature for 1.5 h, quenched with 5% NaHSO₄ and compound 105 precipitated out (32 mg, 84%). OCl₃ (2.5 mL) was added to Compound 105 (132 mg, 0.466 mmol) and reflux for 2 h and then poured onto ice. 1N NaOH (250 mL) was added. It was extracted with EtOAc. EtOAc phase was dried over $Na_2SO_4$ and taken to dryness to give Compound 106. To the solution of Compound 105 (42.1 mg, 0.139 mmol) in EtOAc (1 mL) was added 6-hydrazino-1,3,4-trimethyl-1H-pyrazolo[3,4-b]pyridine (26.7 mg, 0.139 mmol) and TEA (21 μl, 0.153 mmol). The solution was stirred overnight. HPLC purification afforded K1 as a yellow solid (19 mg, 30%). To the solution of Compound 106 (48 mg, 0.169 mmol) in DMF (2 mL) was added 6-hydrazino-1,3,4-trimethyl-1H-pyrazolo[3,4-b]pyridine (49 mg, 0.254 mmol), HATU (97 mg, 0.253 mmol) and TEA (47 ul, 0.339 mmol). The solution was stirred overnight. HPLC purification afforded K2 as a yellow solid (60.1 mg, 78%).

Example K1

5-(4-Chloro-2-methyl-quinolin-3-ylmethyl)-furan-2-carboxylic acid N'-(1,3,4-trimethyl-1H-pyrazolo[3,4-b]pyridin-6-yl)-hydrazide ($^1$H NMR 300 Hz, $CDCl_3$): δ 2.29 (s, 3H), 2.35 (s, 3H), 2.62 (s, 3H), 3.62 (s, 3H), 4.26 (s, 2H), 5.91 (d, 1H, J=3 Hz), 6.04 (s, 1H), 6.90 (d, 1H, J=3 Hz), 7.20 (br s, 1H), 7.42 (d, 1H, J=6 Hz), 7.5.3 (d, 1H, J=6 Hz), 7.81 (d, 1H, J=9 Hz), 7.99 (d, 1H, J=6 Hz) APCI-MS m/z 475 $(M+H)^+$.

Example K2

5-(4-Hydroxy-2-methyl-quinolin-3-ylmethyl)-furan-2-carboxylic acid N'-(1,3,4-trimethyl-1H-pyrazolo[3,4-b]pyridin-6-yl)-hydrazide ($^1$H NMR 300 Hz, MeOH-$d_4$) δ 2.54(s, 6H), 2.61 (s, 3H), 3.73 (s, 3H), 4.19 (s, 2H), 6.25 (d, 1H, J=3 Hz), 6.34 (s, 1H), 7.11 (d, 1H, J=3 Hz), 7.46 (m, 1H), 7.67 (s, 1H), 7.71 (s, 1H) APCI-MS m/z 457 $(M+H)^+$.

Example L1

5-(7-Chloro-4,4-dimethyl-2-oxo-1,2,3,4-tetrahydro-quinolin-6-yloxy)-furan-2-carboxylic acid N'-(1,4-dimethyl-1H-pyrazolo[3,4-b]pyridin-6-yl)-hydrazide

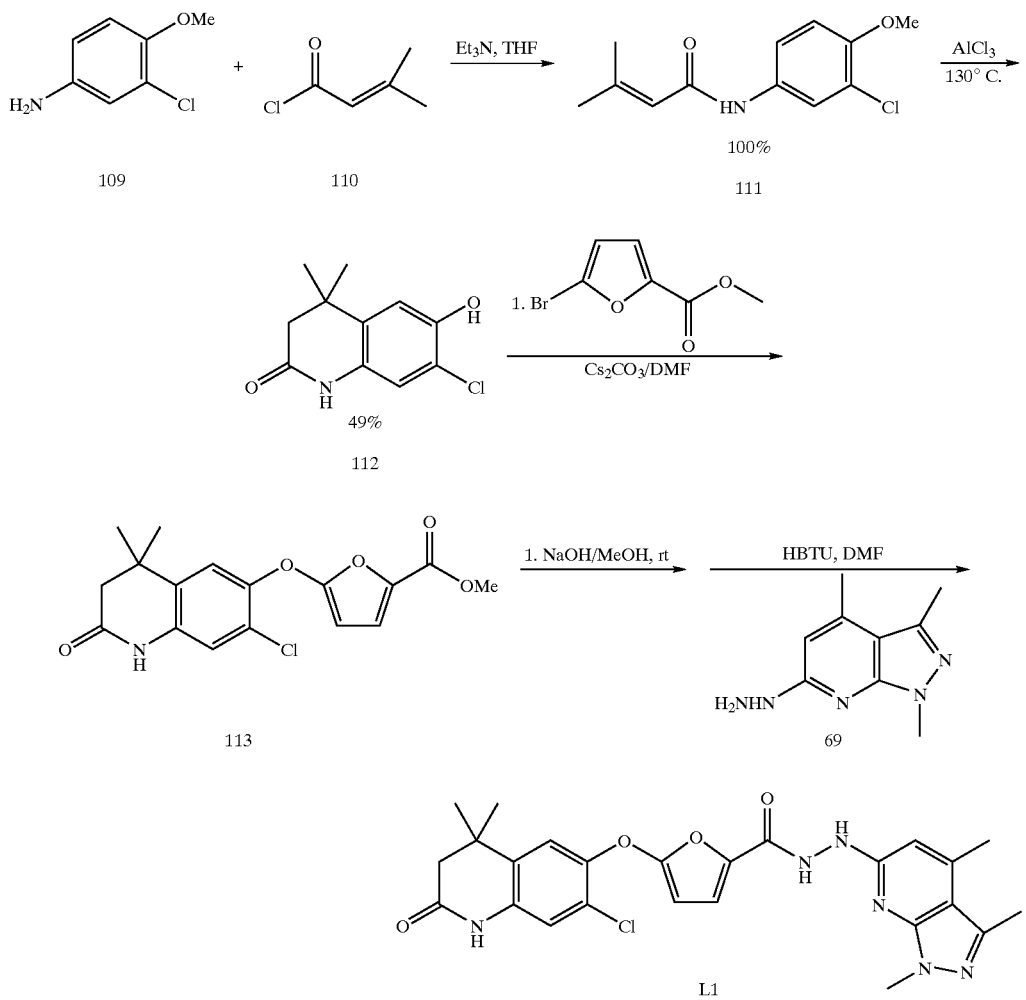

To a solution of Compound 109 (10 g) and 110 (7.5 g) in THF (200 ml) was added $EtN_3$ (6.5 g). The solution was stirred at room temperature overnight. The reaction mixture was extracted with EtOAc, dried and concentrated to give 16 g of 111 as brown oil. The residue was dissolved in 100 ml of $CH_2Cl_2$. To this solution was added $AlCl_3$ (33 g). The solution was concentrated. The mixture was heated to 130° C. in an oil bath under $N_2$ overnight. The mixture was cooled to room temperature and extracted with EtOAc. Compound 112 was precipitated in $CH_3CN$ (7.3 g). $^1H$ NMR (DMSO-$d_6$): δ 1.21 (s, 6H), 2.38 (s, 2H), 2.45 (s, 3H), 2.49 (s, 3H), 3.71 (s, 3H), 5.58 (d,1H), 6.22 (s, 1H), 7.05 (s, 1H), 7.25 (d,1H), 7.35 (s, 1H), 8.68 (s, 1H), 10.22 (s, 1H), 10.32 (s, 1H). APCI-MS m/z 509.3 $(M+H)^+$.

Example L2

5-(7-Chloro-1,4,4-trimethyl-2-oxo-1,2,3,4-tetrahydro-quinolin-6-yloxy)-furan-2-carboxylic acid N'-(1,3,4-trimethyl-1H-pyrazolo[3,4-b]pyridin-6-yl)-hydrazide Compound L2

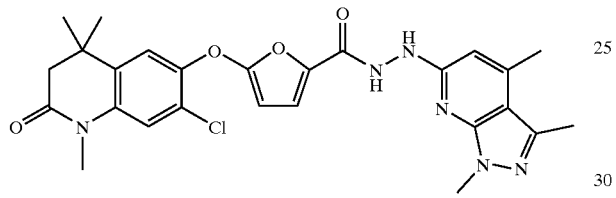

Compound L2 was synthesized in a similar manner as Example L1 wherein compound 113 was alklyated to give compound 114 as shown below:

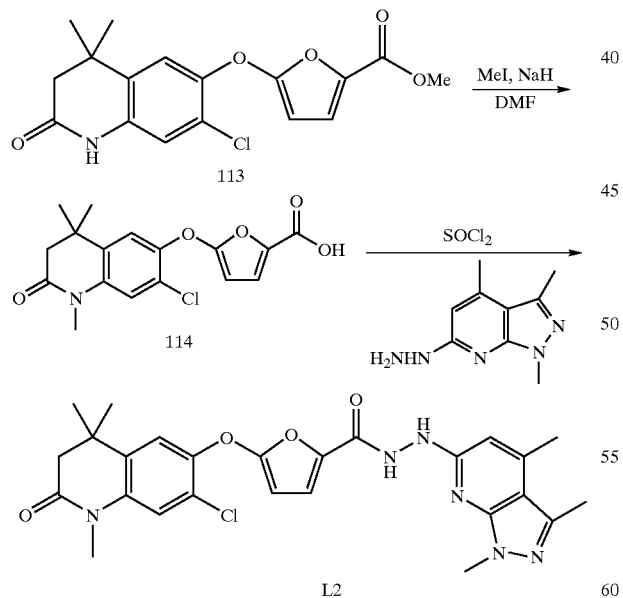

$^1H$ NMR (DMSO-$d_6$): δ 1.21 (s, 6H), 2.47 (s, 2H), 3.31(s, 3H), 3.38 (s, 3H), 3.72 (s, 3H), 5.65 (d, 1H), 6.23 (s, 1H), 7.28 (d, 1H), 7.37 (s, 2H), 8.70 (s, 1H). APCI-MS m/z 523.4 $(M+H)^+$.

Scheme M

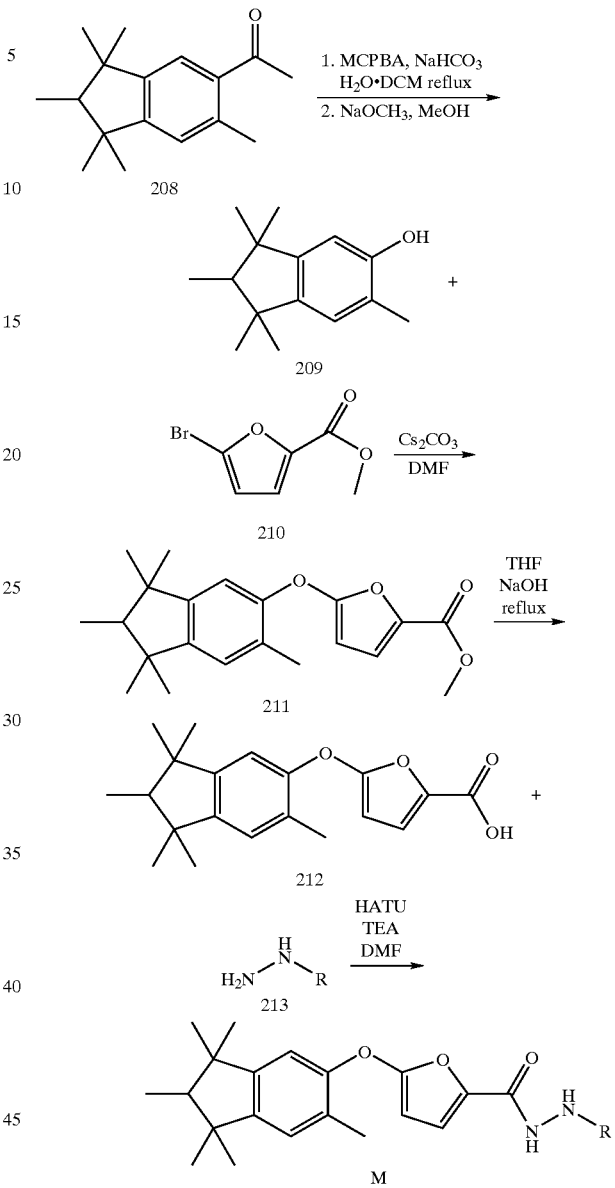

The keto-indane, compound 208, is dissolved in DCM:water, 1:1, and is added sodium bicarbonate. MCPBA is added and reaction mixture is allowed to reflux overnight, quenched with NaOH, extracted with DCM, and concentrated. The mixture is disolved in methanol and sodium methoxide is added until color changed. Acidified to acitic pH and purified using a plug column. 1 eq of phenol, 1 eq bromide, compound 210, and 2.5 eq $Cs_2CO_3$ is dissolved in DMF(0.5M) and heated to reflux overnight. Solvent is removed and product is purified by column chromatography using 20% ethyl acete in hexanes. The purfied ester is dissolved in THF(0.5M) and $NaOH_{aq}$ 10 eq is added. The mixture is allowed to stir overnight at reflux. THF is removed and aqueous layer is acidified.

Compound 212, is purified by crystallization. 1 eq of the acid, 1.5 eq HATU, and 4.5 eq triethylamine is dissolved in DMF (0.5M) and cooled to 0° C. for 30 min. 1.5 eq of the hydrazine 213 is added to the mixture and the mixture is allowed to gradually warm to room temperature overnight. Final products are purified by prep HPLC.

Example M1

5-(1,1,2,3,3,6-Hexamethyl-indan-5-yloxy)-furan-2-carboxylic acid N'-(chloro-trifluoromethyl-pyridin-2-yl)-hydrazide Compound M1

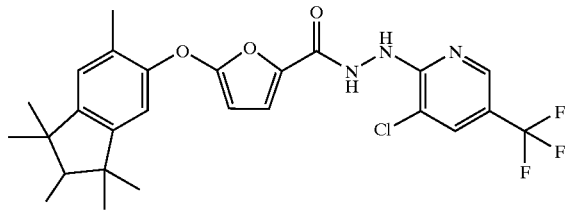

Compound M1 was synthesized according to scheme M. $^1$H NMR (CDCl$_3$): δ 0.98(3H, d, J=7.18 Hz), 1.04(3H, s), 1.07(3H, s), 1.22(3H, s), 1.27(3H, s), 1.87(1H, q, J=7.18 Hz), 2.27(3H, s), 5.33(1H, d, J=3.78 Hz), 6.86(1H, s), 7.01(1H, s), 7.19(1H, d, J=3.78 Hz), 7.79(1H, s), 8.36(1H, s); APCI-MS m/z 521 (M+H)$^+$

Example M2

5-(1,1,2,3,3,6-Hexamethyl-indan-5-yloxy)-furan-2-carboxylic acid N'-(5-trifluoromethyl-pyridin-2-yl)-hydrazide Compound M2

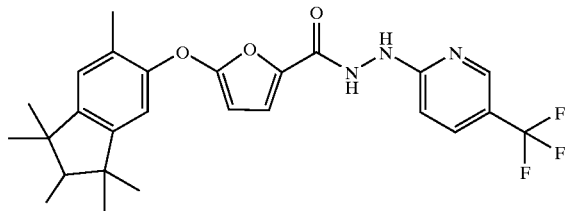

Compound M2 was synthesized according to scheme M. $^1$H NMR (MeOH-d$_4$): δ 0.96(3H, d, J=7.55 Hz), 1.00(3H, s), 1.02(3H, s), 1.18(3H, s), 1.22(3H, s), 1.80(1H, q, J=7.55 Hz), 2.19(3H, s), 5.30(1H, d, J=3.40 Hz), 6.85(2H, m), 7.03(1H, s), 7.15(1H, d, J=3.78 Hz), 7.82(1H, m), 8.27(1H, s); APCI-MS m/z 487 (M+H)$^+$

Compound M3

5-(1,1,2,3,3,6-Hexamethyl-indan-5-yloxy)-furan-2-carboxylic acid N'-quinolin-2-yl-hydrazide Compound M3

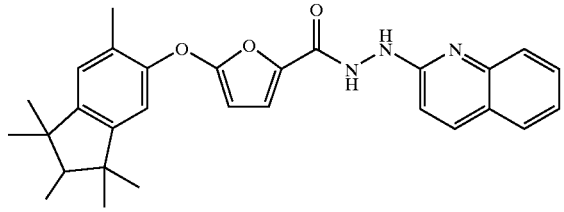

Compound M3 was synthesized according to scheme M. $^1$H NMR (MeOH-d$_4$): δ 0.98(3H, d, J=7.18 Hz), 1.02(3H, s), 1.03(3H, s), 1.20(3H, s), 1.23(3H, s), 1.83(1H, q, J=7.55 Hz), 2.21(3H, s), 5.36(1H, d, J=3.78 Hz), 6.88(1H, s), 7.06(1H, s), 7.18(1H, d, J=9.44 Hz), 7.28(1H, d, J=3.78 Hz), 7.55(1H, m), 7.79(1H, m), 7.88(1H, d, J=8.31 Hz), 7.93(1H, d, J=7.93 Hz), 8.45(1H, d, J=9.44 Hz); APCI-MS m/z 471 (M+H)$^+$

Example M4

5-(1,1,2,3,3,6-Hexamethyl-indan-5-yloxy)-furan-2-carboxylic acid N'-(1,3,4-trimethyl-1H-pyrazolo[3,4-b]pyridin-6-yl)-hydrazide Compound M4

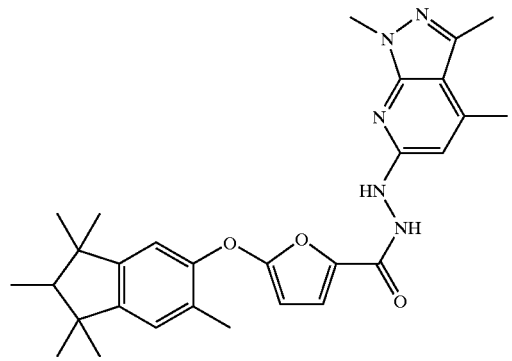

Compound M4 was synthesized according to scheme M. $^1$H NMR (CDCl$_3$): δ 0.98(3H, d, J=7.37 Hz), 1.04(3H, s), 1.07(3H, s), 1.22(3H, s), 1.27(3H, s), 1.87(1H, q, J=7.37 Hz), 2.28(3H, s), 2.54(3H, s), 2.56(3H, s), 3.89(3H, s), 5.36(1H, d, J=3.59 Hz), 6.30(1H, s), 6.85(1H, s), 7.01(1H, s), 7.16(1H, d, J=3.40 Hz); APCI-MS m/z 502 (M+H)$^+$

Scheme N

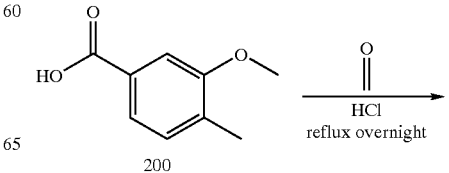

200

-continued

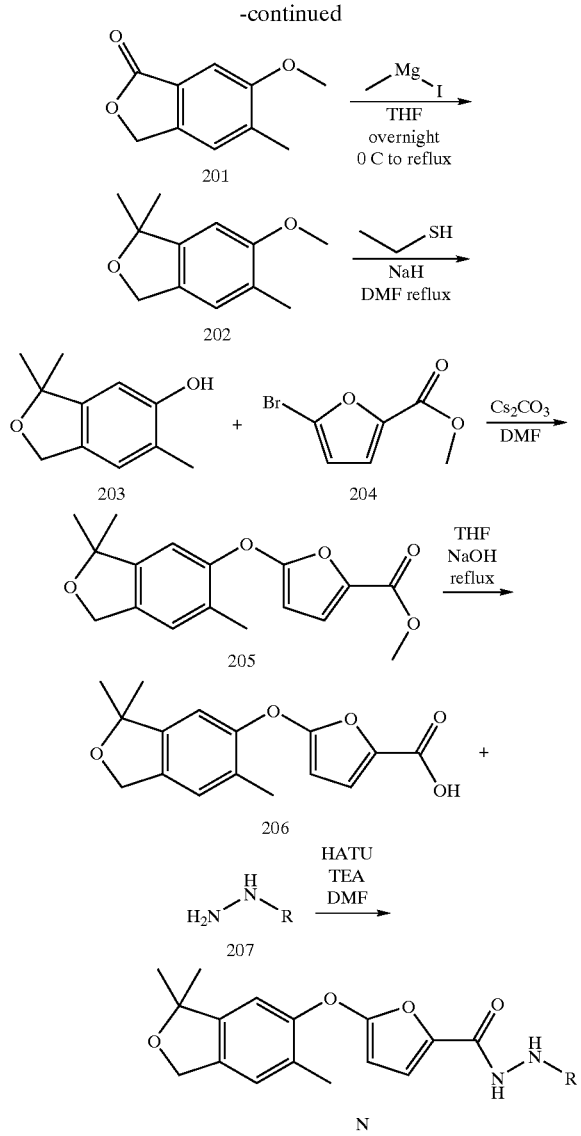

1 eq. of 3-methoxy, 4-methyl, benzoic acid, compound 200, 10 eq. of paraformaldehyde and 15 eq. of HCl are heated to reflux overnight. The solution is cooled to room temperature and filtered. Product is white with melting point of 144–145° C. GCMS shows product at 10.1 min with m/z 178, 149.

This product, compound 201, is taken in THF (0.3M) and cooled to 0° C. 3 eq. of methylmagnesium bromide is added over 30 min and solution is allowed to warm to room temperature over 2 hours. Mixture is then heated to reflux for approximate 1 hour. Reaction mixture is quenched with sat. $NH_4Cl$ (aq) and extracted with ethyl acetate, and concentrated. Added $H_2SO_4$ in MeOH and stirred for 30 min. Solvent is removed and aqueous layer is extracted with ethyl acetate. Product is purified by column with 10% ethyl acetate in hexanes.

The phenol is deprotected by taking 2.5 eq NaH in DMF. 2.5 eq of ethanethiol is added slowly over 2 hours to the mixture. The substrate is added slowly and the reaction mixture is warmed to 65° C. and allowed to stir overnight. The mixture is quenched with 2M HCl and extracted with ethyl acetate. Solvent is removed and product is crystallized from hot hexanes to give phenol, compound 203.

A mixture of 1 eq of phenol, 1 eq bromide, compound 204, and 2.5 eq $Cs_2CO_3$ is dissolved in DMF (0.5M) and heated to reflux overnight. Solvent is removed and product is purified by column chromatography using 20% ethyl acete in hexanes.

The purfied ester is dissolved in THF(0.5M) and $NaOH_{aq}$ 10eq is added. The mixture is allowed to stir overnight at reflux. Solvent is removed and acidified. Compound 206, was purified by crystallization.

A mixture of 1 eq of the acid, 1.5 eq HATU, and 4.5 eq triethylamine is dissolved in DMF(0.5M) and cooled to 0° C. for 30 min. 1.5 eq of the hydrazine compound, 207, is added to the mixture and the reaction is allowed to warm to room temperature overnight. Final products are purified by prep HPLC.

Example N1

5-(3,3,6-Trimethyl-1,3-dihydro-isobenzofuran-5-yloxy)-furan-2-carboxylic acid N'-(chloro-trifluoromethyl-pyridin-2-yl)-hydrazide Compound N1

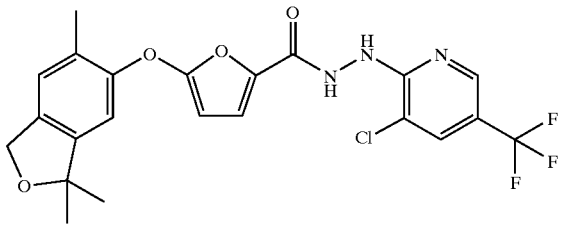

Compound N1 was synthesized according to scheme N. $^1$H NMR (MeOH-d$_4$): δ 1.45(6H, s), 2.29(3H, s), 4.99(2H, s), 5.45(1H, d, J=3.78 Hz), 6.97(1H, m), 7.17(1H, s), 7.20 (1H, d, J=3.78 Hz), 7.93(1H, s), 8.29(1H, s); APCI-MS m/z 483 (M+H)$^+$ Example N2

5-(3,3,6-Trimethyl-1,3-dihydro-isobenzofuran-5-yloxy)-furan-2-carboxylic acid N'-(1,3,4-trimethyl-1H-pyrazolo[3,4-b]pyridin-6-yl)-hydrazide Compound N2

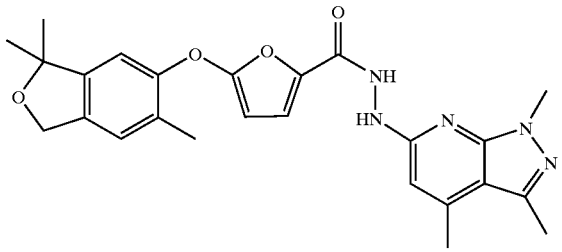

Compound N2 was synthesized according to scheme N. $^1$H NMR (CDCl$_3$): δ 1.45(6H, s), 2.29(3H, s), 2.46(3H, s), 2.54(3H, s), 3.86(3H, s), 5.02(2H, s), 5.36(1H, d, J=3.59 Hz), 6.24(1H, s), 6.81(3H, s), 7.07(1H, s), 7.16(1H, d, J=3.59 Hz); APCI-MS m/z462 (M+H)$^+$

Example N3

5-(3,3,6-Trimethyl-1,3-dihydro-isobenzofuran-5-yloxy)-furan-2-carboxylic acid N'-quinolin-2-yl-hydrazide Compound N3

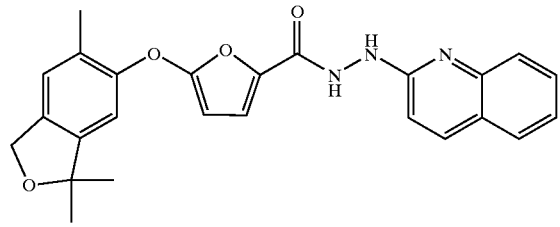

Compound N3 was synthesized according to scheme N. $^1$H NMR (CDCl$_3$): δ 1.46(6H, s), 2.30(3H, s), 5.01(2H, s), 5.50(1H, d, J=3.40 Hz), 7.01(1H, s), 7.21(1H, s), 7.23(1H, d, J=9.44 Hz), 7.34(1H, d, J=3.40 Hz), 7.61(1H, m), 7.84(1H, m), 7.92(1H, d, J=8.69 Hz), 7.97(1H, d, J=7.93 Hz), 8.50(1H, d, J=9.44 Hz); APCI-MS m/z 430 (M+H)$^+$

Example N4

5-(3,3,6-Trimethyl-1,3-dihydro-isobenzofuran-5-yloxy)-furan-2-carboxylic acid N'-(5-trifluoromethyl-pyridin-2-yl)-hydrazide Compound N4

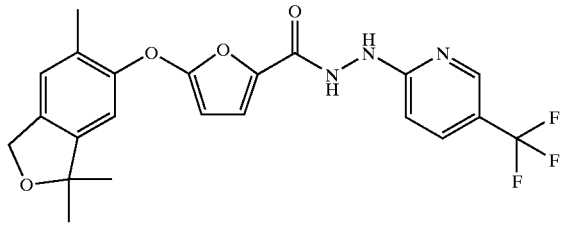

Compound N4 was synthesized according to scheme N. $^1$H NMR (CDCl$_3$): δ 1.45(6H, s), 2.28(3H, s), 5.00(2H, s), 5.45(1H, d, J=3.78 Hz), 6.92(1H, d, J=8.69 Hz), 6.98(1H, s), 7.18(1H, s), 7.22(1H, d, J=3.78 Hz), 7.88(1H, m), 8.33(1H, s); APCI-MS m/z 448 (M+H)$^+$

Biological Testing And Enzyme Assays In Vitro Assays

Assessment of GnRH Receptor Activation Using Microphysiometry

By performing assays such as those described below, the functionality of the compounds of the invention as GnRH antagonists may be confirmed.

Materials and Methods

GnRH, Ac-D-2-Nal-p-chloro-D-Phe-β-(3-pyridyl)-D-Ala-Ser-Lys(nicotinoyl)-D-Lys(nicotinoyl)-Leu-Lys(isopropyl)-Pro-D-Ala-NH$_2$ (antide), and the superagonist peptide [D-Ala$^6$, des-Gly$^{10}$]proethylamide$^9$-LHRH (GnRH-A) may be purchased from Bachem (Torrance, Calif.). Cell Culture media and forskolin may be purchased from Sigma (St. Louis, Mo.). Fetal bovine serum (FBS) and penicillin/streptomycin are available from Omega Scientific, Inc. (Tarzana, Calif.). G418 may be obtained from Gemini (Calabasas, Calif.).

Total Inositol Phosphates Measurement

The activity of various GnRH peptide agonists is initially assessed utilizing an assay that measures accumulation of total inositol phosphates. Approximately 200,000 GGH$_3$ cells/well are plated onto 24-well tissue culture plates using DMEM media. The following day, cells are loaded with [$^3$H]myoinositol (0.5 Ci/ml) for 16–18 hours in inositol-free medium. The medium is aspirated and the cells rinsed with serum-free DMEM. Cells are stimulated with GnRH (0.1 nM–1 μM) or the superagonist, GnRH-A (0.01 nM–100 nM) dissolved in DMEM media in a total volume of 1 mL containing 10 mM LiCl at 37° C. for 45 minutes. The media is replaced with 1 mL ice-cold 10 mM formic acid, which stops the reaction and also serves to extract cellular lipids. Inositol phosphates are separated by ion-exchange chromatography on Dowex columns, which are washed with 2.5 mL of 10 mM myoinositol and 10 mM formic acid. The columns are then washed with 5 mL of 60 mM sodium formate and 5 mM borax, and total inositol phosphates are eluted with 5 mL 1M ammonium formate, 0.1M formic acid. The column eluates are added to liquid scintillation vials containing 15 ml of scintillation cocktail and are counted by liquid scintillation counting.

Preparation of $^{125}$I-GnRH-A Radioligand

The radioiodinated agonist analog of GnRH, $^{125}$I-GnRH-A, is used as the radioligand. One μg of GnRH-A diluted in 0.1M acetic acid is added to an Iodogen®-coated borosilicate glass tube (Pierce) containing 35 μl of 0.05 M phospate buffer (pH 7.4–7.6) and 1 mCi of Na[$^{125}$I]. The reaction mixture is vortexed and incubated for 1 min at room temperature. 2 ml of 0.5 M acetic acid is added to the reaction tube and the mixture is added to a C18 Sep-Pak cartridge. The cartridge is washed with subsequent washes of 5 ml H$_2$O and 5 ml 0.5M acetic acid and then eluted with 5×1 ml of 60% CH$_3$CN/40% 0.5M acetic acid. The eluate is diluted with 3× volume of HPLC buffer A (0.1% TFA in H$_2$O) and loaded onto a C18 column. The iodinated product were eluted over 20–25 min with a gradient of 25–100% CH$_3$CN containing 0.1%TFA. The radioactive fractions (750 μl/fraction) are collected into clean polypropylene tubes containing 100 μl of 10% BSA. Fractions are assessed for biological activity by radioligand binding.

Microphysiometry

The Cytosensor® Microphysiometer (Molecular Devices, Sunnyvale, Calif.) is a real-time, noninvasive, nonradioactive semiconductor-based system for monitoring the cellular responses to various stimuli. It is based on a pH-sensitive silicon sensor, the light-addressable potentiometric sensor which forms part of a microvolume flow chamber in which cultured cells are immobilized (14, 15, 17). GGH$_3$ cells are seeded in low-buffered minimal essential media (MEM, Sigma) containing 25 mM NaCl and 0.1% BSA at a density of 500,000 cells/capsule onto the polycarbonate membrane (3 μm porosity) of cell capsule cups (Molecular Devices, Sunnyvale, Calif.). Capsule cups are transferred to sensor chambers where cells are held in close apposition to a silicon sensor within a sensor chamber, which measures small changes in pH in the microvolume of the sensor chamber. Low-buffered medium is pumped continuously across the cells at a rate of approximately 100 μl/min from one of two fluid reservoirs. A selection valve determines which reservoir from which fluid is perfused onto the cells.

The Cytosensor® Microphysiometer generates a voltage signal, which is a linear function of pH, every second. In order to measure acidification rates, flow to the sensor chamber containing the cells is periodically interrupted, allowing excreted acidic metabolites to build up in the extracellular fluid of the cells. Cells are maintained at 37° C. on a two-minute flow cycle with cells being perfused with media for 80 seconds followed by 40 seconds in which the flow of media is stopped. During this 40-second interval, acidification rates are measured for a 30 sec interval. In this fashion, a single acidification rate is calculated every two min. The Cytosensor® Microphysiometer device contains eight such sensor units, allowing for eight simultaneous experiments to be performed. Each unit is individually programmed utilizing a computer linked to the system.

$GGH_3$ cells are initially equilibrated in the low-buffered MEM media for a period of 30–60 min in which basal acidification rates (measured as $\mu V/sec$), in the absence of any stimuli, are monitored. When the basal rate of acidification changes by less than ten percent over a period of twenty minutes, experiments are initiated. Time course experiments are performed to determine the optimal time for agonist exposure prior to acidification rate measurement and the duration of exposure needed to obtain peak acidification responses to various agonists. From these time course experiments, it has been determined that cells should be exposed to GnRH peptide agonists at least one minute prior to collection of acidification rate data. Peak acidification rates usually occur in the first two-min exposure cycle. When the effects of various inhibitors are measured, cells are pretreated for 20 min with test compound diluted in low-buffered MEM containing 1% DMSO final concentration prior to exposure of the cells for 4 min to a solution containing GnRH or PMA at appropriate concentration in the presence of inhibitor.

Data Analysis

Cytosensor® Microphysiometer data are normalized utilizing Cytosoft® software (Molecular Devices, Sunnyvale, Calif.). $EC_{50}$ values for agonists and $IC_{50}$ values for inhibitors are generated utilizing Prism™ (version 2.01, GraphPad Software, San Diego, Calif.), a computer graphics and statistics program. Values for multiple experiments are presented as means±SE of at least three replicate experiments.

Cell Culture

HEK 293 cells stably transfected with mouse or human GnRH receptors as described above are grown in Dulbecco's high-glucose, modified Eagle's medium (DMEM) supplemented with 0.2% G418, 10% fetal bovine serum (FBS) and 100U/mL penicillin/streptomycin. $GH_3$ cells stably transfected with the rat GnRH receptor ($GGH_3$) were provided by Dr. William Chin (Harvard Medical School, Boston, Mass.). These cells are extensively characterized previously (Kaiser et al., 1997). The cells are grown in low glucose DMEM containing: 100U/mL penicillin/streptomycin, 0.6% G418 and 10% heat-inactivated FBS.

Cell Membrane Preparation

HEK 293 cells containing mouse or human receptors, or rat pituitaries (Pel Freez Biologicals, Rogers, Ark.) are homogenized in buffer A containing: 50 mM Tris (pH 7.4), 0.32 M sucrose, 2 mM EGTA, 1 mM PMSF, 5 $\mu g/ml$ aprotinen, 5 $\mu g/ml$ Pepstatin A, and 1 $\mu g/ml$ leupeptin. Homogenized cells are centrifuged at 4° C. at 20,000×g for 25 minutes, re-suspended in buffer A and re-centrifuged at 4° C. at 20,000×g for an additional 25 minutes. Total membrane protein was determined with a BCA kit (Pierce, Rockford, Ill.). Membranes are stored at −70° C. at a final membrane protein concentration of approximately 5 mg/ml.

Pharmacokinetics

Rats (male or female, 200–225 g) are prepared with indwelling jugular vein cannula as described by Harms et al., Applied Physiol. 36:391–398 (1974), and allowed to recover overnight with free access to the standard vivarium chow and water. The compounds are administered to female rats at 5 mg/kg i.v. and 10 mg/kg p.o. as solutions in 10% DMSO+10% cremophor+80% saline or 10% cremophor+ 90% saline. The male rats are dosed orally at 50 mg/kg in the vehicles specified in Table 3. The blood samples are withdrawn at specific times, plasma is immediately separated and compound extracted with ethyl acetate. The samples are analyzed by LC-MS using 30–90% gradient of ACN in 50 mM ammonium acetate.

The pharmacokinetic parameters are calculated using WinNonlin software (Scientific Consulting Inc.). The bioavailability is calculated as AUCp.o./AUCi.v., where AUCp.o. and AUCi.v. are areas under the plasma concentration-time curve after oral and i.v. administration, respectively.

Radioligand Preparation

The radioiodinated agonist analog of GnRH, [des-Gly$^{10}$, D-Ala$^6$]GnRH ethylamide ($^{125}$I-GnRH-A), is used as the radioligand. One $\mu g$ of GnRH-A diluted in 0.5 M phosphate buffer (pH 7.4) is added to an Iodogen®-coated borosilicate glass tube (Pierce, Rockford, Ill.) containing 35 $\mu l$ of 0.05 M phosphate buffer (pH 7.4–7.6) and 1 mCi of Na[$^{125}$I]. The reaction mixture is vortexed and incubated for 1 minute at room temperature. After one minute, the mixture is vortexed and allowed to incubate for an additional minute. 2 ml of 0.5 M acetic acid/1% BSA is added to the reaction tube and the mixture is added to a C18 Sep-Pak cartridge. The cartridge is washed with subsequent washes of 5 ml $H_2O$ and 5 ml 0.5 M acetic acid and then eluted with 5×1 ml of 60%$CH_3CN$/ 40% 0.5 M acetic acid. The eluate is diluted with 3× volume of HPLC buffer A (0.1% TFA in $H_2O$) and loaded onto a C18 column. The iodinated product is eluted over 20–25 min with a gradient of 25–100% $CH_3CN$ containing 0.1% TFA. The radioactive fractions (750 $\mu l$/fraction) are collected into clean polypropylene tubes containing 100 $\mu l$ of 10% BSA. Fractions are assessed for biological activity by radiolig and binding. Specific activity of the radioligand was approximately 2200 Ci/mmol.

Radioligand Binding Assays

Membranes are diluted to 0.01–0.5 mg/ml (depending upon the species of receptor) with assay buffer containing 50 mM HEPES (pH 7.4), 1 mM EDTA, 2.5 mM $MgCl_2$, and 0.1% BSA. Membranes (diluted to utilize similar receptor numbers between assays) are incubated with approximately 0.04–0.06 nM $^{125}$I-GnRH-A in the presence or absence of competing agents (0.1–10,000 nM) in a total volume of 200 $\mu l$ in 96-well polypropylene plates for 1 hour at room temperature. Assays are stopped by rapid filtration onto 96-well GF/C filters soaked in 0.1% polyethylenimine (PEI) utilizing a Packard 96-well cell harvester. Filters are washed three times with ice-cold PBS (50 mM $NaPO_4$, 0.9% NaCl, 2 mM $MgCl_2$, and 0.02% $NaN_3$, pH 7.4). 35 $\mu l$ of scintillation cocktail is added to each filter well and filters are counted on a Packard Topcount. Control dose-response curves are generated to GnRH (0.1 nM–100 nM) in each competition binding experiment. Binding inhibition constants ($K_i$) for the GnRH agents are calculated and are provided in Table 1 below. $K_i$ values were calculated from IC50 values according to Cheng et al., *Biochemical Pharmacol.* 22: 3099–3108, 1973.

$$K_i = \frac{IC_{50}}{1 + \frac{[\text{ligand}]}{K_d \text{ of ligand}}}$$

Following procefures described above, the following results summarized in Table 1 were obtained.

TABLE 1

$K_i$ for GnRH Agents: Inhibition Binding of $^{125}$I-GnRH-A to GnRH Receptors of Various Species

| Example No. | GnRH Receptor | $K_i$ (nM) |
|---|---|---|
| A1 | Human | 1840 |
|  | Mouse | ND |
|  | Rat | ND |
| A2 | Human | 700 |
|  | Mouse | ND |
|  | Rat | ND |
| B1 | Human | 710,000 |
|  | Mouse | ND |
|  | Rat | ND |
| B2 | Human | 310 |
|  | Mouse | ND |
|  | Rat | ND |
| B3 | Human | 95 |
|  | Mouse | 84 |
|  | Rat | 65 |
| C1 | Human | 3 |
|  | Mouse | 7 |
|  | Rat | 6.5 |
| C2 | Human | 9.5 |
|  | Mouse | 23 |
|  | Rat | 32 |
| C3 | Human | 300 |
|  | Mouse | ND |
|  | Rat | ND |
| C4 | Human | 1.3 |
|  | Mouse | 8.2 |
|  | Rat | 22 |
| C5 | Human | 25 |
|  | Mouse | 10 |
|  | Rat | 12 |
| C6 | Human | 42 |
|  | Mouse | 18 |
|  | Rat | 6 |
| C7 | Human | 1740 |
|  | Mouse | ND |
|  | Rat | ND |
| C8 | Human | 410 |
|  | Mouse | ND |
|  | Rat | ND |
| C9 | Human | 61 |
|  | Mouse | 30 |
|  | Rat | 47 |
| C10 | Human | 350 |
|  | Mouse | ND |
|  | Rat | ND |
| C11 | Human | 63 |
|  | Mouse | 67 |
|  | Rat | 84 |
| C12 | Human | 46 |
|  | Mouse | 33 |
|  | Rat | 39 |
| C13 | Human | 220 |
|  | Mouse | 130 |
|  | Rat | 240 |
| D1 | Human | ND |
|  | Mouse | ND |
|  | Rat | ND |
| E1 | Human | 4.2 |
|  | Mouse | 12 |
|  | Rat | 9 |
| E2 | Human | 300 |
|  | Mouse | ND |
|  | Rat | ND |
| E3 | Human | 840 |
|  | Mouse | ND |
|  | Rat | 91 |
| E4 | Human | 24 |
|  | Mouse | ND |
|  | Rat | 23 |
| E5 | Human | 390 |
|  | Mouse | ND |
|  | Rat | ND |
| F1 | Human | 2 |
|  | Mouse | 3.5 |
|  | Rat | 5.2 |
| F2 | Human | 3.3 |
|  | Mouse | 8.2 |
|  | Rat | 8.5 |
| F3 | Human | 80 |
|  | Mouse | 136 |
|  | Rat | 535 |
| F4 | Human | 126 |
|  | Mouse | 450 |
|  | Rat | 384 |
| G1 | Human | 10 |
|  | Mouse | 22 |
|  | Rat | 34 |
| G2 | Human | 370 |
|  | Mouse | 740 |
|  | Rat | 1330 |
| H1 | Human | 5600 |
|  | Mouse | ND |
|  | Rat | ND |
| I1 | Human | 630 |
|  | Mouse | ND |
|  | Rat | ND |
| I2 | Human | 2.4 |
|  | Mouse | 3.6 |
|  | Rat | 4.2 |
| I3 | Human | 5770 |
|  | Mouse | ND |
|  | Rat | ND |
| I4 | Human | 980 |
|  | Mouse | ND |
|  | Rat | ND |
| I5 | Human | 1210 |
|  | Mouse | ND |
|  | Rat | ND |
| I6 | Human | 50 |
|  | Mouse | 61 |
|  | Rat | 79 |
| I7 | Human | 2.8 |
|  | Mouse | 11 |
|  | Rat | 17 |
| I8 | Human | 6.3 |
|  | Mouse | 16 |
|  | Rat | 29 |
| I9 | Human | 1.2 |
|  | Mouse | 2.1 |
|  | Rat | 3.8 |
| I10 | Human | 146 |
|  | Mouse | 160 |
|  | Rat | 230 |
| I11 | Human | 170 |
|  | Mouse | 250 |
|  | Rat | 790 |
| I12 | Human | 165 |
|  | Mouse | 260 |
|  | Rat | 1160 |
| I13 | Human | 40 |
|  | Mouse | ND |

TABLE 1-continued

K$_i$ for GnRH Agents: Inhibition Binding of $^{125}$I-GnRH-A to GnRH Receptors of Various Species

| Example No. | GnRH Receptor | K$_i$ (nM) |
|---|---|---|
| I14 | Rat | ND |
| | Human | 225 |
| | Mouse | ND |
| I15 | Rat | ND |
| | Human | 7.2 |
| | Mouse | ND |
| I16 | Rat | 19 |
| | Human | 9 |
| | Mouse | ND |
| I17 | Rat | 18 |
| | Human | 70 |
| | Mouse | 43 |
| I18 | Rat | 50 |
| | Human | 58 |
| | Mouse | 59 |
| I19 | Rat | 154 |
| | Human | 17 |
| | Mouse | 44 |
| I20 | Rat | 39 |
| | Human | 3.8 |
| | Mouse | 4 |
| I21 | Rat | 7.3 |
| | Human | 4.2 |
| | Mouse | 5 |
| I22 | Rat | 22 |
| | Human | 10 |
| | Mouse | ND |
| I23 | Rat | 52 |
| | Human | 30 |
| | Mouse | 22 |
| I24 | Rat | 370 |
| | Human | ND |
| | Mouse | ND |
| I25 | Rat | ND |
| | Human | 31 |
| | Mouse | 38 |
| I26 | Rat | 59 |
| | Human | 8.3 |
| | Mouse | 14 |
| I27 | Rat | 25 |
| | Human | 101 |
| | Mouse | 122 |
| I28 | Rat | 370 |
| | Human | 0.3 |
| | Mouse | 2.6 |
| I29 | Rat | 4.2 |
| | Human | 49 |
| | Mouse | 58 |
| I30 | Rat | 64 |
| | Human | 630 |
| | Mouse | ND |
| J1 | Rat | ND |
| | Human | 450 |
| | Mouse | ND |
| J2 | Rat | ND |
| | Human | 550 |
| | Mouse | ND |
| J3 | Rat | ND |
| | Human | 400 |
| | Mouse | ND |
| J4 | Rat | ND |
| | Human | 2000 |
| | Mouse | ND |
| J5 | Rat | ND |
| | Human | 1400 |
| | Mouse | ND |
| J6 | Rat | ND |
| | Human | 16100 |
| | Mouse | ND |
| J7 | Rat | ND |
| | Human | 35 |
| | Mouse | 50 |
| J8 | Rat | 20 |
| | Human | 3890 |
| | Mouse | ND |
| J9 | Rat | ND |
| | Human | 4770 |
| | Mouse | ND |
| J10 | Rat | ND |
| | Human | 1690 |
| | Mouse | ND |
| J11 | Rat | ND |
| | Human | 710,000 |
| | Mouse | ND |
| J12 | Rat | ND |
| | Human | 260 |
| | Mouse | 850 |
| J13 | Rat | 1200 |
| | Human | >10,000 |
| | Mouse | ND |
| J14 | Rat | ND |
| | Human | >10,000 |
| | Mouse | ND |
| J15 | Rat | ND |
| | Human | 0.9 |
| | Mouse | 3.3 |
| J16 | Rat | 2.0 |
| | Human | 97 |
| | Mouse | 233 |
| J17 | Rat | 122 |
| | Human | 610 |
| | Mouse | ND |
| J18 | Rat | ND |
| | Human | 170 |
| | Mouse | 480 |
| J19 | Rat | 290 |
| | Human | 140 |
| | Mouse | 320 |
| J20 | Rat | 230 |
| | Human | 1410 |
| | Mouse | ND |
| J21 | Rat | ND |
| | Human | 10,000 |
| | Mouse | ND |
| J22 | Rat | ND |
| | Human | 12 |
| | Mouse | 24 |
| J23 | Rat | 110 |
| | Human | 140 |
| | Mouse | 280 |
| J24 | Rat | 660 |
| | Human | 130 |
| | Mouse | 400 |
| J25 | Rat | 1130 |
| | Human | 1670 |
| | Mouse | ND |
| J26 | Rat | ND |
| | Human | 1.6 |
| | Mouse | ND |
| J27 | Rat | 17 |
| | Human | ND |
| | Mouse | ND |
| J28 | Rat | ND |
| | Human | 30 |
| | Mouse | 130 |
| J29 | Rat | 245 |
| | Human | 5230 |
| | Mouse | ND |
| J30 | Rat | ND |
| | Human | 480 |
| | Mouse | ND |
| K1 | Rat | ND |
| | Human | 4430 |
| | Mouse | ND |
| K2 | Rat | ND |
| | Human | 710,000 |
| | Mouse | ND |
| | Rat | ND |

TABLE 1-continued

K$_i$ for GnRH Agents: Inhibition Binding of
$^{125}$I-GnRH-A to GnRH Receptors of Various Species

| Example No. | GnRH Receptor | K$_i$ (nM) |
|---|---|---|
| L1 | Human | 2110 |
|  | Mouse | ND |
|  | Rat | ND |
| L2 | Human | 5020 |
|  | Mouse | ND |
|  | Rat | ND |
| M1 | Human | 23 |
|  | Mouse | ND |
|  | Rat | 11 |
| M2 | Human | 19 |
|  | Mouse | ND |
|  | Rat | 29 |
| M3 | Human | 4.1 |
|  | Mouse | ND |
|  | Rat | 2.9 |
| M4 | Human | 1.8 |
|  | Mouse | 3.7 |
|  | Rat | 3.9 |
| N1 | Human | 1140 |
|  | Mouse | ND |
|  | Rat | ND |
| N2 | Human | 28 |
|  | Mouse | 22 |
|  | Rat | 86 |
| N3 | Human | 130 |
|  | Mouse | ND |
|  | Rat | 100 |
| N4 | Human | 1500 |
|  | Mouse | ND |
|  | Rat | ND |

ND = not determined

In Vitro Metabolism

Human, rat, dog, and monkey liver microsomes are isolated by differential centrifugation. Specimens of human liver were obtained from the International Institute for the Advancement of Medicine (Scranton, Pa.). The disappearance of the parent compound is studied in a mixture containing 5 uM compound, 0.5 mg/ml microsomal protein, and 2 mM NADPH in 50 mM K Phosphate buffer, pH 7.4. Samples are incubated for 30 minutes at 37° C. The reaction is terminated by the addition of acetonitrile and compounds analyzed by LC-MS as described above.

In Vivo Tests

Animal Models to Assess Activity of GnRH Antagonists

Model # 1: Castrated Male Rat Model

The castrated male rat is a sensitive and specific model for evaluating GnRH antagonists (Heber, 1982, Puente, 1986)). Removal of the testes produces a model with GnRH-mediated elevations of circulating LH. This mechanism of action of the hypothalamic-pituitary-gonadal axis is well-defined (Ellis and Desjardins, 1984). Suppression of LH in this model following administration of a GnRH antagonist reflects blockade of the GnRH receptor.

Male Sprague-Dawley (200–225 g) rats are castrated via the scrotal approach under halothane anesthesia. Animals are allowed 14 days post operative recovery prior to study. Thirteen days following castration, animals are anesthetized with halothane and instrumented with indwelling jungular vein cannula. Details of the cannulation procedure have been described previously, see Harms and Ojeda, 1974. On study day, animals are allowed to acclimate to the procedure room while residing in their home case. Basal blood samples are drawn from all animals. Immediately following basal sampling, vehicle (10% DMSO, 10% Cremophor EL and 80% physiological saline) or test compounds are administered by intravenous (iv), intraperitoneal (ip), intramuscular (im), or oral (op) routs. Test compounds are formulate in 10% DMSO, 10% Cremophol EL and 80% physiological saline. Blood samples are drawn into heparin containing tubes at multiple time points post treatment. Blood is centrifuged immediately, plasma collected and stored in −20° freezer until assayed. Plasma samples are analyzed using DSL-4600 ACTIVE LH coated-tube immunoradiometric assay kit from Diagnostic Systems Laboratories, Inc. Webster Texas. Cremophor EL is obtained from Sigma, St. Louis, Mo.

Model # 2: Intact Male Rat Model

Testosterone is a hormone regulated by the hypothalamic-pituitary-gonadal axis. GnRH is secreted in pulses from the hypothalamus and stimulates the anterior pituitary gland to release the gonadotropic hormones luteinizing hormone (LH) and follicle stimulating hormone (FSH). Testosterone is produced when the testes are stimulated by LH. A GnRH antagonist is expected to reduce testosterone levels by inhibiting GnRH stimulation of LH release.

Male Sprague-Dawley (250–275 g) rats were single-housed and allowed to acclimate from 1 week prior to study. On study day animals were treated with vehicle (10% DMSO, 10%. Cremophor EL and 80% physiological saline) or test compound. Blood samples were obtained via cardiac puncture under halothane anesthesia at predetermined time points post treatment. Blood samples were drawn into heparin containing tubes. Blood was centrifuged immediately, plasma collected and stored in −20° freezer until assayed. Plasma samples were analyzed using DSL-4000 ACTIVE Testosterone coated-tube radioimmunoassay kit from Diagnostic Systems Laboratories, Inc. Webster, Tex.

The following results show in Table 2 were obtained from tests as described above.

TABLE 2

| No | Huma % p. 30' | Male t % p. 30' | M T$_{1/}$ hr | M C$_m$ □ | MR T$_{max}$ hr | M F$_p$. | Fem. t % rem. 30' | FR T$_{1/}$ hr | FR C$_{ma}$ □ M | FR T$_{max}$ hr | FR F$_{p.o.}$ |
|---|---|---|---|---|---|---|---|---|---|---|---|
| C1 | 63 | 99 | 1.3 | 0.2 | 1 | 1% | 22 | 2.5 | 1.2 | 1 | 19%[1] |
| C2 | 40 | 97 | 1.2 | 0.7 | 1 | 4% | 18 | 2.5 | 0.9 | 2 | 15%[1] |
| C5 | 52 | ND | ND | ND | ND | ND | ND | ND | ND | ND | ND |

TABLE 2-continued

| No | Human % p. 30' | Male t % p. 30' | M $T_{1/2}$ hr | M $C_m$ □ | MR $T_{max}$ hr | M $F_p$ | Fem. t % rem. 30' | FR $T_{1/2}$ hr | FR $C_{ma}$ □ M | FR $T_{max}$ hr | FR $F_{p.o.}$ |
|---|---|---|---|---|---|---|---|---|---|---|---|
| C6 | 75 | 95 | ND | ND | ND | ND | ND | 6.2 | ND | ND | <1%[2] |
| J7 | 57 | 89 | ND | ND | ND | ND | 9 | 1.5 | 0.2 | 0.5 | 4%[2] |
| J1 | 59 | ND | ND | ND | ND | ND | 42 | 1.8 | 0.6 | 1 | 23%[2] |
| J1 | 71 | 99 | ND | ND | ND | ND | 46 | 2.7 | 0.2 | 1 | 10%[2] |
| J1 | 61 | 99 | ND | ND | ND | ND | 42 | ND | ND | ND | ND |
| J1 | 46 | ND | ND | ND | ND | ND | ND | ND | ND | ND | ND |
| F2 | 65 | 93 | ND | ND | ND | ND | 22 | 1.7 | 0.3 | 0.5 | 8%[3] |
| J1 | 41 | 95 | ND | ND | ND | ND | 19 | ND | ND | ND | ND |
| E1 | 43 | 96 | ND | ND | ND | ND | 27 | 2 | 3.6 | 1 | 57%[4] |
| J1 | 91 | ND | ND | ND | ND | ND | ND | ND | ND | ND | ND |
| C9 | 61 | 94 | ND | ND | ND | ND | 14 | ND | ND | ND | ND |
| C1 | 63 | ND | ND | ND | ND | ND | ND | ND | ND | ND | ND |
| C1 | 54 | ND | ND | ND | ND | ND | 30 | ND | ND | ND | ND |
| C1 | 37 | ND | ND | ND | ND | ND | 14 | ND | ND | ND | ND |
| C1 | 38 | ND | ND | ND | ND | ND | ND | ND | ND | ND | ND |
| E2 | 30 | ND | ND | ND | ND | ND | ND | ND | ND | ND | ND |
| J2 | 59 | ND | ND | ND | ND | ND | ND | ND | ND | ND | ND |
| J2 | 35 | ND | ND | ND | ND | ND | ND | ND | ND | ND | ND |
| F1 | 41 | ND | ND | ND | ND | ND | 24 | 1.3 | 0.6 | 1 | 5%[3] |
| J2 | 91 | ND | ND | ND | ND | ND | ND | 2.4 | 0.2 | 0.5 | 6%[3] |
| G1 | 81 | ND | ND | ND | ND | ND | 41 | 1.7 | 0.3 | 0.5 | 4%[3] |
| G2 | 55 | ND | ND | ND | ND | ND | ND | ND | ND | ND | ND |
| I3 | 43 | ND | ND | ND | ND | ND | ND | ND | ND | ND | ND |
| I5 | 58 | ND | ND | ND | ND | ND | ND | ND | ND | ND | ND |

[1] 20 mg/kg as 10 mg/ml solution in 10% DMSO 10% cremophor 80% saline
[2] 10 mg/kg as 5 mg/ml solution in 10% DMSO 105 cremophor 80% saline
[3] 10 mg/kg as 5 mg/ml solution in 10% cremophor 90% saline
[4] 10 mg/kg as 5 mg/ml solution in 10% EtOH 10% cremophor 80% saline

Pharmaceutical Compositions

The exemplary compounds described above may be formulated into pharmaceutical compositions according to the following general examples.

Parenteral Composition

To prepare a parenteral pharmaceutical composition suitable for administration by injection, 100 mg of a water-soluble salt of a compound of the Formula I or II is dissolved in DMSO and then mixed with 10 mL of 0.9% sterile saline. The mixture is incorporated into a dosage unit form suitable for administration by injection.

Oral Composition

To prepare a pharmaceutical composition for oral delivery, 100 mg of a compound of Formula I or II is mixed with 750 mg of lactose. The mixture is incorporated into an oral dosage unit for, such as a hard gelatin capsule, which is suitable for oral administration.

Intraocular Composition

To prepare a sustained release pharmaceutical composition for intraocular delivery, a compound of Formula I or II is suspended in a neutral, isotonic solution of hyaluronic acid (1.5% conc.) in a phosphate buffer (pH 7.4) to form a 1% suspension, which is suitable for intraocular administration.

It is to be understood that the foregoing description is exemplary and explanatory in nature, and is intended to illustrate the invention and its preferred embodiments. Thus, the scope of the invention should be understood to be defined not by the foregoing description, but by the following claims and their equivalents.

What is claimed is:

1. A compound represented by Formula I:

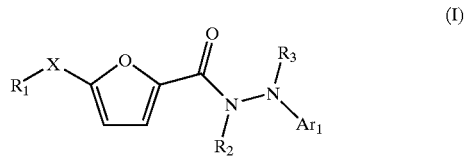

(I)

wherein:

$R_1$ is selected from the group consisting of $C_3$–$C_{10}$ alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl,—O-cycloalkyl, —NH-cycloalkyl, —O-heterocycloalkyl, or —NH-heterocycloalkyl group unsubstituted or substituted with one or more substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$^z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS ($O_2$)H, —NHC(SO)H, —NHC(S)H, and —SH groups unsubstituted or substituted with one or more substituents selected from the group consisting of halogens, =O, —$NO_2$, —CN, —$(CH_2)_z$—CN where z is an integer from 0 to 4, —$OR_c$, —$NR_cOR_c$, —$NR_cR_c$, —C(O)$NR_c$, —C(O)$OR_c$, —C(O)$R_c$, —$NR_c$C(O) $NR_cR_c$, —$NR_c$C(O)$R_c$, —OC(O)$OR_c$, —OC(O) $NR_cR_c$, —$SR_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group;

X is selected from the group consisting of: C($A_1$)($A_2$) wherein $A_1$ and $A_2$ are each independently hydrogen, or an unsubstituted alkyl, heteroalkyl, aryl, heteroaryl, cycloalkyl, heterocycloalkyl, or haloalkyl group; N($A_3$) wherein $A_3$ is hydrogen or an unsubstituted alkyl, heteroalkyl, aryl, heteroaryl, cycloalkyl, heterocycloalkyl, or haloalkyl group; O; S; SO; and $SO_2$;

$R_2$ is hydrogen or an unsubstituted alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group;

$R_3$ is hydrogen or an unsubstituted alkyl, alkenyl, heteroalkyl, haloalkyl, alkynyl, aryl, cycloalkyl, heterocycloalkyl, heteroaryl, —O-aryl, —NH-aryl, —O-heteroaryl, —NH-heteroaryl, —O-cycloalkyl, —NH-cycloalkyl, —O-heterocycloalkyl, or —NH-heterocycloalkyl group; and $Ar_1$ is selected from the group consisting of aryl, cycloalkyl, heterocycloalkyl, and heteroaryl groups unsubstituted or substituted with one or more substituents independently selected from the group consisting of: halogens; =O; =S; —CN; and —$NO_2$; and alkyl, alkenyl, heteroalkyl, haloalkyl, alkynyl, aryl, cycloalkyl, heterocycloalkyl, heteroaryl, —$(CH_2)_z$CN where z is an integer from 0 to 4, =NH, —NHOH, —OH, —C(O)H, —OC(O)H, —C(O)OH, —OC(O) OH, —OC(O)OC(O)H, —OOH, —C(NH)$NH_2$, —NHC(NH)$NH_2$, —C(S)$NH_2$, —NHC(S)$NH_2$, —NHC(O)$NH_2$, —S($O_2$)H, —S(O)H, —$NH_2$, —C(O) $NH_2$, —OC(O)$NH_2$, —NHC(O)H, —NHC(O)OH, —C(O)NHC(O)H, —OS($O_2$)H, —OS(O)H, —OSH, —SC(O)H, —S(O)C(O)OH, —$SO_2$C(O)OH, —NHSH, —NHS(O)H, —$NHSO_2$H, —C(O)SH, —C(O)S(O)H, —C(O)S($O_2$)H, —C(S)H, —C(S)OH, —C(SO)OH, —C($SO_2$)OH, —NHC(S)H, —OC(S)H, —OC(S)OH, —OC($SO_2$)H, —S($O_2$)$NH_2$, —S(O) $NH_2$, —$SNH_2$, —$NHCS(O_2)$H, —NHC(SO)H, —NHC(S)H, and —SH groups unsubstituted or substituted with one or more substituents selected from the group consisting of halogens, =O, —$NO_2$, —CN, —$(CH_2)_z$—CN where z is an integer from 0 to 4, —$OR_c$, —$NR_c$, $OR_c$, —$NR_cR_c$, —C(O)$NR_c$, —C(O) $OR_c$, —C(O)$R_c$, —$NR_c$C(O)$NR_cR_c$, —$NR_c$C(O)$R_c$, —OC(O)$OR_c$, —OC(O) $NR_cR_c$, —$SR_c$, unsubstituted alkyl, unsubstituted alkenyl, unsubstituted alkynyl, unsubstituted aryl, unsubstituted cycloalkyl, unsubstituted heterocycloalkyl, and unsubstituted heteroaryl, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group;

or a pharmaceutically acceptable salt of said compound.

2. A compound according to claim 1 wherein $R_1$ is selected from the group consisting of aryl, cycloalkyl, heterocycloalkyl, and —O-aryl groups unsubstituted or substituted with one or more substitutents independently selected from the group consisting of: halogens, =O, alkyl, heteroalkyl, aryl, cycloalkyl, —OH, —C(O)H, and —C(O) $NH_2$ groups unsubstituted or substituted with one or more substitutents selected from the group consisting of —C(O) $NR_c$, unsubstituted alkyl, unsubstitued aryl, and unsubstituted cycloalkyl, where $R_c$ is hydrogen or unsubstituted alkyl.

3. A compound according to claim 1 wherein X is $CH_2$ or O.

4. A compound according to claim 1 wherein $R_2$ is hydrogen and $R_3$ is hydrogen or alkyl.

5. A compound according to claim 1 wherein $Ar_1$ is an aryl or heteroaryl group unsubstituted or substituted with one or more substituents independently selected from the group consisting of: halogens; and alkyl, heteroalkyl, haloalkyl, cycloalkyl, —OH, —$NH_2$, and —S(O)$NH_2$ groups unsubstituted or substituted with one or more substitutents selected from the group consisting of unsubstituted alkyl, unsubstituted cycloalkyl, and unsubstituted heterocycloalkyl.

6. A compound according to claim 5 wherein:

$R_1$ is selected from the group consisting of aryl, cycloalkyl, heterocycloalkyl, and —O-aryl unsubstituted or substituted with one or more substitutents independently selected from the group consisting of: halogens, =O, alkyl, heteroalkyl, aryl, cycloalkyl, —OH, —C(O)H, and —C(O)$NH_2$ groups unsubstituted or substituted with one or more substitutents selected from the group consisting of —C(O)$NR_c$, unsubstituted alkyl, unsubstitued aryl, and unsubstituted cycloalkyl, where $R_c$ is hydrogen or unsubstituted alkyl;

X is $CH_2$ or O;

$R_2$ is hydrogen; and $R_3$ is hydrogen or alkyl.

7. A pharmaceutical composition comprising a therapeutically effective amount of a compound as defined in claims 1, and a pharmaceutically acceptable carrier.

* * * * *